(12) United States Patent
Zagon et al.

(10) Patent No.: US 9,375,458 B2
(45) Date of Patent: *Jun. 28, 2016

(54) COMBINATORIAL THERAPIES FOR THE TREATMENT OF NEOPLASIAS USING THE OPIOID GROWTH FACTOR RECEPTOR

(71) Applicant: The Penn State Research Foundation, University Park, PA (US)

(72) Inventors: Ian S. Zagon, Hummelstown, PA (US); Patricia J. McLaughlin, Harrisburg, PA (US); Jill P. Smith, Camp Hill, PA (US)

(73) Assignee: The Penn State Research Foundation, University Park, PA (US)

(*) Notice: Subject to any disclaimer, the term of this patent is extended or adjusted under 35 U.S.C. 154(b) by 111 days.

This patent is subject to a terminal disclaimer.

(21) Appl. No.: 13/660,129

(22) Filed: Oct. 25, 2012

(65) Prior Publication Data

US 2013/0084242 A1    Apr. 4, 2013

Related U.S. Application Data

(63) Continuation of application No. 13/020,077, filed on Feb. 3, 2011, now abandoned, which is a continuation of application No. 11/510,682, filed on Aug. 25, 2006, now Pat. No. 8,003,630, which is a continuation of application No. PCT/US2005/005268, filed on Feb. 21, 2005.

(60) Provisional application No. 60/548,021, filed on Feb. 26, 2004.

(51) Int. Cl.

| | |
|---|---|
| *A01N 41/10* | (2006.01) |
| *A61K 31/10* | (2006.01) |
| *A61K 38/18* | (2006.01) |
| *C07K 14/475* | (2006.01) |
| *A61K 38/08* | (2006.01) |
| *A61K 31/00* | (2006.01) |
| *A61K 31/138* | (2006.01) |
| *A61K 31/337* | (2006.01) |
| *A61K 31/4745* | (2006.01) |
| *A61K 31/505* | (2006.01) |
| *A61K 31/525* | (2006.01) |
| *A61K 31/573* | (2006.01) |
| *A61K 31/66* | (2006.01) |
| *A61K 31/663* | (2006.01) |
| *A61K 31/704* | (2006.01) |
| *A61K 31/7048* | (2006.01) |
| *A61K 31/7072* | (2006.01) |
| *A61K 31/7076* | (2006.01) |
| *A61K 41/00* | (2006.01) |
| *A61K 45/06* | (2006.01) |
| *A61K 31/282* | (2006.01) |
| *A61K 31/513* | (2006.01) |
| *A61K 31/7068* | (2006.01) |
| *A61K 51/00* | (2006.01) |
| *A61N 5/10* | (2006.01) |
| *A61K 38/33* | (2006.01) |

(52) U.S. Cl.
CPC ............ *A61K 38/08* (2013.01); *A61K 31/00* (2013.01); *A61K 31/138* (2013.01); *A61K 31/282* (2013.01); *A61K 31/337* (2013.01); *A61K 31/4745* (2013.01); *A61K 31/505* (2013.01); *A61K 31/513* (2013.01); *A61K 31/525* (2013.01); *A61K 31/573* (2013.01); *A61K 31/66* (2013.01); *A61K 31/663* (2013.01); *A61K 31/704* (2013.01); *A61K 31/7048* (2013.01); *A61K 31/7068* (2013.01); *A61K 31/7072* (2013.01); *A61K 31/7076* (2013.01); *A61K 38/33* (2013.01); *A61K 41/00* (2013.01); *A61K 45/06* (2013.01); *A61K 51/00* (2013.01); *A61N 5/10* (2013.01)

(58) Field of Classification Search
CPC . A61K 31/7048; A61K 31/282; A61K 31/66; A61K 31/7072; A61K 31/7076; A61K 31/138
USPC .................................................. 514/710, 7.6
See application file for complete search history.

(56) References Cited

U.S. PATENT DOCUMENTS

| | | | | |
|---|---|---|---|---|
| 4,537,878 | A * | 8/1985 | Plotnikoff | .................... 514/18.5 |
| 4,757,049 | A | 7/1988 | Plotnikoff | |
| 4,892,874 | A * | 1/1990 | Temple et al. | ................ 514/249 |
| 6,136,780 | A | 10/2000 | Zagon et al. | |
| 2007/0053838 | A1 | 3/2007 | Zagon et al. | |

OTHER PUBLICATIONS

McLaughlin et. al. (Cancer Letters (2003) 209-217).*
Hitt et. al. (Annals of Oncology (2001) 13:1665-1673).*

(Continued)

*Primary Examiner* — Marcos Sznaidman

(74) *Attorney, Agent, or Firm* — McKee, Voorhees & Sease, PLC

(57) ABSTRACT

The present invention relates to pharmaceutical compositions for treating neoplasias in an animal or human comprised of a carrier and therapeutically effective amounts of at least one chemotherapeutic agent along with the biotherapeutic endogenous pentapeptide Met-enkephalin, referred to as opioid growth factor. Also provided are methods of treating neoplasias in an animal or human in need of such treatment, comprising the administration to the animal or human therapeutically effective amounts of a pharmaceutical composition comprised of a carrier and therapeutically effective amounts of at least one neoplasia-treating agent, such as a chemotherapeutic agent or radiation, along with opioid growth factor.

4 Claims, 26 Drawing Sheets

(56) References Cited

OTHER PUBLICATIONS

Boudewijn et. al. (Cancer Research (1991) 51:211-214).*
Fountzilas et. al. (Annals of Oncology (1999) 10:475-478).*
Su et. al. (Jpn. J. Clin. Oncol. (2000) 30:562-567).*
Abbruzzese (Cancer (2002) 95:941-945).
Bisignani, Geoffrey J. et al., "Human Renal Cell Cancer Proliferation in Tissue Culture is Tonically Inhibited by Opioid Growth Factor", The Journal of Urology—Abstract: vol. 102 (11) Dec. 1999.
Donahue, Renee N. et al., "Cell proliferation of human ovarian cancer is regulated by the opioid growth factor-opioid growth factor receptor axis", Am. J. Physiol. Regul. Integr. Comp. Physiol 296:R1716-1725, 2009.
Goldenberg, David et al., "Expression of Opioid Growth Factor (OGF)-OGF Receptor (OGFr) Axis in Human Nonmedullary Thyroid Cancer", Thyroid, vol. 18, No. 11, 2008.
Goodman and Gilman's the Pharmacological Basis of Therapeutics (Tenth Edition (2001), McGraw Hill, Chapter 1, pp. 3-29).
Hardman, J.G., Editor-in-chief, McGraw-Hill, "Goodman & Gilman's The Pharmacological Basis of Therapeutics", Ninth Edition, US05/05268.
Hitt, R. et al., "Induction chemotherapy with paclitaxel, cisplatin and 5-fluorouracil for squamous cell carcinoma of the head and neck: long-term results of a phase II trial", Annals of Oncology 13:1665-1673, 2002.
Jaglowski, Jeffrey R. et al., "Inhibition of human pancreatic cancer by gemcitablue is enhanced by the opioid growth factor (OGF): In vitro and in vivo studies", Abstract, AAR, Control/Track No. 04-AB-5432-AACR, Nov. 7, 2003.
Jaglowski, Jeffrey R. et al., "Opioid growth factor enhances tumor growth inhibition and increases the survival of paclitaxel-treated mice with squamous cell carcinoma of the head and neck", Cancer Chemother Pharmacol (2005) 56:97-104.
McLaughlin, Patricia J. et al., "Enhanced antitumor activity of paclitaxel on SCCHN with opioid growth factor (OGF): In vitro studies", Faseb Journal, vol. 18, No. 4-5, 2004, Abstract 649.7.
McLaughlin, Patricia J. et al., "Enhanced growth inhibition of squamous cell carcinoma of the head and neck by combination therapy of paclitaxel and opioid growth factor", International Journal of Oncology 26: 809-816, 2005.
McLaughlin, Patricia J. et al., "Opioid growth factor (OGF) inhibits the progression of human squamous cell carcinoma of the head and neck transplanted in nude mice", Cancer Letters 199 (2003) 209-217.
McLaughlin, Patricia J. et al., "Prevention and delay in progression of human squamous cell carcinoma of the head and neck in nude mice by stable overexpression of the opioid growth factor receptor", International Journal of Oncology 33:751-757, 2008.
Monsconi et al. (European Journal of Cancer (1997) 33:S14-S17).
OPRS alerts (Jul. 2005).
Zagon et al., (Cancer Letters (1997) 112:167-175).
Zagon et al., "Endogenous opioid systems regulate growth of neural tumor cells in culture", Brain Research, 490:14-25 (1989). 1989 Elsevier Science Publishers B.V. (Biomedical Division).
Zagon, Ian S. et al., "Combination chemotherapy with gemcitabine and biotherapy with opioid growth factor (OGF) enhances the growth inhibition of pancreatic adenocarcinoma", Cancer Chemother Pharmacol (2005) 56:510-520.
Zagon, Ian S. et al., "Opioid growth factor-opioid growth factor receptor axis is a physiological determinant of cell proliferation of diverse human cancers", Am. J. Physiol Regul. Integr. Comp. Physiol 297: R000-R000, 2009.
Zagon, Ian S. et al., "Overexpression of the opioid growth factor receptor potentiates growth inhibition in human pancreatic cancer cells", International Journal of Oncology, 30:775-783, 2007.
Zagon, Ian S. et al., "Prevention and delay in progression of human pancreatic cancer by stable overexpression of the opioid growth factor receptor", International Journal of Oncology, 33:317-323, 2008.
European Search Report, PCT/US05/05268, The Penn State Research Foundation, Jul. 5, 2005.
Hitt et al., Annals of Oncology (2001) 13:1665-1673).
McLaughlin et al., Cancer Letters (2003) 209-217.
Smith, Jill P. et al., "Treatment of advanced pancreatic cancer with opioid growth factor: phase I", Clinical Report, Anti-Cancer Drugs, Mar. 1, 2004, vol. 15, No. 3, pp. 203-209.

* cited by examiner

COMBINATORIAL THERAPIES FOR THE TREATMENT OF NEOPLASIAS USING THE OPIOID GROWTH FACTOR RECEPTOR

CROSS-REFERENCE TO RELATED APPLICATIONS

This application is a Continuation Application of U.S. Ser. No. 13/020,077 filed Feb. 3, 2011, which is a Continuation Application of U.S. Ser. No. 11/510,682 filed Aug. 25, 2006, now U.S. Pat. No. 8,003,630 issued Aug. 23, 2011, which is a Continuation of International Application No. PCT/US05/05268 filed Feb. 21, 2005 which claims priority to Ser. No. 60/548,021 filed Feb. 26, 2004, herein incorporated by reference in their entirety.

FIELD OF THE INVENTION

The invention relates generally to therapeutic formulations for use in the treatment of neoplasias. More specifically, the invention relates to pharmaceutical formulations comprised of chemotherapeutic agents and biotherapeutic agents for treating neoplasias. Methods for treating neoplasias by administering combinatorial formulations of neoplasia-treating agents, such as chemotherapeutic and/or radiation, along with biotherapeutic agents are also disclosed.

DESCRIPTION OF RELATED ART

Cancer is the second leading cause of death in the United States, surpassed only by heart disease. According to the American Cancer Society, approximately 556,000 Americans die from cancer each year-an average of more than 1,500 cancer deaths each day (Jemal, A. et al., CA Cancer J. Clin., 55, 10-30, 2005). Of the different cancers not including the skin cancers, lung cancer is the leading cause of cancer death for both men and women; breast cancer is the second leading cause of cancer death in women; prostate cancer is the second leading cause of cancer death in men and colorectal cancer is the third most frequently diagnosed form of cancer.

Pancreatic cancer is the most lethal human cancer with median survival for all stages of pancreatic cancer being less than 3-5 months from diagnosis. (CA Cancer J. Clin, 2004 54:8-20). The five-year survival rate is 3% or less. In spite of treatment efforts of surgery, radiation, and chemotherapy, the survival rate remains unchanged. (CA Cancer J. Clin, 2004) The incidence of pancreatic cancer is only 0.01% in the United States, but it is associated with the deaths of over 30,000 individuals each year, making this the most common in terms of cancer mortality. (Jemal, A. et al., CA Cancer J. Clin., 55, 10-30, 2005). Approximately 85-90% of symptomatic patients have advanced disease as a result of local infiltration or metastases at the time of diagnosis, and the prognosis for these individuals is extremely poor. (CA Cancer J. Clin 2005). Although some advances in treatment have been made that include surgery, chemotherapy, radiation therapy, immunotherapy, and hormonal therapy, pancreatic cancer remains a profound challenge in terms of prevention, diagnosis, prognosis and therapy.

At the time of diagnosis, up to around to around about 20% of pancreatic tumors can be removed by surgery. (Lancet 2004; 363:1049-57). When the tumor is confined to the pancreas but cannot be removed, a combination of radiotherapy and chemotherapy is usually performed. When the tumor has metastasized to other organs, such as the liver, chemotherapy alone is usually used. The standard chemotherapy agent is gemcitabine, but other drugs may be used. Gemcitabine essentially provides only palliative improvement in patients.

Head and neck cancer is the sixth ranking cancer in the world, and the third most common neoplasia in developing nations. In the United States, the incidence of cancer of the aerodigestive tract accounts for approximately 40,000 new cases each year, with over 11,000 fatalities recorded annually (Jemal, A. et al., CA Cancer J. Clin., 55, 10-30, 2005). More than 90% of head and neck cancers are squamous cell carcinomas (SCCHN), with the oral cavity and pharynx being the most common sites for SCCHN, followed by the larynx. Surgery, radiotherapy and chemotherapy, and combinations thereof, are all considered for treatment. Unfortunately, there is over a 50% chance of recurrence of SCCHN within two years, and the five-year survival is approximately 50% for all sites and stages. Moreover, in the last twenty-five years, the five-year survival of patients with SCCHN has not changed appreciably (Jemal, A. et al., CA Cancer J. Clin., 55, 10-30, 2005).

Peptide growth factors and their receptors have been implicated in SCCHN and pancreatic cancer, as well as in a number of other cancers (Sugerman, P. B. et al., Oral Dis., 1, 172-188, 1995). Some of the peptides found to be expressed in pancreatic cancer and SCCHN include epidermal growth factor (EGF), transforming growth factors $\alpha$ and $\beta$, basic fibroblast growth factor (bFGF), insulin-like growth factor (IGF), platelet derived growth factor (PDGF), and keratinocyte growth factor (KGF).

One group of peptides, the endogenous opioids, are believed to be important in the growth of normal, neoplastic, renewing and healing tissues, as well as in prokaryotes and eukaryotes (Zagon, I. S. et al., In: Cytokines: Stress and Immunity. Plotnikoff N P et al., (eds). CRC Press, Boca Raton, Fla., pp. 245-260, 1999). Met-enkephalin, an endogenous opioid peptide, is directly involved in growth processes, and serves as a negative regulator in a wide variety of cells and tissues (Zagon, I. S. et al., In: Receptors in the Developing Nervous System. Vol. 1. Zagon, I. S. and McLaughlin, P. J. (eds). Chapman and Hall, London, pp. 39-62, 1993). In view of its function (growth) and distribution (neural and non-neural), the peptide has been termed opioid growth factor (OGF).

Cancer chemotherapeutic agents are used for their lethal action to cancer cells. Unfortunately, few such drugs differentiate between a cancer cell and other proliferating cells. Chemotherapy generally requires use of several agents concurrently or in planned sequence. Combining more than one agent in a chemotherapeutic treatment protocol allows for: (1) the largest possible dose of drugs; (2) drugs that work by different mechanisms; (3) drugs having different toxicities; and (4) the reduced development of resistance.

Chemotherapeutic agents mainly affect cells that are undergoing division or DNA synthesis, thus slow growing malignant cells, such as lung cancer or colorectal cancer, are often unresponsive. Furthermore, most chemotherapeutic agents have a narrow therapeutic index. Common adverse effects of chemotherapy include vomiting, stomatitis, and alopecia. Toxicity of the chemotherapeutic agents is often the result of their effect on rapidly proliferating cells, which are vulnerable to the toxic effects of the agents, such as bone marrow or from cells harbored from detection (immunosuppression), gastrointestinal tract (mucosal ulceration), skin and hair (dermatitis and alopecia).

Many potent cytotoxic agents act at specific phases of the cell cycle (cell cycle dependent) and have activity only against cells in the process of division, thus acting specifically on processes such as DNA synthesis, transcription, or mitotic spindle function. Other agents are cell cycle independent. Susceptibility to cytotoxic treatment, therefore, may vary at different stages of the cell life cycle, with only those cells in a specific phase of the cell cycle being killed. Because of this cell cycle specificity, treatment with cytotoxic agents needs to be prolonged or repeated in order to allow cells to enter the sensitive phase. Non-cell-cycle-specific agents may act at any stage of the cell cycle; however, the cytotoxic effects are still dependent on cell proliferation. Cytotoxic agents thus kill a fixed fraction of tumor cells, the fraction being proportionate to the dose of the drug treatment.

Numerous neoplasia-treating agents are currently in use today, including any chemotherapeutic agents, and biotherapeutic agents as well as radiation therapy. There are numerous types of chemotherapeutic agents, including alkylating agents, nitrosoureas, antimetabolites, antitumor antibiotics, mitotic inhibitors, corticosteroid hormones, sex hormones, immunotherapy or others such as L-asparaginase and tretinoin. Some are briefly discussed below.

A widely used current chemotherapeutic agent is gemcitabine. Gemcitabine is a pyrimidine analogue that belongs to a general group of chemotherapy drugs known as antimetabolites and that also acts as a radiation-sensitizing agent. Gemcitabine exhibits cell phase specificity, primarily killing cells undergoing DNA synthesis, i.e., the S-phase, and also blocks the progression of cells through the $G_1$/S-phase boundary.

Gemcitabine is an approved chemotherapeutic agent for a wide range of tumors that include, but are not limited to, pancreatic and colorectal carcinoma. The efficacy of gemcitabine is marginal, however, and life expectancy is rarely extended, particularly for pancreatic cancer patients. Side effects of gemcitabine administration are relatively mild when compared to other chemotherapeutic agents, consisting of myelosuppression with increased risk of infection, decreased platelet count with increased risk of bleeding, nausea, vomiting, increased liver function blood tests and fatigue. Gemcitabine, in general, however, has replaced other therapies because of its less toxic effects on the patient, and hence, a better quality of life.

The platin family of chemotherapeutics consists primarily of cisplatin and carboplatin. Cisplatin is an inorganic platinum complex that disrupts the DNA helix by forming intra- and interstrand cross-links. Cisplatin also reacts, however, with nucleophils of other tissues, causing toxic effects on the kidney and on the eight cranial nerve (which is responsible for causing intense nausea and vomiting). Other side effects include renal toxicity, ototoxicity manifested by tinnitus and hearing loss, and mild to moderate myelosuppression. Carboplatin differs from cisplatin mainly with respect to side effects. Myelosuppression is the dose-limiting toxicity for carboplatin with very little of the renal, neurologic, or ototoxicities that are encountered with cisplatin.

Paclitaxel is a natural, although quite toxic, substance derived from the yew tree that is chemically altered to produce a powerful anti microtubule chemotherapeutic agent indicated for the treatment of metastatic breast cancer, metastatic ovarian cancer, and Kaposi's sarcoma. Paclitaxel also has been used to treat SCCHN, non-small cell lung cancer, small cell lung cancer and bladder cancer. Side effects commonly encountered with paclitaxel administration include nausea and vomiting, loss of appetite, change in taste, thinned or brittle hair, pain in the joints of the arms or legs lasting 2-3 days, changes in the color of nails and tingling in hands or toes.

The chemotherapeutic agent, 5 fluorouracil (5-FU), has been one of the major antimetabolites used in a variety of solid cancers since the 1960s. 5-FU prevents cells from making DNA and RNA by interfering with the synthesis of nucleic acids, thus disrupting the growth of cancer cells. 5-FU is used alone or in combination in the adjuvant treatment of breast, colon, gastrointestinal and head or neck cancer. 5-FU also is used as a palliative therapy of inoperable malignant neoplasms, such as of the gastrointestinal tract, breast, liver, genitourinary system and pancreas. 5-FU has many common side effects, including myelosuppression with increased risk of infection and bleeding, darkening of skin and nail beds, nausea, vomiting, sores in mouth or on the lips, thinning hair, diarrhea, brittle nails, increased sensitivity to the sun and dry, flaky skin.

There exists a need, therefore, for a therapeutic formulation to treat various types of cancer and, in particular, pancreatic cancer and SCCHN, which demonstrates enhanced efficacy and survival rates with reduced concomitant side effects and toxicity commonly encountered with chemotherapeutic agents.

SUMMARY OF THE INVENTION

The present invention provides for the first time a carcinotherapeutic pharmaceutical composition and/or treatment method for treating neoplasias in an animal or human comprised of a carrier and therapeutically effective amounts of at least one neoplasia treating agent, such as chemotherapeutic agent or radiation therapy (agent) and the biotherapeutic endogenous pentapeptide Met-enkephalin, referred to as opioid growth factor (OGF). As used herein, a carcinotherapeutic composition refers to a composition that includes both chemotherapeutic and biotherapeutic agents for the treatment of all neoplasias, including but not limited to true carcinomas but also other cancers such as sarcomas, melanomas, etc.

As used herein the term "OGF or Met-enkephalin" shall be interpreted to include all modifications, substitutions, truncations or derivatives of OGF or Met-enkephalin which retain the ability to interact with the OGF receptor in a similar fashion to OGF as described herein. This also includes synthetic or any other compound which mimics the biological activity of OGF in its interaction with the OGF receptor.

The present invention also provides a method of treating neoplasias in an animal or human in need of such treatment, comprising the administration to the animal or human therapeutically effective amounts of each of at least one neoplasia-treating agent and OGF. A wide variety of neoplasia-treating agents have been shown to be effective when used in combination with OGF including anti-metabolites, cytosine analogs, cross linking agents and the like. The effects of OGF are mediated through the OGFr and thus it is postulated that any chemotherapeutic agent, or biotherapeutic agent, will have similar effects, including radiation therapy. Some examples of chemotherapeutic agents that can be used in accordance with the invention include without limitation, Neoplasia-treating agents can include any chemotherapeutic agents as well as radiation therapy. There are numerous types of chemotherapeutic agents, any of which may be used according to the invention, include but are not limited to alkylating agents, nitrosoureas, antimetabolites, antitumor antibiotics, mitotic inhibitors, corticosteroid hormones, sex hormones, immunotherapy or others such as L-asparaginase and tretinoin.

The combination of the biotherapeutic OGF and neoplasia treating agent is in most cases at least additive which will allow for a reduction in toxicity of the treatment as a similar result may be achieved with a lower dose of the neoplasia treating agent. This is important as many of these agents are highly toxic and should be used in as small dose as possible. In at least one protocol the reduction in toxicity was seen in addition to the additive nature of the agents. Often the result of the combination is a synergistic effect, i.e. the reduction in cells is greater than the sum of each of the agents alone. The effects of the OGF are blocked by naloxone indicating that the OGF effect is entirely mediated by the OGFr.

In yet another embodiment the OGFr may be introduced to tumor cells in a suicide type treatment protocol where tumor or neoplasia cells will be sensitized to the anti-neoplastic treatment by the introduction of additional OGFr receptors to the cells so that OGF may interact with as many cells as possible in mediating and potentiating the effect of the therapy.

Neoplasias that can be treated according to the method of the present invention include any neoplasia cell that has an OGFr, this can include without limitation, pancreatic cancer, squamous cell cancer of the head and neck, breast cancer, colorectal cancer, renal cancer, brain cancer, prostate cancer, bladder cancer, bone or joint cancer, uterine cancer, cervical cancer, endometrial cancer, multiple myeloma, Hodgkin's disease, non-Hodgkin's lymphoma, melanoma, leukemias, lung cancer, ovarian cancer, gastrointestinal cancer, Kaposi's sarcoma, liver cancer, pharyngeal cancer or laryngeal cancer.

The effective therapeutic amount of OGF that can be administered according to the composition in an intravenous protocol for example between about 20 to 1000 µg/kg body weight per day, preferably about 100 to 400 µg/kg body weight. OGF may be administered at least once a week, and as frequently as multiple times daily, throughout the entire treatment period depending on the route of administration. OGF is non-toxic and may be administered in accordance with essentially any effective dose. The mode of administration, i.e. intravenous, subcutaneous, etc. may also alter the effective dose and timetable of drug administration, but such can be determined through routine experimentation. The antineoplastic agent may be administered sequentially, or simultaneously with the administration of OGF, at least one neoplasia treating agent is administered to an animal or human in therapeutically effective amounts of, for example, between about 20 to 3000 mg/m$^2$, preferably about 100 to 1000 mg/m$^2$, over a period of between about 10 to 60 minutes, and preferably about 30 minutes, at least once a week for about three to ten weeks, preferably seven weeks. After one to three weeks, preferably one week, of rest, the chemotherapeutic agent is administered over a period of between about 10 to 60 minutes, preferably about 30 minutes, for about one to five weeks, preferably three weeks. Administration of the chemotherapeutic agent can repeat every two to eight weeks, preferably four weeks, in the absence of disease progression or unacceptable toxicity. Subcutaneous or implant delivery will also be effective.

In another embodiment of the present invention, OGF is administered in an effective dose of about 20 to 1000 µg/kg body weight, preferably about 100 to 400 µg/kg body weight at least three times a week, preferably daily, during the course of radiation therapy.

In yet another embodiment of the present invention, OGF is administered in an effective dose of about 20 to 1000 µg/kg body weight, preferably about 100 to 400 µg/kg body weight at least three times a week, preferably daily, with chemotherapy during the course of radiation therapy.

The route of administration of the antineoplastic agent(s) and opioid growth factor includes, without limitation, parenteral administration, namely intravenous, intramuscular or intraperitoneal, subcutaneous, implanted osmotic pump or transdermal patch.

DETAILED DESCRIPTION OF THE INVENTION

Figure 1:
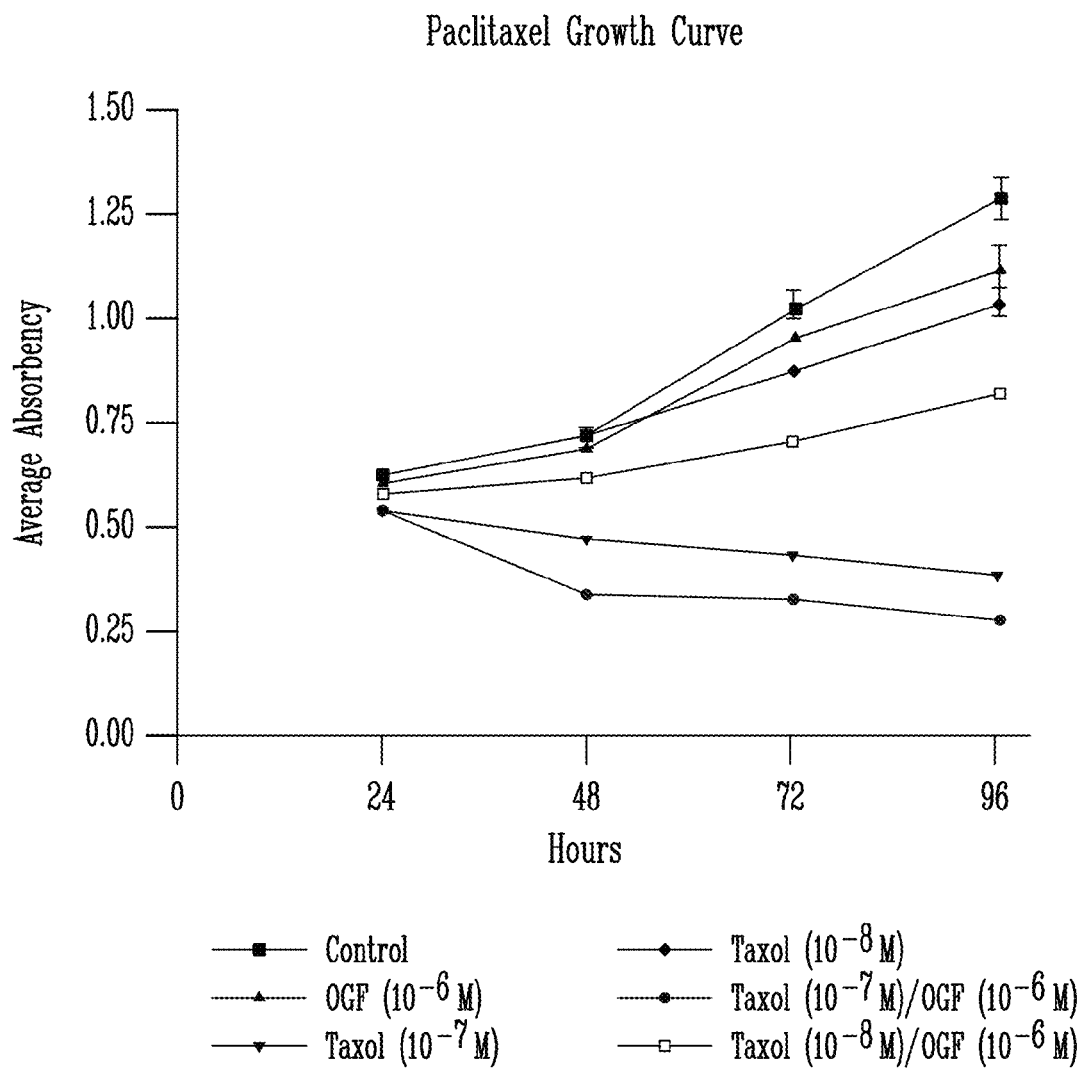
FIG. 1 is a graph representing a 96-hour growth curve for SCC-1 cells being treated with paclitaxel (Taxol) and/or OGF. Each data point represents the average absorbency for 10 wells±S.E.M. Significance values for each timepoint can be found on Table 1.

The present invention provides for the first time a carcinotherapeutic pharmaceutical composition and method for treating neoplasias in an animal or human comprised of a carrier and therapeutically effective amounts of at least one chemotherapeutic agent and the biotherapeutic endogenous pentapeptide Met-enkephalin, referred to as opioid growth factor (OGF).

The present invention also provides a method of treating neoplasias in an animal or human in need of such treatment, comprising the administration to the animal or human therapeutically effective amounts of each of at least one neoplasia-treating agent and OGF. Neoplasia-treating agents can include any biotherapeutic agents, radiopharmaceuticals, and chemotherapeutic agents as well as radiation therapy. There are numerous types of chemotherapeutic agents, any of which may be used according to the invention. These include alkylating agents, nitrosoureas, antimetabolites, antitumor antibiotics, mitotic inhibitors, corticosteroid hormones, sex hormones, immunotherapy or others such as L-asparaginase and tretinoin. Examples of biotherapeutic agents include but are not limited to interferon, interleukin, tumor derived activated cells. Radionuclides such as Iodine$^{125}$, are also pertinent as well as radiation therapy from gamma or x-rays.

Chemotherapeutic alkylating agents work directly on DNA to prevent the cancer cell from reproducing. As a class of drugs, these agents are not phase-specific (in other words, they work in all phases of the cell cycle). These drugs are active against chronic leukemias, non-Hodgkin's lymphoma, Hodgkin's disease, multiple myeloma, and certain cancers of the lung, breast, and ovary. Examples of alkylating agents include busulfan, cisplatin, carboplatin, chlorambucil, cyclophosphamide, ifosfamide, dacarbazine (DTIC), mechlorethamine (nitrogen mustard), and melphalan. Nitrosoureas act in a similar way to alkylating agents. They interfere with enzymes that help repair DNA. These agents are able to travel to the brain so they are used to treat brain tumors as well as non-Hodgkin's lymphomas, multiple myeloma, and malignant melanoma. Examples of nitrosoureas include carmustine (BCNU) and lomustine (CCNU).

Antimetabolites are a class of drugs that interfere with DNA and RNA growth. These agents work during the S phase and are used to treat chronic leukemias as well as tumors of the breast, ovary, and the gastrointestinal tract. Examples of antimetabolites include 5-fluorouracil, capecitabine, methotrexate, gemcitabine, cytarabine (ara-C), and fludarabine.

Antitumor antibiotics interfere with DNA by stopping enzymes and mitosis or altering the membranes that surround cells. (They are not the same as antibiotics used to treat infections.) These agents work in all phases of the cell cycle. Thus, they are widely used for a variety of cancers. Examples of antitumor antibiotics include dactinomycin, daunorubicin, doxorubicin (Adriamycin), idarubicin, and mitoxantrone.

Mitotic inhibitors are plant alkaloids and other compounds derived from natural products. They can inhibit, or stop, mitosis or inhibit enzymes for making proteins needed for reproduction of the cell. These work during the M phase of the cell cycle. Examples of mitotic inhibitors include paclitaxel, docetaxel, etoposide (VP-16), vinblastine, vincristine, and vinorelbine.

Steroids are natural hormones and hormone-like drugs that are useful in treating some types of cancer (lymphoma, leukemias, and multiple myeloma) as well as other illnesses. When these drugs are used to kill cancer cells or slow their growth, they are considered chemotherapy drugs. They are often combined with other types of chemotherapy drugs to increase their effectiveness. Examples include prednisone and dexamethasone.

Sex hormones, or hormone-like drugs, alter the action or production of female or male hormones. They are used to slow the growth of breast, prostate, and endometrial (lining of the uterus) cancers, which normally grow in response to hormone levels in the body. These hormones do not work in the same ways as standard chemotherapy drugs. Examples include anti-estrogens (tamoxifen, fulvestrant), aromatase inhibitors (anastrozole, letrozole), progestins (megestrol acetate), anti-androgens (bicalutamide, flutamide), and LHRH agonists (leuprolide, goserelin).

Some drugs are given to people with cancer to stimulate their immune systems to more effectively recognize and attack cancer cells. These drugs offer a unique method of treatment, and are often considered to be separate from "chemotherapy."

Some chemotherapy drugs act in slightly different ways and do not fit into any of the other categories. Examples include such drugs as L-asparaginase and tretinoin.

The combination therapy has been exemplified herein with the alkylating agent, carboplatin, the antimetabolite 5-FU, and gemcitabine, and a mitotic inhibitor Paclitaxel.

Neoplasias that can be treated according to the method of the present invention include, without limitation, pancreatic cancer, squamous cell cancer of the head and neck, breast cancer, colorectal cancer, renal cancer, brain cancer, prostate cancer, bladder cancer, bone or joint cancer, uterine cancer, cervical cancer, endometrial cancer, multiple myeloma, Hodgkin's disease, non-Hodgkin's lymphoma, melanoma, leukemias, lung cancer, ovarian cancer, gastrointestinal cancer, Kaposi's sarcoma, liver cancer, pharyngeal cancer or laryngeal cancer.

The effective therapeutic amount of OGF that can be administered according to the composition and method of the present invention for an intravenous therapy is between about 20 to 1000 µg/kg body weight per day, preferably about 100 to 400 µg/kg body weight per day. OGF may be administered at least three times a week, and as frequently as once daily, throughout the entire treatment period. OGF is safe and non-toxic and may be administered in essentially any amount necessary to be effective. The route of administration (intravenous, subcutaneous, etc) may affect the amounts than can be given however this is all determined thorough routine experimentation. Sequentially or simultaneously with the administration of OGF, at least one chemotherapeutic agent is administered to an animal or human in therapeutically effective amounts of between about 20 to 3000 mg/m$^2$, preferably about 100 to 1000 mg/m$^2$, over a period of between about 10 to 60 minutes, and preferably about 30 minutes, at least once a week for about three to ten weeks, preferably seven weeks. After one to three weeks, preferably one week, of rest, the chemotherapeutic agent is administered over a period of between about 10-60 minutes, preferably about 30 minutes, for about one to five weeks, preferably three weeks. Administration of the chemotherapeutic agent can repeat every two to eight weeks, preferably four weeks, in the absence of disease progression or unacceptable toxicity.

In another embodiment of the present invention, OGF is administered in an effective dose of about 20 to 1000 µg/kg body weight, preferably about 100 to 400 µg/kg body weight at least three times a week, preferably daily, during the course of radiation therapy. The route of administration of the chemotherapeutic agent(s) and opioid growth factor include, without limitation, parenteral administration, namely intravenous, intramuscular or intraperitoneal, subcutaneous, implanted slow release osmotic minipump or transdermal patch.

The OGF pentapeptide is a constitutively expressed autocrine inhibitory growth factor in a wide variety of cells and tissues both in vivo and in vitro, and under normal (e.g., homeostatic development) and abnormal (e.g., cancer, wound healing) conditions. The action of OGF in vitro is stereospecific, reversible, non-cytotoxic, independent of serum and occurs at physiologically relevant concentrations.

In particular, in a using a human pancreatic cancer cell line, The combination of OGF and gemcitabine reduced cell number from control levels by 26% to 46% within 48 hr, and resulted in a growth inhibition greater than that of the individual compounds. The combination of OGF and gemcitabine also repressed the growth of a second pancreatic cancer cell line. In vivo, addition of OGF to gemcitabine therapy in nude mice reduces tumor volume more than either compound alone. Tumor weight and tumor volume were reduced from control levels by 36% to 85% in the OGF and/or gemcitabine groups on day 45 and the group of mice exposed to a combination of OGF and gemcitabine had decreases in tumor size of 62% to 77% from the OGF or the gemcitabine alone groups.

OGF in combination with 5-fluorouracil also depressed cell growth more than either agent alone in a pancreatic cancer cell line.

Similar effects were also observed in squamous cancer cell lines. The combination therapy of paclitaxel and OGF in several lines resulted in a reduction in cell numbers greater than of either compound alone. In vivo the reduction in tumor volume and weight was synergistic and it appeared that the OGF reduced the toxicity of paclitaxel resulting in a higher survival rate.

Carboplatin also resulted in an additive effect reducing squamous cancer cell number by 14-27%.

As can be seen the benefits of combination therapy of OGF with chromotherapeutic agents results in a greater reduction in cell number than either compound alone, is often synergistic and can also reduce toxicity of the chemotherapeutic agent. This was seen in at least two very different types of cancer cells in multiple cell lines with different chemotherapeutic agents and both in vitro and in vivo.

It is believed, without being bound by any particular theory, that OGF may confer protective effects against the cytotoxicity encountered with some chemotherapeutic agents, such as paclitaxel.

Both OGF and the OGFr have been detected in epithelium of rodent and human tongue, skin, gastrointestinal tract, and cornea. It has been shown that both OGF and the OGFr are present in human tumors when obtained at the time of surgical resection. Additionally, DNA synthesis of epithelial cells in mammalian tongue, epidermis, cornea and esophagus has been shown to be regulated by OGF, and does so in a receptor-mediated fashion.

OGF has been found to be associated with a reduction in cell number, suggesting that a target of OGF is cell replication. Using human pancreatic cancer cells in tissue culture, and administering sufficient quantities of OGF to elicit responses that presumably are similar to those occurring with endogenous OGF, it has been confirmed that OGF represses cell accumulation and manifests this activity within twenty-four hours after OGF exposure. It is believed, without being bound by any particular theory, that OGF significantly reduces DNA synthesis and suppresses mitosis, thus modulating cellular generation.

The cell cycle is composed of five phases: the presynthetic or $G_1$ phase; synthesis of DNA or S phase; post synthetic or $G_2$ phase (this phase contains double complement of DNA dividing into two daughter $G_1$ cells); and mitosis or M phase. Newly divided cells may reenter the cycle or go into a resting or $G_0$ phase. OGF has been shown to alter the proportion of cells in phases of the cell cycle so that within about two hours there is a marked increase in the number of cells in $G_0/G_1$ and a compensatory decrease in cells in the S and $G_2/M$ phases. Moreover, OGF appears to increase dramatically the length of the $G_0/G_1$ phase, thus accounting for the notable increase in doubling time of the total cell cycle that is observed. It is believed, without being bound by the theory, that treatment with OGF, either prior to or during radiation therapy, sensitizes the effect of radiation on tumor cells via the ability of OGF to accumulate cancer cells in the $G_0/G_1$ phase of the cell cycle, where they are most vulnerable to radiation.

Gemcitabine is a pyrimidine analogue that belongs to a general group of chemotherapy drugs known as antimetabolites that also acts as a radiation-sensitizing agent. Gemcitabine exhibits cell phase specificity, primarily killing cells undergoing DNA synthesis, i.e., the S-phase, and also blocks the progression of cells through the $G_1/S$-phase boundary. Gemcitabine is metabolized intracellularly by nucleoside kinases to the active gemcitabine diphosphate (dFdCDP) and triphosphate (dFdCTP) nucleosides. The cytotoxic effect of gemcitabine is attributed to a combination of two actions of the diphosphate and the triphosphate nucleosides, which leads to inhibition of DNA synthesis. First, gemcitabine diphosphate inhibits ribonucleotide reductase, which is responsible for catalyzing the reactions that generate the deoxynucleoside triphosphates for DNA synthesis Inhibition of this enzyme by the diphosphate nucleoside causes a reduction in the concentrations of deoxynucleotide, including dCTP. Second, gemcitabine triphosphate competes with dCTP for incorporation into DNA. The reduction in the intracellular concentrations of dCTP (by the action of the diphosphate) enhances the incorporation of gemcitabine triphosphate into DNA (self-potentiation). After the gemcitabine nucleotide is incorporated into DNA, only one additional nucleotide is added to the growing DNA strands. After this addition, there is inhibition of further DNA synthesis. DNA polymerase epsilon is unable to remove the gemcitabine nucleotide and repair the growing DNA strands (masked chain termination). In lymphoblastoid cells, gemcitabine induces internucleosomal DNA fragmentation, one of the characteristics of programmed cell death.

Paclitaxel, also known as Taxol, is derived from the bark and leaves of the Pacific yew (another source is from the needles of a European yew). Paclitaxel is very lipid soluble and must be administered intravenously soon after preparation. Paclitaxel is an antimicrotubule agent that promotes the assembly of microtubulin dimers and stabilizes microtubules by preventing depolymerization. This stability results in the inhibition of the normal dynamic reorganization of the microtubule network that is essential for vital interphase and mitotic cellular functions. In addition, paclitaxel induces abnormal arrays or "bundles" of microtubules throughout the cell cycle and multiple asters of microtubules during mitosis. Paclitaxel side effects include transient bradycardia, peripheral neuropathy, nausea, vomiting, diarrhea, neutropenia, thrombocytosis, bronchospasm, urticaria, angioedema, alopecia and myalgias. Premedication with dexamethasone, diphenhydramine, and H2 antagonists are used to reduce hyposensitivity reactions.

Carboplatin and cisplatin belong to the platin family of chemotherapeutic agents, inorganic platinum complexes that disrupt the DNA helix by forming intra- and interstrand crosslinks. Cisplatin in particular reacts with nucleophils of other tissues, hence its toxic effect on the kidney, the eight cranial nerve, and the intense emesis.

Both carboplatin and cisplatin are concentrated in the kidney, liver, intestines and testes, but they do not cross the blood brain barrier. They are usually used with other agents in metastatic testicular, ovarian carcinoma, and advanced bladder cancer. Side effects are commonly encountered with cisplatin administration, and include renal toxicity, ototoxicity manifested by tinnitus and hearing loss, marked nausea and vomiting. Additionally, mild to moderate myelosuppression may develop. Carboplatin differs from cisplatin mainly in side effects, as myelosuppression is the dose-limiting toxicity for carboplatin with very little of renal, neurologic, or ototoxicity.

5-FU as a single agent has an activity superior to that of any other single agent in the treatment of carcinomas of the colon and rectum. It is used primarily for slowly growing solid tumors, such as carcinomas of the breast and the gastrointestinal tract. The mean response rate is still low, however, being less than 20%. Inactive as such, fluorouracil must be converted to the 5'-monophosphate nucleotide where it may inactivate enzymes essential to synthesize thymidylate, or where it acts within a complex pathway. 5-FU is incorporated into RNA and inhibits DNA synthesis. 5-FU is converted into the active 5-fluoro-deoxyuridine monophosphate (FdUMP) by a variety of different metabolic pathways. The drug acts by inhibiting the enzyme thymidylate kinase which results in reduced formation of thymidine and thus of DNA. Fluorouracil, as FdUMP, is also incorporated into RNA, which results in fluoridation of the RNA.

The effect of 5-FU on living cells is limited mainly to those in the proliferative phase. However, while cells in the $G_2$ and S phases are most affected there may be effects at any stage of the cell cycle. 5-FU is metabolized primarily in the liver, with only 10% of the drug appearing unchanged in urine. 5-FU can enter cerebrospinal fluid. Resistance to 5-FU develops because the cells lose their ability to convert 5-FU to its active form. Common side effects are often delayed. Stomatitis that ulcerates is an early sign of toxicity, and myelosuppression (leukopenia) usually occurs between nine and fourteen days of therapy. Other side effects include alopecia, dermatitis, and atrophy of the skin.

It is believed, without being bound by any particular theory, that the carcinotherapeutic composition of the present invention, i.e., combining at least one chemotherapeutic agent with the biotherapeutic agent, OGF, exerts its potent inhibitory effect on cancer cell growth by the ability of OGF to accumulate cells in the $G_0/G_1$ phase, where the cells are vulnerable to the cytotoxic effects of a chemotherapeutic agent, thus greatly enhancing the number of cells killed by the chemotherapeutic agent. A lowered effective dose of the chemotherapeutic agent is needed, therefore, to produce a significantly greater growth inhibition than what would occur without the presence of OGF.

The following non-limiting examples describe in more detail the effects of administering OGF in combination with gemcitabine, paclitaxel, carboplatin and 5-FU on a human squamous cell carcinoma cell line (SCC-1 cell line) and on a human pancreatic cancer cell line (MiaPaCa-2 cell line).

EXAMPLE 1

Combination Therapies on the SCC-1 Cell Line

1. Growth Curves-SCC-1 Cell Lines

The growth of cells as represented by absorbency taken at 450 nm from the cell proliferation assay plotted against time was the standard format for presenting the effects of different drugs on SCC-1 or MiaPaCa-2 cells. Cells were counted using a standard MTT assay. In general, each data point represents the average absorbency taken from 10 wells/treatment; error bars represent the S.E.M.

a. Paclitaxel Treatment

The results illustrated in FIG. 1 and Table 1 examine the addition of paclitaxel (Taxol) and/or OGF to SCC-1 cells. Throughout the 4-day growth curve, statistical analysis (ANOVA) revealed that OGF ($10^{-6}$ M) alone inhibited growth at 48, 72 and 96 hours decreasing cell number from control levels by 11.9, 6.7, and 12.7%, respectively. Paclitaxel at a concentration of $10^{-7}$M inhibited cell growth at 24, 48, 72, and 96 hours decreasing cell number from controls by 14.2, 34.4, 58, and 70%, respectively. Paclitaxel at a concentration of 10-8 also inhibited growth at 72 and 96 hours with decreases in cell number relative to controls of 14.1 and 19.3%, respectively. When paclitaxel $10^{-7}$ was combined with OGF $10^{-6}$ M, growth inhibition was observed at 24, 48, 72, and 96 hours resulting in a decrease in cell number relative to controls of 13.5, 52.6, 68.4, and 78.4%, respectively. When paclitaxel $10^{-8}$M was combined with OGF $10^{-6}$ M, cell growth inhibition was observed at 48, 72, and 96 hours with decreases in cell number relative to controls of 13.6, 30.6, and 36.3%, respectively. OGF in combination with paclitaxel $10^{-7}$ M was significantly more inhibitory than any drug alone at all timepoints (besides paclitaxel $10^{-7}$ M at 24 hours) with decreases in cell number ranging from 10.1-75.3%. OGF in combination with paclitaxel $10^{-8}$M was significantly more inhibitory than any drug alone at 48, 72, and 96 hours with decreases in cell number ranging from 10.4-27.1%.

b. Carboplatin Treatment

Figure 2:
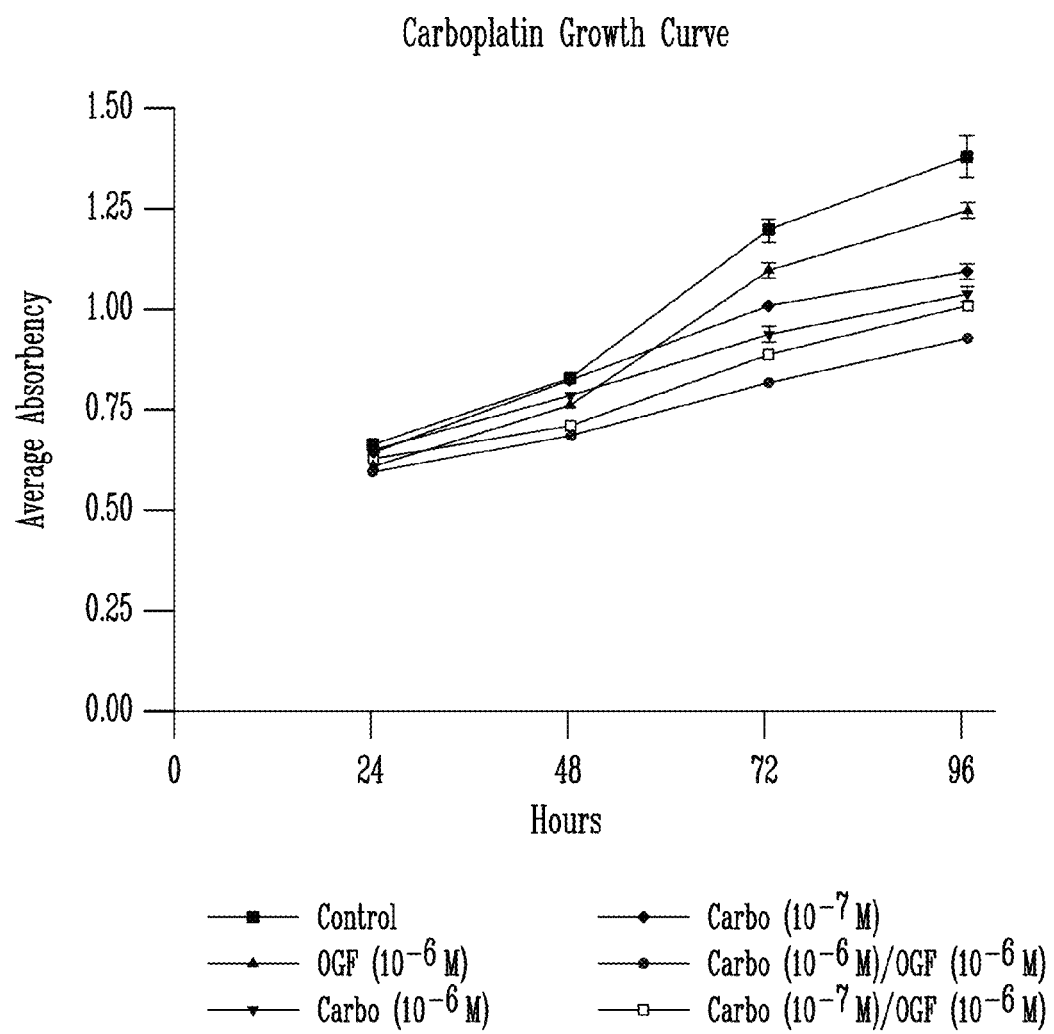
FIG. 2 is a graph representing a 96-hour growth curve for SCC-1 cells being supplemented with carboplatin and/or OGF. Each data point represents the average absorbency for 10 wells±S.E.M. Significance values for each timepoint can be found on Table2.

The results illustrated in FIG. 2 and Table 2 examine the addition of carboplatin and/or OGF to SCC-1 cells. Throughout the 4-day period of treatment, statistical analysis (ANOVA) revealed that the OGF ($10^{-6}$ M) alone inhibited growth at 48, 72, and 96 hours with decreases in cell number relative to controls of 8.2, 8.4, and 9.7%, respectively. Carboplatin at a concentration of $10^{-6}$ M inhibited cell growth at 48, 72, and 96 hours decreasing cell number relative to controls by 5.3, 21.8, and 24.9%, respectively. Carboplatin at a concentration $10^{-7}$ M also inhibited growth at 72 and 96 hours decreasing cell number relative to controls by 18.7 and 21%, respectively. When carboplatin $10^{-6}$M was combined with OGF $10^{-6}$M, growth inhibition was observed at 24, 48, 72, and 96 hours resulting in decreases in cell number relative to controls of 10.3, 17.5, 32.2, and 33.3%, respectively. When carboplatin $10^{-7}$ M was combined with OGF $10^{-6}$ M, cell growth inhibition was observed at 48, 72, and 96 hours with decreases in cell number relative to controls of 14.1, 26.3, and 27.1%, respectively. OGF in combination with carboplatin $10^{-6}$M was significantly more inhibitory than any drug alone at 48, 72, and 96 hours with decreases in cell number ranging from 3.1-23.6%. OGF in combination with carboplatin $10^{-7}$ M was significantly more inhibitory than OGF alone at 48, 72, and 96 hours, carboplatin $10^{-6}$M at 48 and 72 hours, and carboplatin $10^{-7}$ at 48 and 72 hours with decreases in cell number ranging from 10.4-27.1% (Table 2).

c. Body Weights, Life-Span, and Gross Observation

Figure 4:
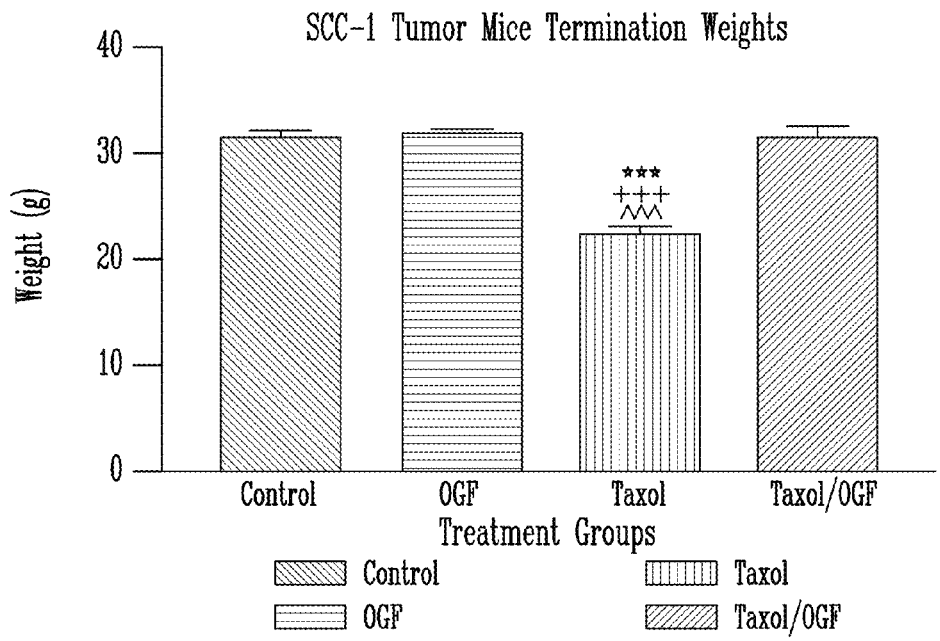
FIG. 4 shows the final termination weights for athymic nude mice inoculated with SCC-1 SCCHN cells. Bars represent the mean values for weight for the entire treatment group at the time of termination (Day 50). Significant from controls at p<001 (***), significant from OGF at p<0.001 (+++), and significant from Taxol/OGF at ρ<0.001 (^^^).

At the beginning of the trial, all mice weighed approximately 22-24 grams and mice gained roughly 2 to 4 grams every 5 days. However, by day 20 of the experiment, paclitaxel mice began to lose weight, weighing 11% less than controls ($p<0.05$). Continued weight loss was observed within the paclitaxel group until termination day or the death of the mice (see survival curve FIG. 5), on day 50 mice weighed 28% less ($p<0.001$) than controls, OGF, and paclitaxel/OGF treated mice (see FIG. 4).

Figure 5:
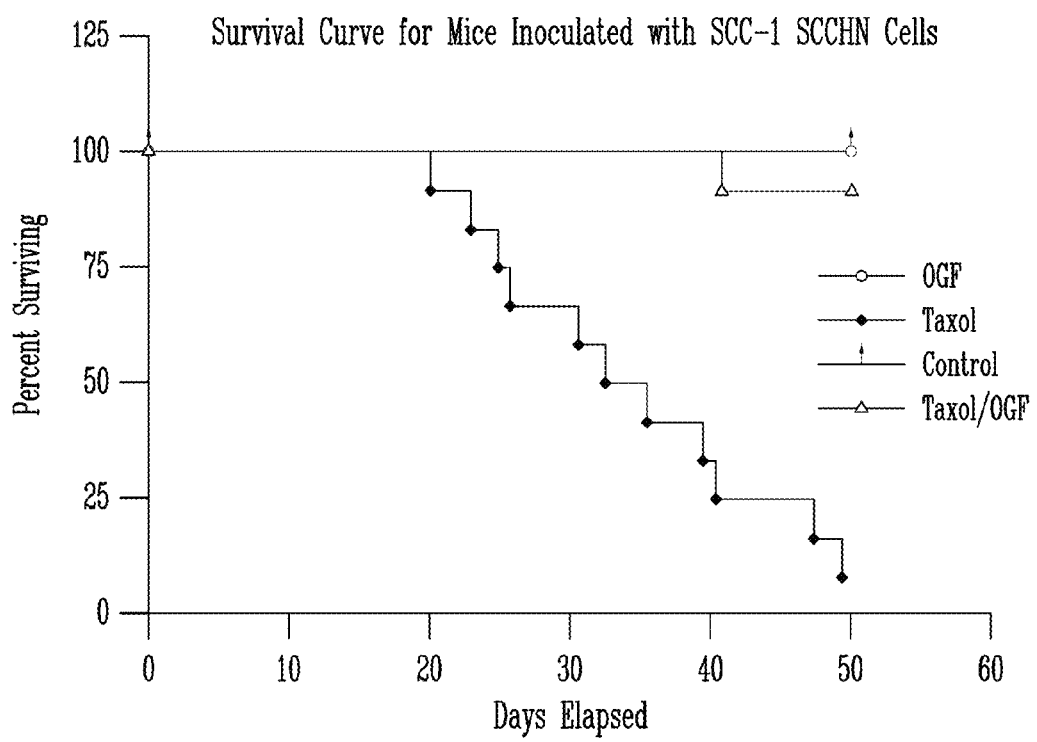
FIG. 5 shows a survival curve representing the percent of surviving mice in each of the four groups over the course of the 50-day study.
Figure 6:
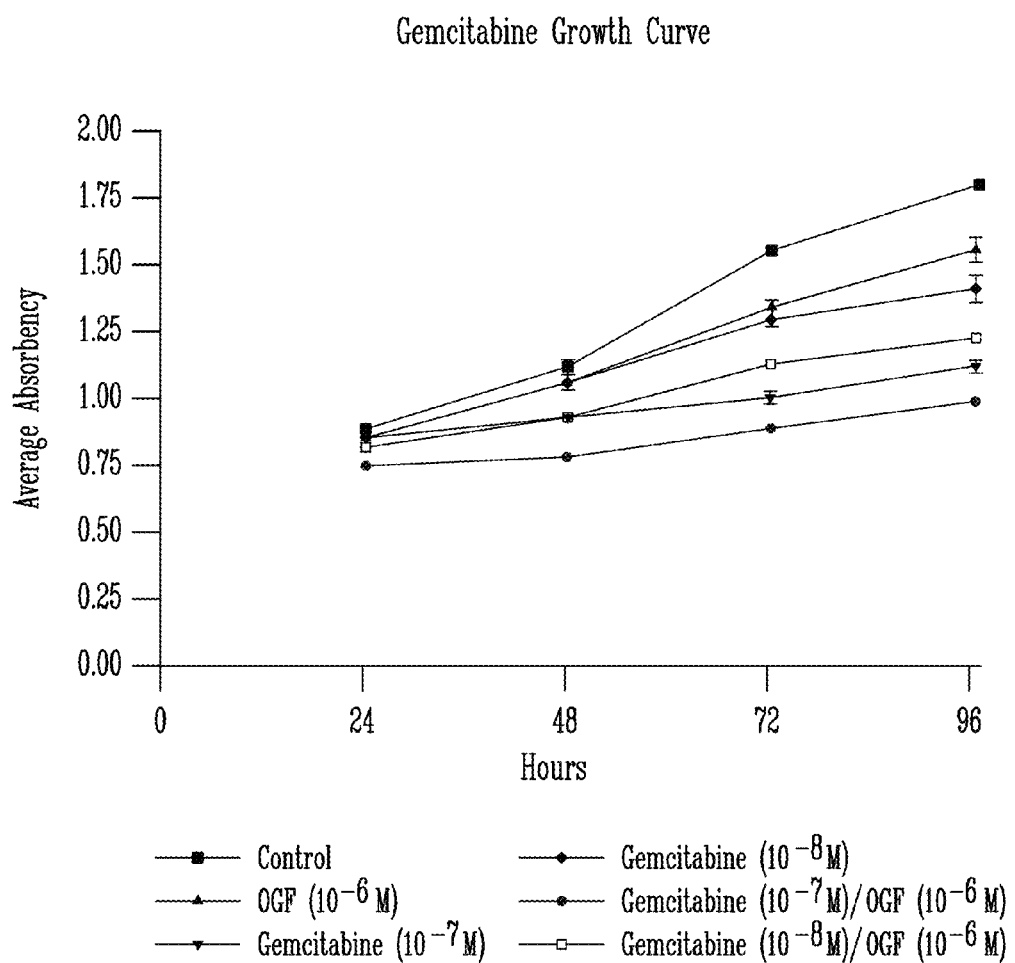
FIG. 6 is a graph representing a 96-hour growth curve for MiaPaCa-2 cells treated with gemcitabine and/or OGF. Each data point represents the average absorbency for 10 wells±S.E.M. Significance values for each timepoint can be found on Table 3.

Mice in the paclitaxel group began dying on day 19 (see FIG. 5). By day 40, 75% of the paclitaxel treated mice had died and no mouse in any other treatment group, including the paclitaxel/OGF group had perished. On termination day, only one mouse (8% of the group) was still alive. The average life span of the paclitaxel mice was 34.3±3.1 days and this was significantly ($p<0.001$) different from all other treatment groups. One mouse in the paclitaxel/OGF group died on day 40 but all remaining mice were still alive until termination day.

Due to the premature death of the paclitaxel mice, organs were harvested and fixed in formalin for histological analysis. Upon analysis, it was observed that premature death could have been attributed to distended abdomens with associated megacolon. The large intestine, cecum, and small bowel were all completely impacted with hardened stool. All other organ systems appeared normal.

EXAMPLE 2

SCC-1 Tumor Appearance and Growth

All mice that were injected with SCC-1 cells developed tumors. On day 13 after tumor cell inoculation, 75% of mice, 66% of paclitaxel treated mice, and 58% of paclitaxel/OGF treated mice had tumors. When examining latency to a visible tumor, control mice developed visible, but not measurable tumors within 7 days of tumor cell inoculation. Paclitaxel and paclitaxel/OGF mice also developed visible tumors within the same 1-week time frame while OGF mice developed tumors within 11 days, exhibiting an approximate 4-day delay in visible tumor development ($p<0.05$). The latency time for measurable (62.5 mm$^3$) tumors displayed an analogous pattern to the latency for visible tumors where control, paclitaxel, and paclitaxel/OGF groups had measurable tumors within 2 weeks of tumor cell inoculation while the OGF group developed measurable tumors within 17 days, although this difference was not significant from control values.

Figure 3:
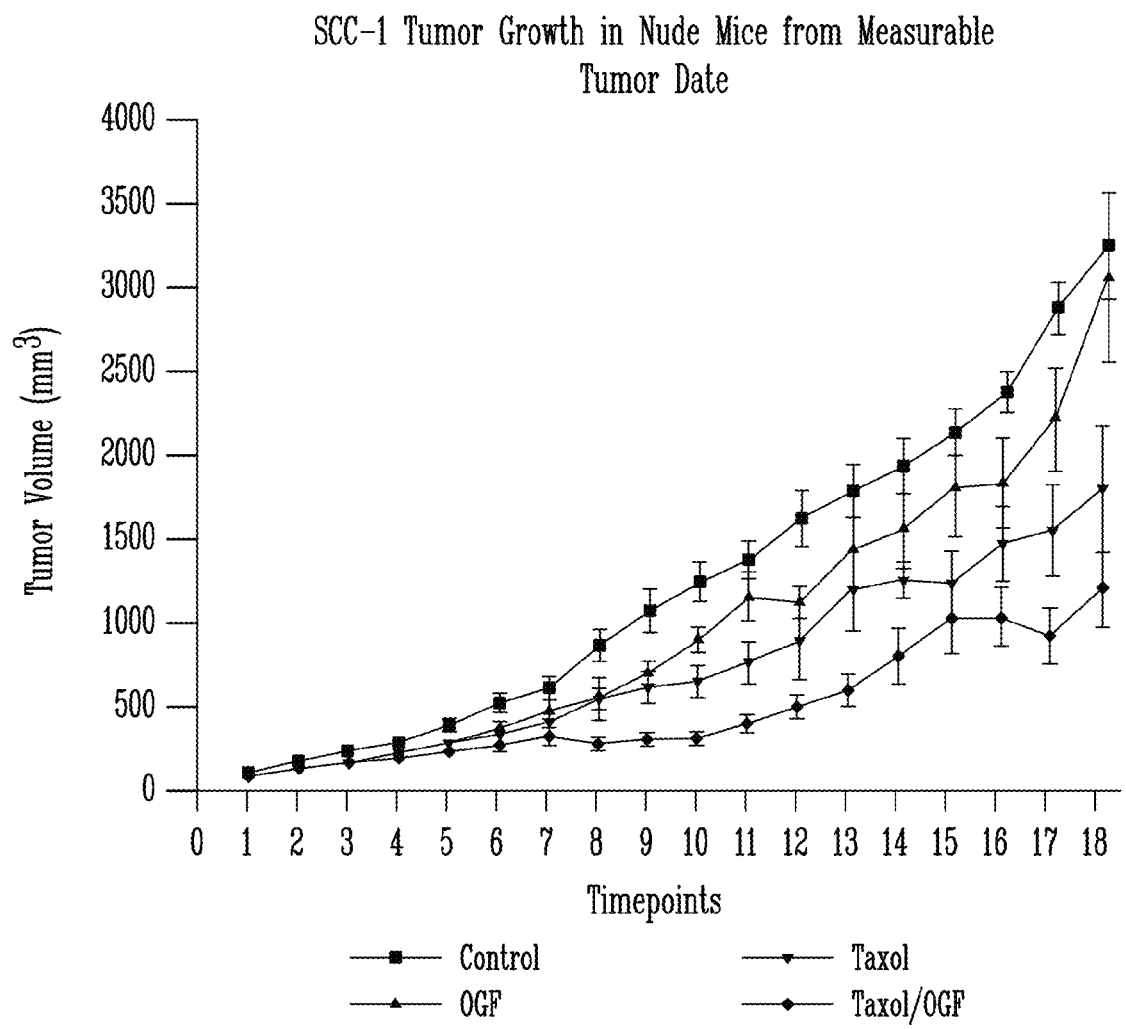
FIG. 3 shows the growth of SCC-1 SCCHN cells in athymic nude mice. Timepoint 1 signifies the first day that tumors became measurable in each treatment group. Tumor volumes were recorded every day and averages from 2 consecutive days represent the timepoints on the x-axis.

Tumor dimensions were recorded every day beginning on the day that the tumors were considered measurable. These were plotted for every 2 consecutive days of measurements beginning on the first day that each mouse had a measurable tumor over the course of 36 days (FIG. 3).

Using data that were platted for every 2 consecutive days of measurements beginning on the first day that each mouse had a measurable tumor over the course of 36 days (FIG. 3), the second timepoint of measurable tumor appearance (4$^{th}$ day of measurable tumors), both OHGF and paclitaxel/OGF mice had significantly ($p<0.05$) smaller tumors than control mice with reductions of 26% and 29%, respectively. On the 3$^{rd}$ timepoint, all 3 treatment groups had mean tumor volumes that were significantly smaller than controls by 29 to 33%. At timepoints 8 to 10, paclitaxel/OGF mice had tumors that were significantly smaller than tumor sizes in groups receiving single treatments. From timepoint 11 (see FIG. 3) through the end of the trial, paclitaxel/OGF mice exhibited tumor volumes that were significantly smaller than both the control and OGF mice, but comparisons to paclitaxel mice revealed no significance due to the fact that mice in the paclitaxel group began to die around this timepoint. Death of the paclitaxel mice made the statistical analysis difficult. In some cases the mice began to exhibit common side effects of the chemotherapy and tumor sizes often decreased. Therefore tumor measurements comparing the paclitaxel and paclitaxel/OGF mice were often non-significant, both due to the decreased tumor size before death and lowered N value in the paclitaxel group.

EXAMPLE 3

Combination Therapies on the MiaPaCa-2 Cell Lines

Figure 7:
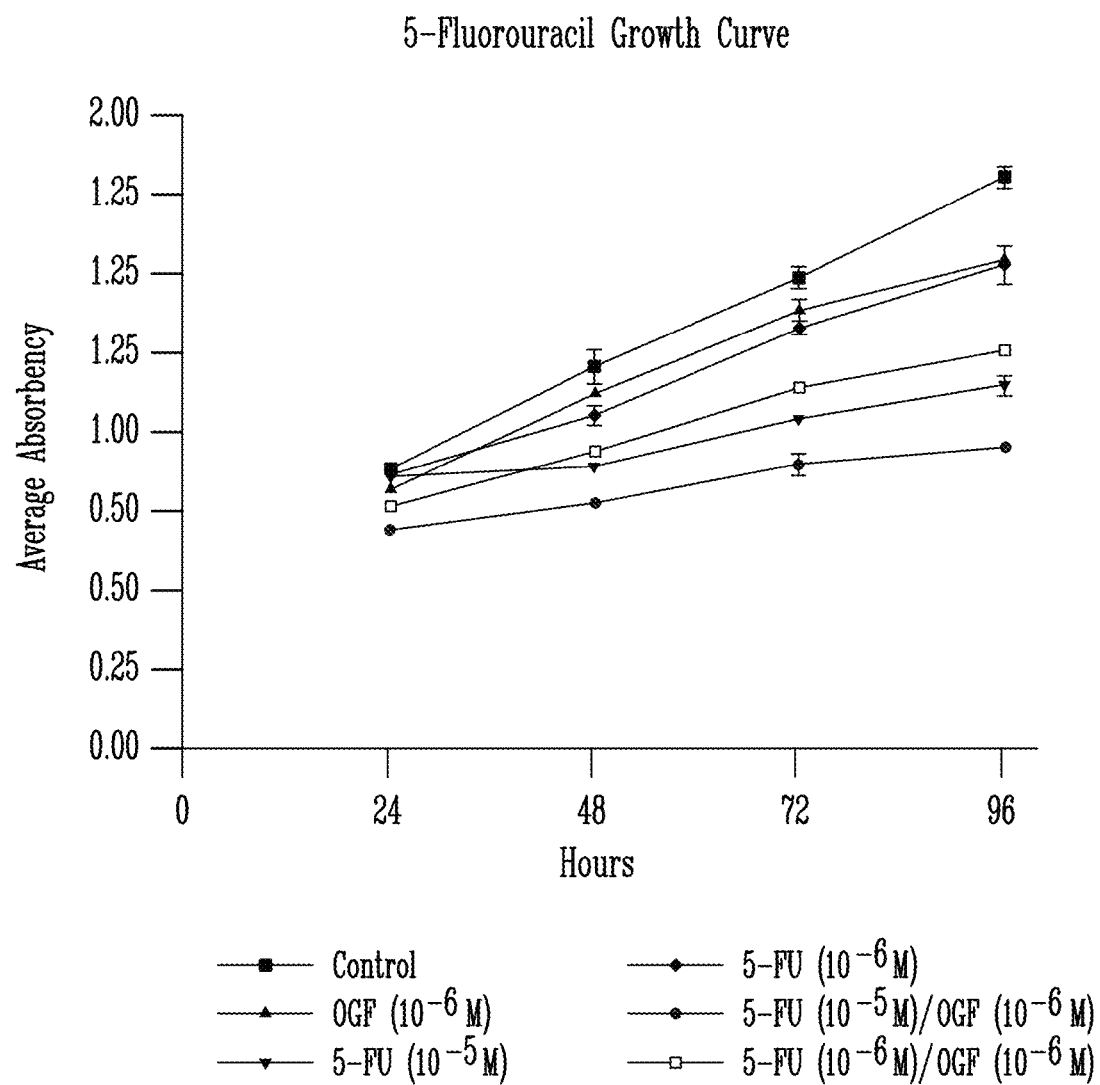
FIG. 7 is a graph representing a 96-hour growth curve for MiaPaCa-2 cells being treated with 5-FU and/or OGF. Each data point represents the average absorbency for 10 wells±S.E.M. Significance values for each timepoint can be found on Table 4.

The results illustrated in FIG. 7 examine the addition of 5-FU and/or OGF to MiaPaCa-2 cells. Throughout the 4-day treatment period statistical analysis (ANOVA) revealed that the OGF ($10^{-6}$ M) alone significantly inhibited growth at 24, 48, 72, and 96 hours with decreases in cell number from controls of 7.1, 7.0, 6.9 and 14.2%, respectively. 5-FU at a concentration of 10-5 M inhibited cell growth at 48, 72, and 96 hours decreasing cell number by 26.0, 30.1, and 36.4%, respectively relative to controls. 5-FU at a concentration of $10^{-6}$ M also inhibited growth at 48, 72 and 96 hours decreasing cell number relative to controls by 12.7, 10.8 and 15.2%, respectively. When 5-FU ($10^{-5}$ M) was combined with OGF ($10^{-6}$ M), growth inhibition was observed at 24, 48, 72, and 96 hours resulting in decreases in cell number from sterile water treated controls of 21.5, 35.7, 39.7, and 47.4%, respectively. When 5-FU ($10^{-6}$ M) was combined with OGF ($10^{-6}$ M), cell growth inhibition was observed at 24, 48, 72 and 96 hours with decreases in cell numbers from control of 13.2, 22.2, 23.6 and 30.3%, respectively. OGF in combination with 5-FU at $10^{-5}$ M was significantly more inhibitory than any drug alone at 24, 48, 72 and 96 hours, with decreases in cell numbers ranging from 15.5 to 38.7%.

EXAMPLE 4

Gemcitabine and OGF Cell Cycle Phase Analysis

To investigate the exact cell cycle phase where gemcitabine and/or OGF exerted their effects, flow cytometry was performed. OGF showed no significant increases into the $G_0/G_1$ phase of the cell cycle although slight increases in the percentages of cells in this phase were observed at 2, 4, 6, 8, 12, 20, and 24 hours after OGF exposure. Gemcitabine is known to alter the $G_1/S$ phase and this recruitment can be observed as early as 6 hours after treatment with either gemcitabine or gemcitabine/OGF. Decreased percentages of cells in the $G_2/M$ phase of the cell cycle were observed with cells treated with gemcitabine/OGF as compared to cells treated with just gemcitabine, indicating that more cells were stalled in the $G_1S$ with the combined therapy. At 48 and 120 hours of treatment with gemcitabine, $G_1$ recruitment remained strong with 73.50% and 60.75% of cells respectively still in $G_1$ with the gemcitabine/OGF treatment at 48 and 120 hours, 74.03% and 60.15% of cells were arrested in the $G_1$ phase of the cell cycle.

EXAMPLE 5

In Vivo OGF/Gemcitabine Treatment in Nude Mouse Model

To examine the effectiveness of the combined OGF/gemcitabine treatments in vivo, an athymic nude mouse model was used. Treatments of OGF (10 mg/kg daily), gemcitabine (120 mg/kg every 3 days), and gemcitabine (120 mg/kg every 3 days)/OGF (10 mg/kg daily) were used to treat the mice inoculated with $1\times10^6$ MiaPaCa-2 cells.

a. MiaPaCa-2 Tumor Appearance and Growth

Figure 8:
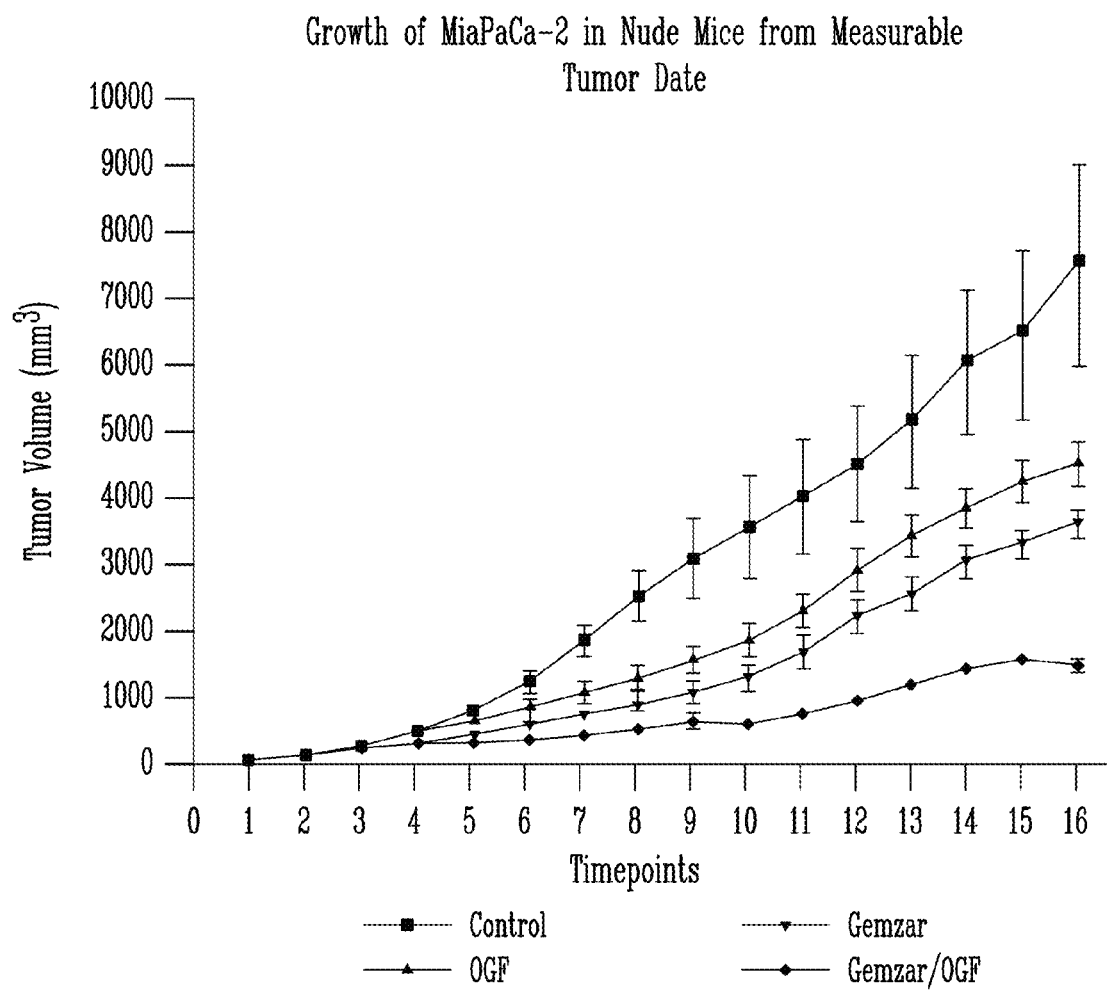
FIG. 8 shows the growth of MiaPaCa-2 human pancreatic cancer cells in athymic nude mice. Timepoint 1 signifies the first day that tumors became measurable in each treatment group. Tumor volumes were recorded every day and averages from 2 consecutive days represent the timepoints on the x-axis. Graph is meant to show growth trends once tumors became measurable in each group. Graph disregards latency to measurable tumor development to illustrate this trend.

All mice that were injected with MiaPaCa-2 cells developed tumors. On day 16 after tumor cell inoculation, all mice in the control saline treatment group as well as the OGF group had a tumor, while 75% of gemcitabine treated mice, and 0% of gemcitabine/OGF (p<0.0001) treated mice, had tumors (See FIG. 8). When examining latency to a visible tumor, control mice developed visible, but not measurable, tumors within 10 days of tumor cell inoculation. OGF mice and gemcitabine mice also developed tumors within the same 10-day time frame while gemcitabine/OGF mice developed tumors within 16 days, exhibiting an approximate 6-day delay in visible tumor development (p<0.05). The latency time for measurable (62.5 $mm^3$) tumors displayed an analogous pattern to the latency for visible tumors. Control, OGF, and gemcitabine groups had measurable tumors within 2 weeks of tumor cell inoculation while the gemcitabine/OGF group developed measurable tumors within 20 days (p<0.05). Tumor dimensions were recorded every day beginning on the day that the tumors were considered measurable and data were plotted for every 2 consecutive days of measurements beginning on the first day that each mouse had a measurable tumor over the course of 31 days.

Using data that were plotted for every 2 consecutive days of measurements beginning on the first day that each mouse had a measurable tumor over the course of 36 days (FIG. 8) from the $6^{th}$ timepoint of measurable tumor appearance ($12^{th}$ day of measurable tumor incidence), OGF mice had significantly (p<0.01 timepoints 7, 9, and 16, p<0.001 timepoint 8, and p<0.05 all remaining) smaller tumors than control mice with reductions of 29.9-40.7%, respectively. Starting with the $4^{th}$ timepoint, all 3 treatment groups had tumors that were significantly smaller than control tumors. At every timepoint besides 3, 9, 10, and 11, gemcitabine/OGF mice had tumors that were significantly smaller than tumor sizes in the OGF group. At timepoints 1, 4, 14, 15, and 16, gemcitabine/OGF mice had significantly smaller tumors than the gemcitabine mice alone. Tumor volumes of mice receiving gemcitabine only significantly differed from the tumor volumes of mice receiving OGF at timepoints 4, 5, and 6. Although ANOVA did not reveal many significances between gemcitabine versus gemcitabine/OGF other than mentioned above, volumes of gemcitabine/OGF tumors were smaller by 29.8-56.9% at points that were not deemed significant by ANOVA.

EXAMPLE 6

Gemcitabine Growth Curve-Cell Counting

Figure 9:
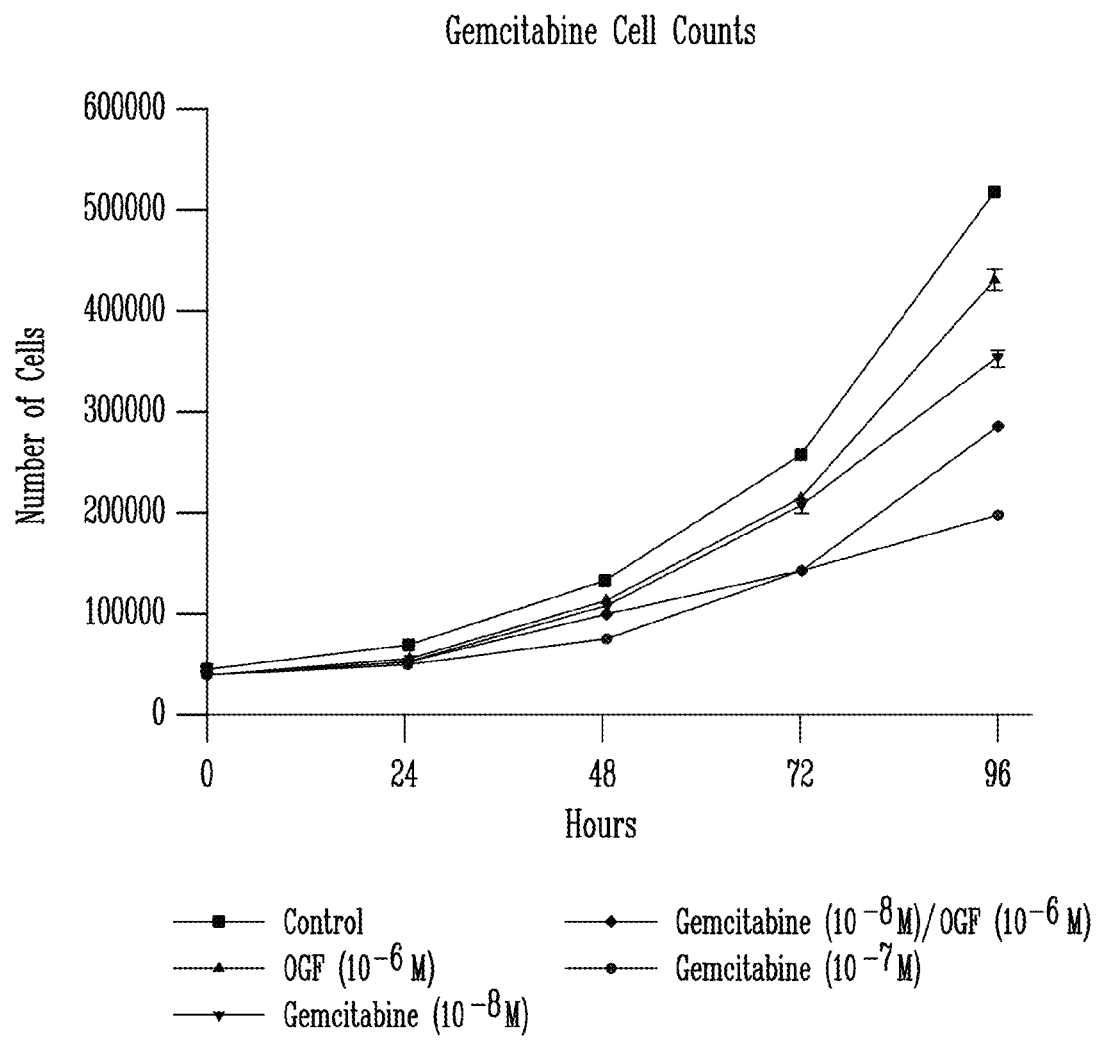
FIG. 9 shows the growth of MiaPaCa-2 human pancreatic cancer cells against time subjected to daily addition of the above drug regiments. Values represent the means from 4 wells/timepoint±S.E.M. Significance values can be found on Table 5.

Further investigation of the effects of gemcitabine and/or OGF on the growth of MiaPaCa-2 cells was explored by performing actual cell counts. FIG. 9 illustrates that OGF ($10^{-6}$ M) alone inhibited growth at 48, 72, and 96 hours with decreases in cell number from controls of 15.5, 17.6, and 16.7%, respectively. Gemcitabine at a concentration of $10^{-7}$ M inhibited cell growth at 24, 48, 72, and 96 hours decreasing cell number relative to controls by 30.1, 46.4, 47.7, and 64.2%, respectively. Gemcitabine at a concentration of $10^{-8}$ M also inhibited growth at 48, 72, and 96 hours decreasing cell number relative to controls by 21.7, 21.2, and 32.4%, respectively. When gemcitabine ($10^{-8}$ M) was combined with OGF ($10^{-6}$ M), growth inhibition was observed at 48, 72, and 96 hours resulting in decreases in cell number of 26.3, 49.2, and 45.9%, respectively. Gemcitabine ($10^{-8}$ M) when combined with OGF ($10^{-6}$ M) was significantly more inhibitory than OGF alone at 72 and 96 hours and gemcitabine ($10^{-8}$ M) alone at 72 and 96 hours (See Table 5).

Table 1 shows significance values obtained from a one-way ANOVA for paclitaxel and/or OGF versus controls (A), OGF (B), paclitaxel $10^{-7}$ M (C), and paclitaxel $10^{-8}$ M (D) over a 96-hour trial.

Table 2 shows significance values obtained from a one-way ANOVA for carboplatin (Carb) and/or OGF versus controls (A), OGF (B), carboplatin $10^{-6}$ M (C), and carboplatin $10^{-7}$ M (D) over a 96-hour trial.

Table 3 shows significance values obtained from a one-way ANOVA for gemcitabine and/or OGF versus controls (A), OGF $10^{-6}$ M (B), gemcitabine $10^{-7}$ M (C), and gemcitabine $10^{-8}$ M (D) over a 96-hour trial.

Table 4 shows significance values obtained from a one-way ANOVA for 5-FU and/or OGF versus controls (A), OGF (B), 5-FU $10^{-5}$ M (C), or 5-FU $10^{-6}$ M (D) over a 96-hour trial.

Table 5 shows significance values obtained from a one-way ANOVA for gemcitabine and/or OGF versus controls (A), OGF (B), gemcitabine $10^{-7}$ m (C), and gemcitabine $10^{-8}$ M (D) over a 96-hour trial.

EXAMPLE 7

Given the promising nature of OGF (biotherapy), and of gemcitabine (chemotherapy), as antitumor agents in pancreatic cancer, and the lack of preclinical data regarding the simultaneous use of OGF and gemcitabine, the present study was designed to explore the therapeutic potential of a combination of these modalities. Using a tissue culture model of human pancreatic adenocarcinoma, the effect of concomitant exposure to both OGF and gemcitabine were characterized on growth (e.g., reversibility, receptor mediation, specificity). The relationship of another chemotherapy treatment (i.e., 5-FU) and OGF in regard to pancreatic cancer, as well as the ubiquity of combined therapy on other pancreatic cancer cell lines, were evaluated. Finally, the present report addresses the question of whether a combination of OGF and gemcitabine influences growth of human pancreatic cancer in vivo, and does so beyond the efficacy of each compound. The effects of OGF and/or gemcitabine on tumor incidence, appearance, and size, as well as metastasis, were examined in a xenograft model of pancreatic cancer.

Material and Methods

Cell Lines

MIA PaCa-2 and PANC-1 human pancreatic adenocarcinoma cell lines were purchased from the American Type Culture Collection (Manasass, Va.). MIA PaCa-2 cells were derived from an undifferentiated epithelial carcinoma occurring in the body and tail of the pancreas in a 65-year-old man [36]. The PANC-1 cells were derived from an undifferentiated carcinoma from the head of the pancreas in a 56-yr old man [18]. MIA PaCa-2 and PANC-1 cells were grown in Dulbecco's MEM (modified) media; media was supplemented with 10% fetal calf serum, 1.2% sodium bicarbonate, and antibiotics (5,000 Units/ml penicillin, 5 mg/ml streptomycin, 10 mg/ml neomycin), and the cells were maintained in a humidified atmosphere of 7% $CO_2$/93% air at 37° C.

Growth Assays

MIA PaCa-2 cells were seeded at equivalent amounts into either 75 $cm^2$ flasks, 6-well plates, or 96-well plates (Falcon) and counted 24 hr later to determine plating efficiency. Growth assays for PANC-1 cells were conducted in 6-well plates (Falcon). Compounds or sterile water were added beginning 24 hr after seeding (=0 hr), and both media and compounds were replaced daily. All drugs were prepared in sterile water and dilutions represent final concentrations of the compounds.

Cell number was recorded either by using a mitogenic bioassay, the MTS assay (Cell Titer 96 One Solution, Promega, Madison, Wis.), and measuring absorbency after 4 hr on a Biorad (Model 3550) plate reader at 490 nm, or by counting cells. For manual counts, cells were harvested with a solution of 0.25% trypsin/0.53 mM EDTA, centrifuged, and counted with a hemacytometer. Cell viability was determined by trypan blue staining. At least two aliquots per flask or 4-10 wells/treatment were counted at each time.

Animals and Tumor Cell Implantation

Male 4 week old BALB/c-nu/nu nude mice purchased from Harlan Laboratories (Indianapolis, Ind.) were housed in pathogen-free isolators in the Department of Comparative Medicine at the Penn State University College of Medicine. All procedures were approved by the IACUC committee of the Penn State University College of Medicine and conformed to the guidelines established by NIH. Mice were allowed 48 hr to acclimate prior to beginning experimentation.

MIA PaCa-2 cells ($10^6$ cells/mouse) were inoculated into nude mice by subcutaneous injection into the right scapular region; mice were not anesthetized for this procedure.

Drug Treatment

Four groups of mice (n=12) were randomly assigned to receive intraperitoneal injections of 10 mg/kg OGF daily, 120 mg/kg gemcitabine every 3 days; 10 mg/kg OGF daily and 120 mg/kg gemcitabine every 3rd day, or 0.1 ml of sterile saline daily [29, 38]. All drugs were dissolved in saline and prepared weekly. Injections were given within 1 hr of tumor cell inoculation.

Tumor Growth and Metastases

Mice were weighed weekly throughout the experiment, and observed daily for the presence of tumors. The latency for a visible tumor to appear, and the time until tumors were measurable (i.e., 62.5 mm$^3$) were recorded. Tumors were measured using calipers every day after tumor appearance. Tumor volume was calculated using the formula $w^2 \times l \times \pi/6$, where the length is the longest dimension, and width is the dimension perpendicular to length [31].

Termination Day Measurements

According to IACUC guidelines, mice were terminated when tumors became ulcerated, or tumors grew to 2 cm in diameter. Forty-five days following tumor cell inoculation, all mice were euthanized by an overdose of sodium pentobarbital (100 mg/kg) and killed by cervical dislocation; mice (with tumors) were weighed. Tumors and spleens were removed and weighed, and the lymph nodes, liver, and spleen examined for metastases.

Plasma Levels of [Met$^5$]-enkephalin (OGF)

At the time of termination, trunk blood was collected from some mice in each group. Plasma was separated and OGF levels were measured by standard radioimmunoassay procedures using a [Met$^5$]-enkephalin kit from Peninsula Laboratories (Belmont, Calif.).

Chemicals

The following compounds were obtained from Sigma Chemicals (St. Louis, Mo.): [Met$^5$]-enkephalin (OGF), [D-Pen$^{2,5}$]-enkephalin (DPDPE), [D-Ala$^2$,MePhe$^4$,Glyol$^5$]-enkephalin (DAMGO), β-endorphin, naltrexone (NTX), naloxone, dynorphin A1-8, [D-Ala-D-Leu-enkephalin] (DADLE), morphine, endomorphin-1, and endomorphin-2.

Data Analysis

Cell numbers and/or absorbencies were analyzed using analysis of variance (ANOVA) (one- or two-factor where appropriate) with subsequent comparisons made using Newman-Keuls tests. Incidence of tumors was analyzed by chi-square tests. Latency for tumor appearance and tumor volume were analyzed using either two-tailed t-tests or ANOVA with subsequent comparisons made using Newman-Keuls tests. Termination data (i.e., body weight, tumor weight, spleen weight) and OGF plasma levels were compared by ANOVA.

Results

Growth Assays with OGF and/or Gemcitabine

Figure 10:
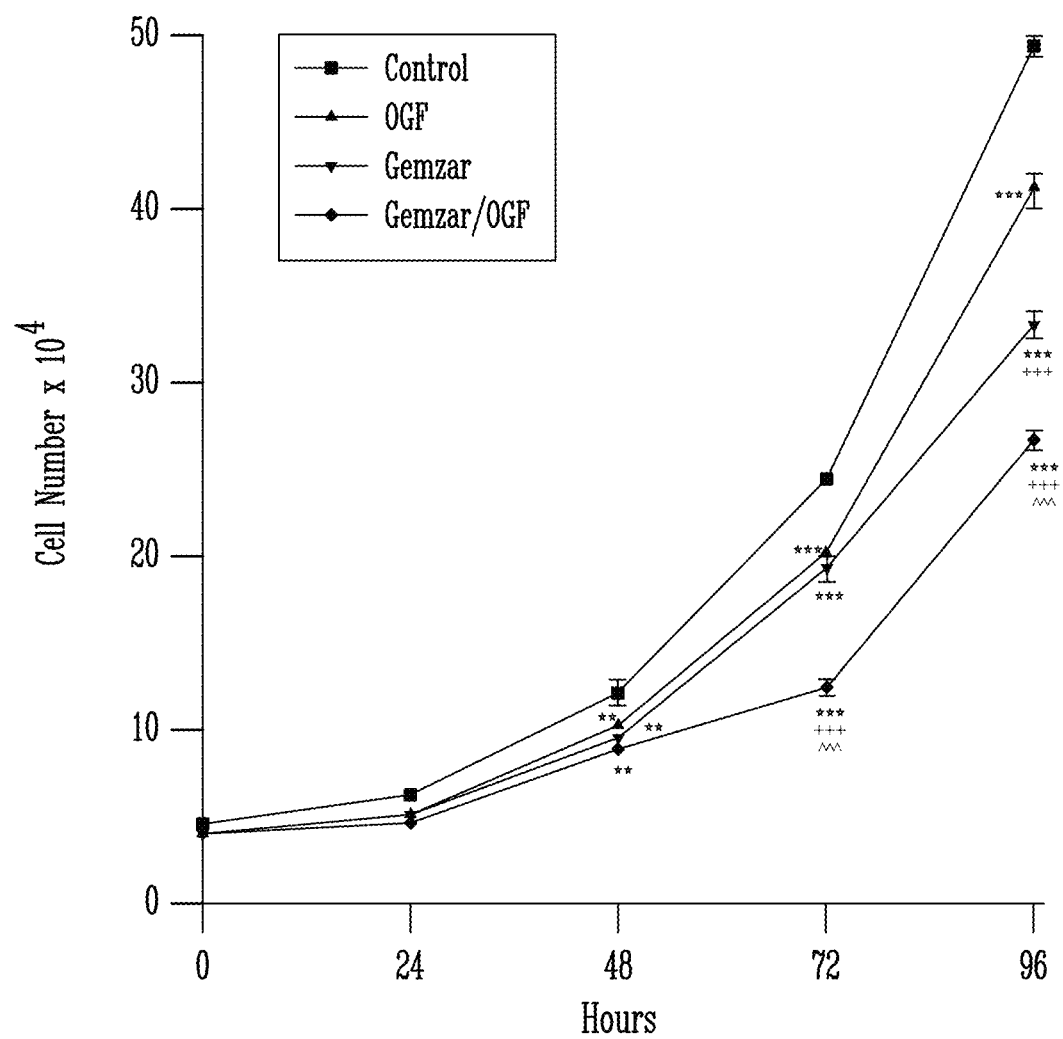
FIG. 10 shows cell proliferation assays of MIA PaCa-2 cells subjected to OGF ($10^{-6}$ M) and/or gemcitabine ($10^{-8}$) (Gemzar) for 96 hr. Drugs or an equivalent volume of sterile water (controls) were added 24 hr (0 hr) after seeding in 6-well plates; media and drugs were replaced daily. Data represent means±SEM for at least 4 wells per treatment at each time point. Significantly different from controls at p<0.01 () and p<0.001 (*). Significantly different from OGF-treated cultures at p<0.001 (+++). Significantly different from cultures treated with gemcitabine alone at p<0.001 (^^).

Growth curves for MIA PaCa-2 cell cultures treated with $10^{-6}$ M OGF (a dosage known to inhibit proliferation of MIA PaCa-2 cells, 44), $10^{-8}$ M gemcitabine (a dosage selected because preliminary experiments revealed no logarithmic growth with a dosage of $10^{-7}$ M), $10^{-8}$ M gemcitabine and $10^{-6}$ M OGF, or sterile water (Controls) are presented in FIG. 10. OGF alone inhibited growth at 48, 72, and 96 hr relative to controls, with decreases in cell number of 16%, 18%, and 17%, respectively, noted. Gemcitabine alone decreased cell number relative to controls at 48, 72, and 96 hr by 22%, 21%, and 32%, respectively. Cells treated with a combination of OGF and gemcitabine were decreased in number relative to controls by 26%, 49%, and 46% at 48, 72, and 96 hr, respectively. At 72 hr, cell number in cultures receiving the combined therapy of gemcitabine and OGF was reduced (p<0.001) from cells exposed only to OGF or gemcitabine by 38% and 36%, respectively. Moreover, at 96 hr, the combined therapy of gemcitabine and OGF reduced (p<0.001) MIA PaCa-2 cell number by 35% and 20% from cultures receiving only OGF or gemcitabine, respectively.

Growth Assays with 5-fluorouracil

Figure 11:
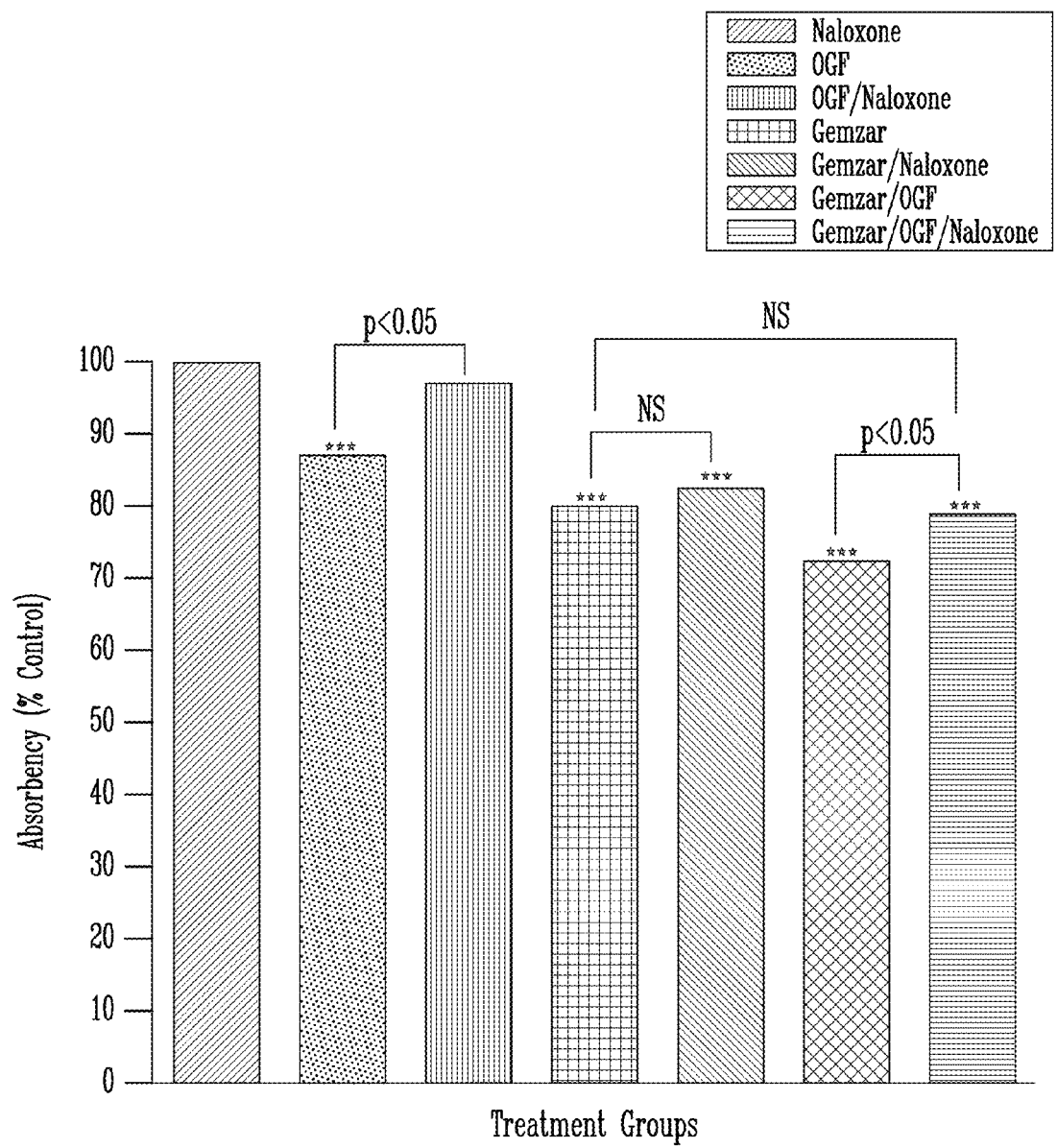
FIG. 11 depicts growth of MIA PaCa-2 cells treated with 5-FU ($10^{-6}$ M) and/or OGF ($10^{-6}$ M) as measured by the MTS assay (96-well plates). Values represent mean absorbencies±SEM for 10 wells at each time point. Significantly different from controls at p<0.05 (*), p<0.01 (), and p<0.001 (*). Significantly different from OGF-treated cultures at p<0.001 (+++). Significantly different from 5-FU-treated cultures at p<0.01 (^^) and p<0.001 (^^^).

To examine whether OGF could enhance the inhibitory effects of other chemotherapies commonly used to treat pancreatic cancer, MIA PaCa-2 cell cultures were exposed to 5-fluorouracil (5-FU) at a concentration of $10^{-6}$ M for 4 days (FIG. 11). MIA PaCa-2 cell number in the 5-FU group was reduced 11% to 15% from control levels at 48, 72, and 96 hr. Combination therapy of 5-FU ($10^{-6}$ M) and OGF ($10^{-6}$ M) reduced cell number from control values at 24, 48, 72, and 96 hr by 13% to 30%. At all time points examined, the combined therapy of 5-FU and OGF reduced MIA PaCa-2 cell number by 6% to 19% from cultures receiving only OGF, and 10% to 17% from cultures receiving only 5-FU.

Receptor Mediated Effects of OGF and/or Gemcitabine

Figure 12A:
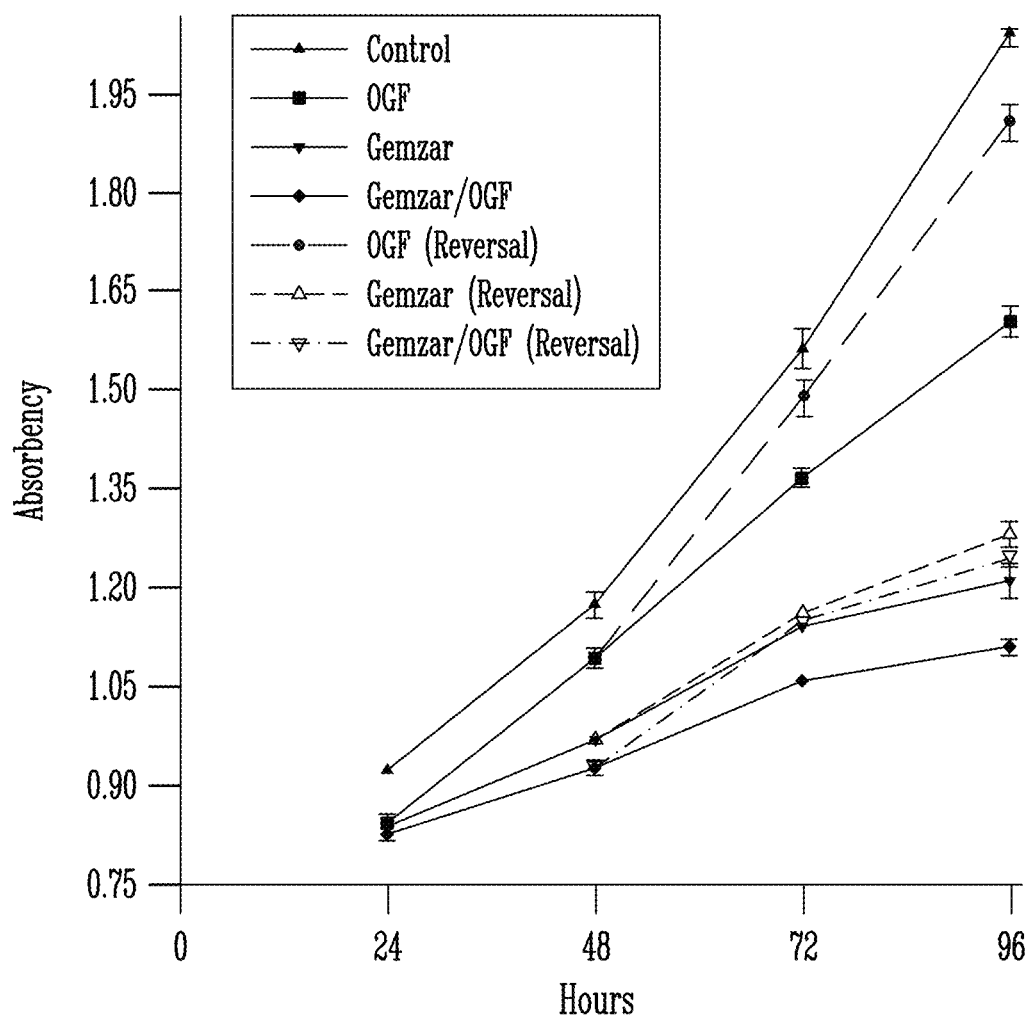
FIG. 12A depicts receptor mediation of the growth inhibitory effects of gemcitabine and/or OGF in MIA PaCa-2 cells. The number of MIA PaCa-2 cells at 24, 48, 72 and 96 hr as measured by the MTS assay after being subjected to OGF ($10^{-6}$ M), the opioid antagonist naloxone ($10^{-6}$ M), gemcitabine (Gemzar) ($10^{-8}$ M), or combinations of these compounds; controls were treated with an equivalent volume of sterile water.
Figure 12B:
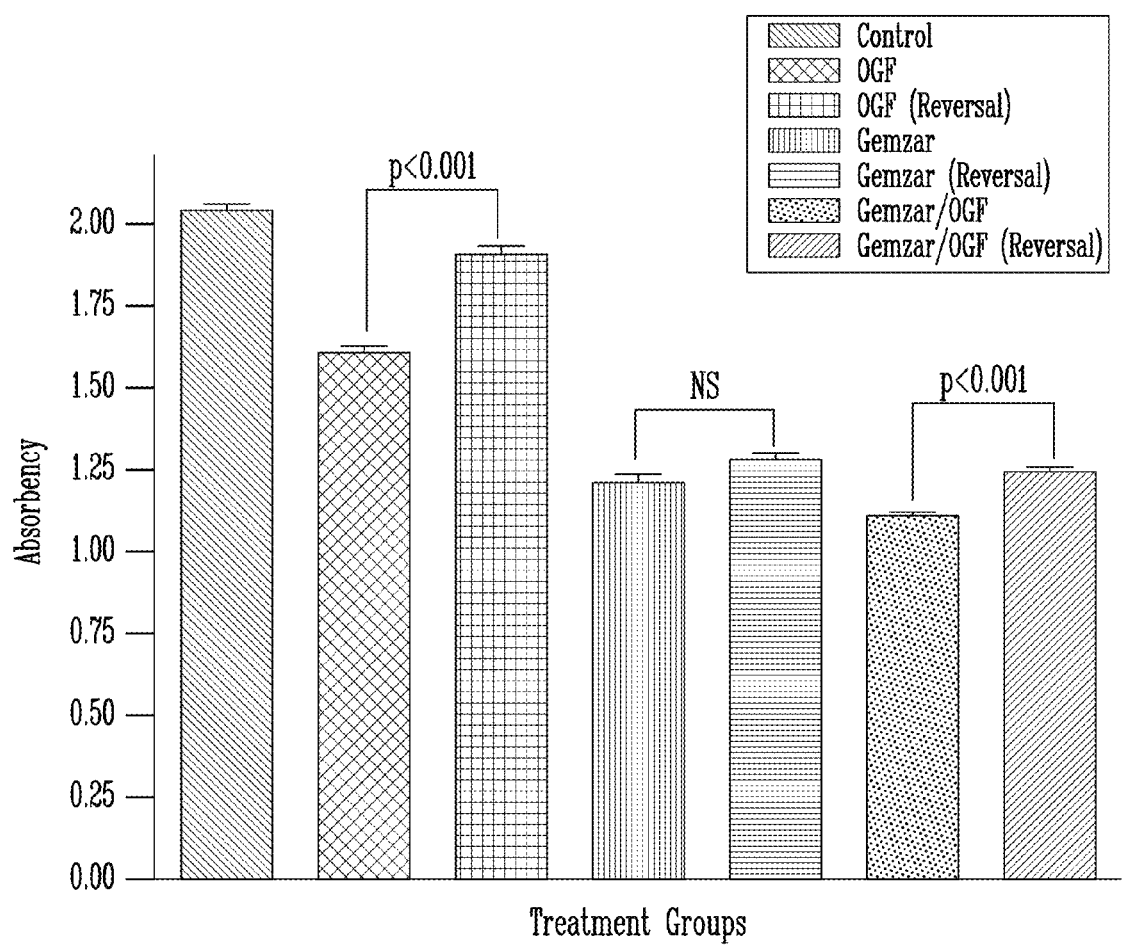
FIG. 12B depicts receptor mediation of the growth inhibitory effects of gemcitabine and/or OGF in MIA PaCa-2 cells. The number of MIA PaCa-2 cells at 96 hr as measured by the MTS assay after being subjected to OGF ($10^{-6}$ M), the opioid antagonist naloxone ($10^{-6}$ M), gemcitabine (Gemzar) ($10^{-8}$ M), or combinations of these compounds; controls were treated with an equivalent volume of sterile water. Compounds and media were replaced every 24 hr. Data represent mean absorbency±SEM for 10 wells/treatment at 96 hr. Significantly from controls at $p<0.001$ (***). NS=not significant.

To inquire whether OGF activity was mediated by the OGF receptor, a short-acting opioid antagonist, naloxone, was added at a dosage of $10^{-6}$ M into cultures receiving $10^{-6}$ M OGF and/or gemcitabine ($10^{-8}$ M). MIA PaCa-2 cells grown in 96-well plates were treated with $10^{-6}$ M OGF, $10^{-6}$ M naloxone, $10^{-8}$ M gemcitabine, or combinations at the same concentrations—OGF/naloxone, gemcitabine/naloxone, gemcitabine/OGF, and gemcitabine/OGF/naloxone; control cultures received sterile water. Individual plates were read at 96 hr after drug addition. Relative to control levels, addition of OGF, gemcitabine, gemcitabine/OGF, and gemcitabine/OGF/naloxone inhibited cell growth from 13% to 36% (FIG. 12). Addition of naloxone completely blocked the growth inhibitory effects of OGF alone, but had no effect on the growth inhibitory action of gemcitabine alone. Moreover, naloxone partially neutralized the enhanced inhibitory effect of the combination of gemcitabine and OGF; cell number of the gemcitabine/OGF/naloxone group was comparable to cells exposed to gemcitabine, but were significantly reduced from control levels. Naloxone alone had no effect on the growth of MIA PaCa-2 cells.

Reversibility of the Inhibitory Growth Effects of OGF and/or Gemcitabine

Figure 13:
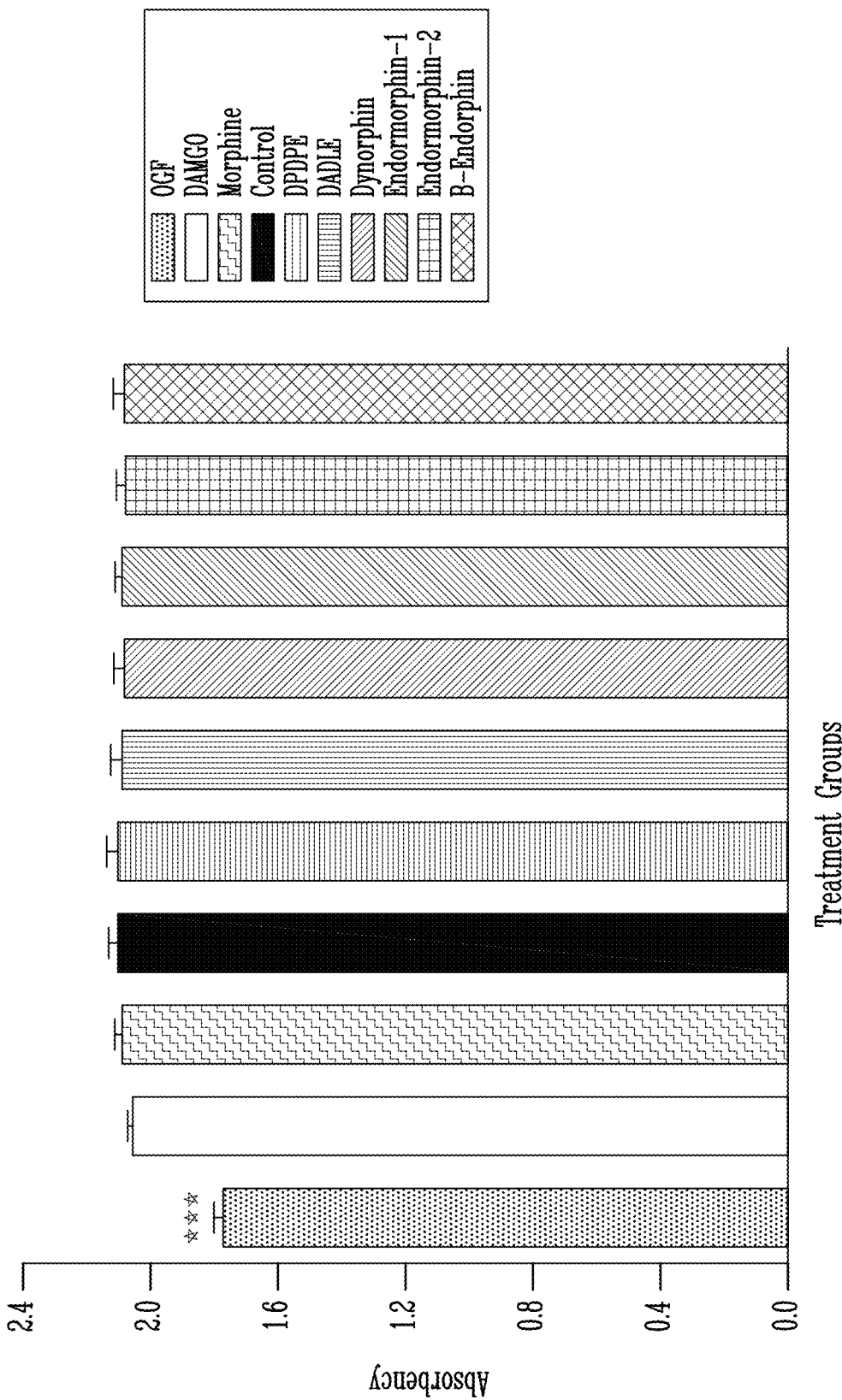
FIG. 13 shows reversibility of the growth inhibitory effects on MIA PaCa-2 cells treated with OGF and/or gemcitabine (Gemzar). Cells were seeded into 96-well plates and treated with drugs for 48 hr. At 48 hr, half of the plates continued to receive the same drugs for an additional 48 hr, and half of the plates were treated with sterile water for 48 hr. Control cultures received sterile water throughout the 96 hr. Compounds and media were replaced daily. A. Growth of cells in the reversibility experiments. B. Cell number at 96 hr in the treatment groups. All data represent mean absorbency±SEM for 10 wells/treatment. Comparisons between cell number of cultures maintained with drugs or cultures with drugs replaced by vehicle (reversal) are presented. NS=not significant.

To establish whether the effect of OGF and/or gemcitabine on cell number could be reversed by withdrawing cells from drug exposure, cultures of MIA PaCa-2 cells were exposed for 48 hr to $10^{-6}$M OGF and/or $10^{-8}$M gemcitabine. At 48 hr after drug exposure, half of the plates had media removed and fresh media added with no addition of OGF or gemcitabine (i.e., OGF-reversal; gemcitabine-reversal; gemcitabine/OGF-reversal groups); some cultures continued to receive new media and drugs. At 96 hr (i.e., 48 hr after reversal), the OGF, gemcitabine, gemcitabine-reversal, gemcitabine/OGF, and the gemcitabine/OGF-reversal groups differed from controls by 21% to 46% (FIGS. 13A, B). The OGF-reversal group had 16% more cells than in the OGF group continuing with OGF exposure. However the gemcitabine-reversal group did not differ from cell cultures continuing to be treated with gemcitabine. Cell cultures exposed to the combination of OGF and gemcitabine had 7% fewer cells than cultures in the gemcitabine/OGF-reversal group.

Specificity of Opioid Peptide(s) Related to Pancreatic Cancer Cell Growth

Figure 14:
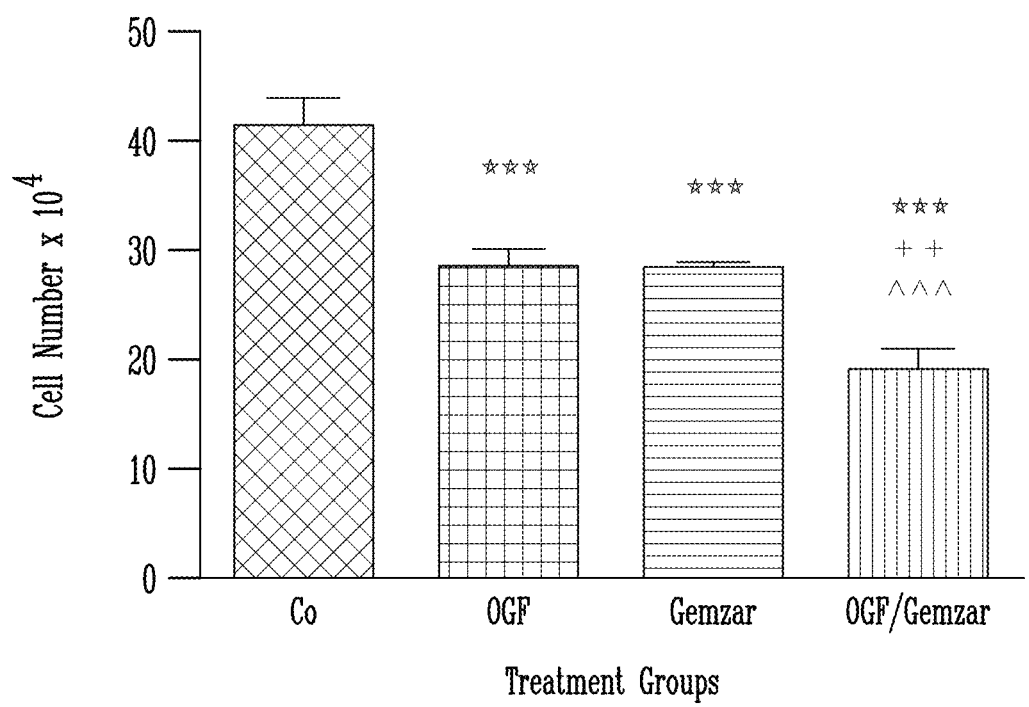
FIG. 14 shows growth of MIA PaCa-2 cells grown in 96-well plates treated with a variety of endogenous and exogenous opioids at a concentration of $10^{-6}$ M. Data represent mean absorbency values±SEM for 10 wells/treatment. Significantly different from controls at $p<0.001$ (***).

To determine whether other opioid peptide(s) is(are) related to growth, MIA PaCa-2 cultures (1,000 cells/well) were treated daily with $10^{-6}$ M concentrations of a variety of natural and synthetic opioid ligands. In some cases, these ligands were specific for other opioid receptors (e.g., μ, δ, or κ receptors). Drugs included OGF, DAMGO, morphine, DPDPE, DADLE, dynorphin A1-8, endomorphin-1, endomorphin-2, and β-endorphin. Cell number was measured on a plate reader after 96 hr of treatment (both drug and media were changed daily). OGF inhibited cell number by 16% relative to controls; none of the other drugs utilized had any inhibitory or stimulatory effect on growth (FIG. 14).

Ubiquity of Growth Inhibition by OGF

Figure 15A:
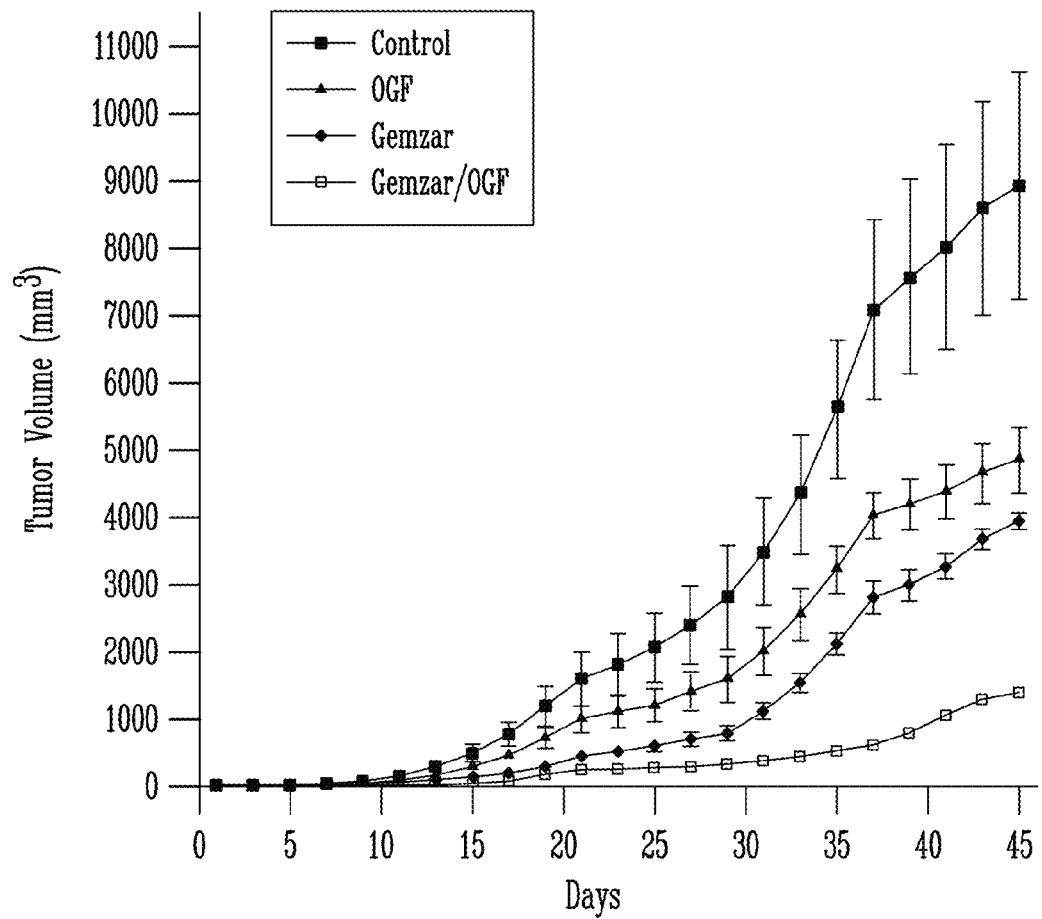
FIG. 15A shows effects of gemcitabine ($10^{-8}$ M) (Gemzar) and/or OGF ($10^{-6}$M) on PANC-1 cells grown in 6-well plates and measurements of tumor volume over 0, 5, 10, 15, 20, 25, 30, 35, 40 and 45 days.
Figure 15B:
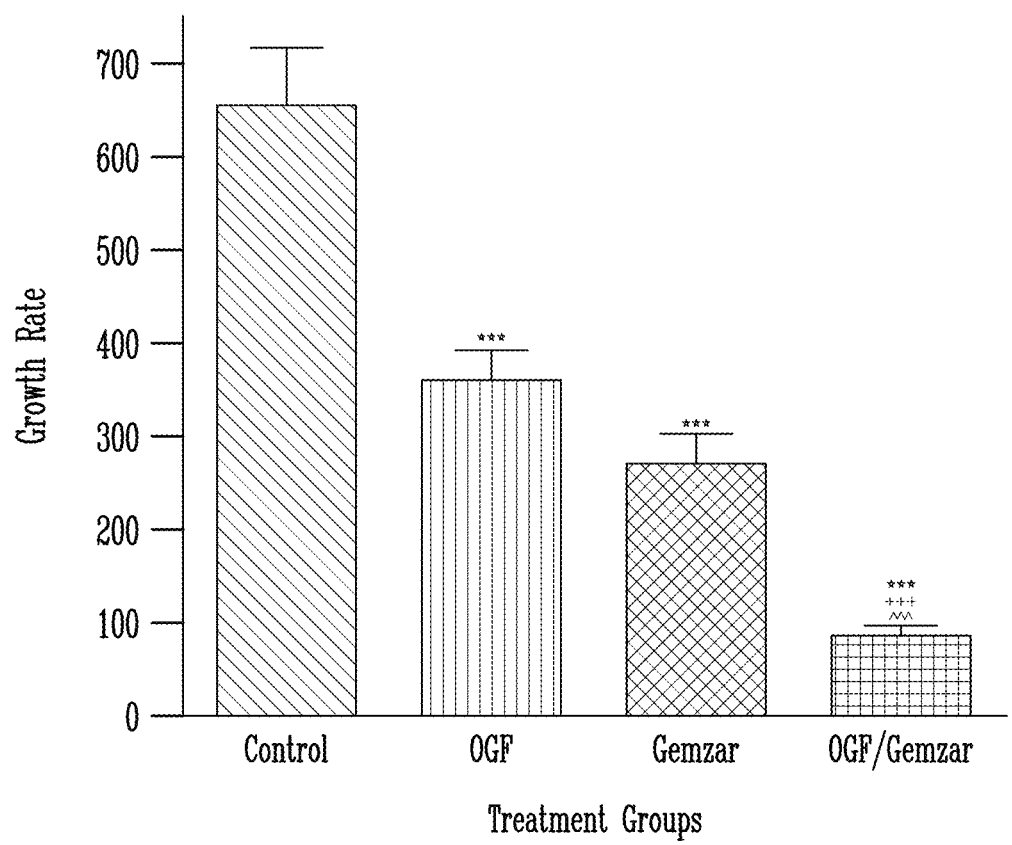
FIG. 15B shows effects of gemcitabine ($10^{-8}$M) (Gemzar) and/or OGF ($10^{-6}$ M) on PANC-1 cells grown in 6-well plates. Data represent means±SEM for 4 well at 72 hr of treatment. Significantly different from controls at $p<0.001$ (***), from OGF at $p<0.01$ (++), and from the respective dosages of gemcitabine at $p<0.001$ (^^^).

To determine whether the growth inhibition observed with MIA PaCa-2 cells following exposure to the combination of gemcitabine and OGF was not a cell-line specific action, another human pancreatic cancer cell line, PANC-1, was tested. After 72 hr, exposure of PANC-1 cells to either OGF ($10^{-6}$ M), gemcitabine ($10^{-8}$ M), OGF ($10^{-6}$ M) and gemcitabine ($10^{-8}$ M) revealed 31%, 31%, and 54%, respectively, fewer cells than in control cultures (FIG. 15). These differences in cell growth with exposure to OGF and/or gemcitabine differed significantly ($p<0.001$) from control levels, and the combination of OGF and gemcitabine differed from the OGF alone and the gemcitabine alone cultures at $p<0.01$.

MIA PaCa-2 Tumor Appearance and Growth

To investigate the effects of OGF and/or gemcitabine on pancreatic tumor growth in vivo, nude mice were injected with MIA PaCa-2 cells and treated with drugs. On day 10, when 80% of the mice in the saline-injected control group had measurable tumors, and 60% of the OGF and 75% of the gemcitabine-treated animals had tumors, no mouse in the gemcitabine/OGF group had a measurable tumor; the group receiving combination therapy of gemcitabine and OGF differed significantly from all other groups at $p<0.001$ (Table 6). On day 16, no differences in the incidence of measurable tumors could be detected between groups, and all animals had a tumor by day 17. The latency time for the appearance of a visible tumor in mice of the gemcitabine/OGF group was delayed by approximately 5 to 6 days from animals in the control, OGF, and gemcitabine groups; this delay for the gemcitabine/OGF group differed significantly from that of all other groups at $p<0.05$. The mean latency time for measurable tumor appearance in mice of the gemcitabine/OGF group was delayed ($p<0.05$) by approximately 6 days from animals in the control, OGF, and gemcitabine groups.

Figure 16:
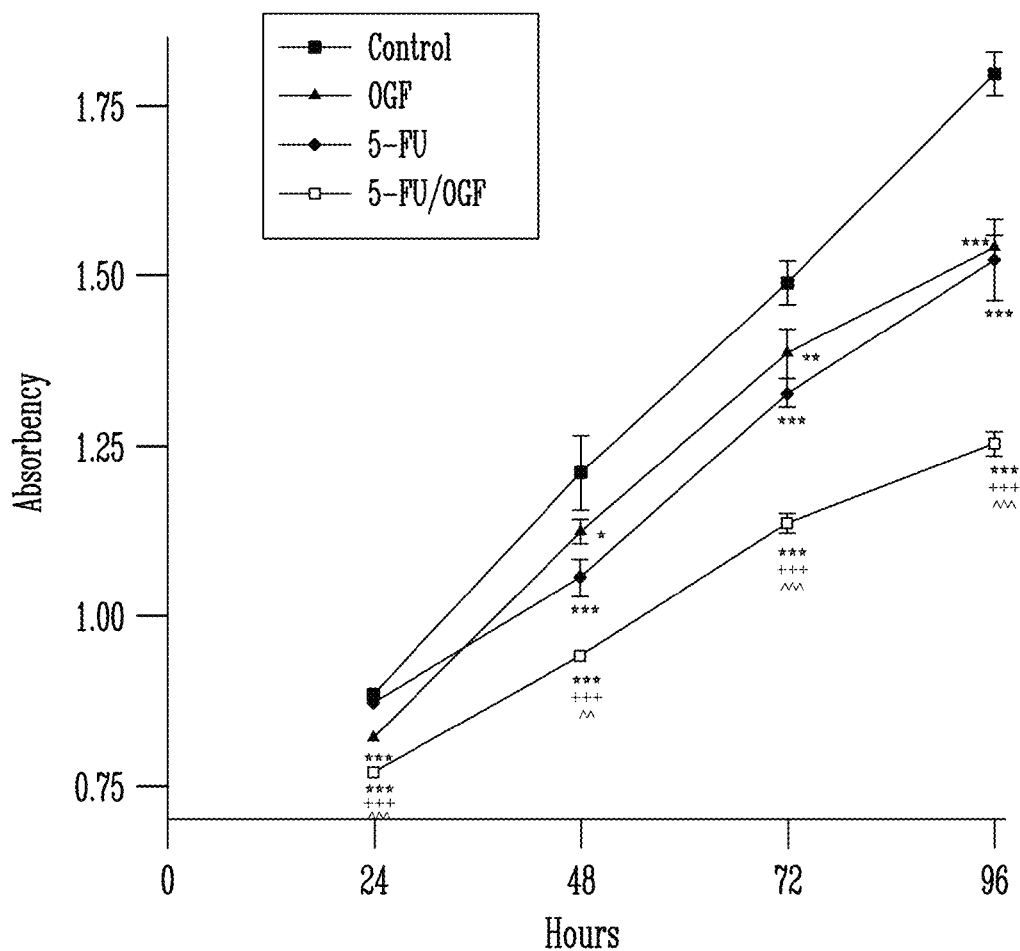
FIG. 16 shows MIA PaCa-2 cells treated with 5-FU ($10^{-6}$ M) and/or OGF ($10^{-6}$M) as measured by the MTS assay (96-well plates). Values represent mean absorbencies±SEM for 10 wells at each time point. Significantly different from controls at $p<0.05$ (*), $p<0.01$ (), and $p<0.001$ (*). Significantly different from OGF-treated cultures at $p<0.001$ (+++). Significantly different from 5-FU-treated cultures at $p<0.01$ (^^) and $p<0.001$ (^^^).

Changes in tumor volume over the 45 days of the experiment were analyzed (FIG. 16). The OGF, gemcitabine, and gemcitabine/OGF groups all differed (at least $p<0.05$) from controls in tumor volume beginning on day 14. Tumor volumes of mice receiving combined therapy (i.e., gemcitabine/OGF) differed ($p<0.05$) from mice treated with only OGF beginning on day 10, and from gemcitabine alone beginning on day 35. Differences in tumor volumes between groups persisted through the remainder of the experimental period. Rates of growth over the 45-day period of time were analyzed and presented in FIG. 16B. The results demonstrated that the growth rates of tumors for all 3 treatment groups were markedly reduced ($p<0.001$) from control levels. Moreover, the rate of growth of tumors in mice treated with a combination of gemcitabine and OGF were significantly decreased ($p<0.001$) from both the OGF alone and the gemcitabine alone groups.

At the time of termination (i.e., day 45), body weights of all groups of mice did not differ by statistical evaluation (Table 7). Moreover, autopsy of the animals in each group did not reveal any metastases. However, the weight of the spleen on day 45 for mice in the gemcitabine alone and the gemcitabine/OGF groups were decreased approximately 40% from control values; no changes in spleen weight of the OGF group in comparison to control levels were noted (Table 7). The weights of tumors on the termination day for the OGF alone, gemcitabine alone, and gemcitabine/OGF groups were decreased 36%, 56%, and 85%, respectively, from control levels (Table 7). Tumor volumes on day 45 for the OGF alone, gemcitabine alone, and gemcitabine/OGF groups were decreased 46%, 56%, and 83%, respectively, from control values (Table 7).

Plasma Levels of OGF

OGF levels in the plasma of nude mice bearing MIA PaCa-2 tumors ranged from 129 to 289 pg/ml. No differences were noted between control mice and those treated with OGF alone, gemcitabine alone, or gemcitabine/OGF.

Discussion

The results in this study demonstrate that the combination of OGF and gemcitabine has a potent inhibitory effect on growth in vitro of human pancreatic cancer. The antigrowth action of the combination of OGF and gemcitabine was always greater than the individual drugs. In a number of instances the effect of the combination of drugs exceeded that of the sum of the individual drugs, suggesting that the action of a combination of OGF and gemcitabine was supra-additive. The repressive effects on growth in vitro of pancreatic cancer cells observed with OGF and with gemcitabine individually were consonant with previous results [e.g., 8, 35, 44]. The action of OGF on cell growth was mediated by a naloxone-sensitive receptor. This naloxone-sensitive receptor is presumed to be OGFr, because synthetic and natural opioids selective for classical opioid receptors such as μ, δ, and κ did not influence growth of pancreatic cancer cells in the present report and earlier [44]. OGF also was discovered to have a reversible action on the replication of MIA PaCa-2 cells, supporting the result from earlier studies showing that treatment with this compound does not lead to cytotoxicity or cell death [39, 44]. On the other hand, the effects of gemcitabine on MIA PaCa-2 cells were neither blocked by naloxone nor could they be reversed, indicating that the characteristics of this drug's effects on MIA PaCa-2 cells is markedly different from that of OGF. Thus, this is the first report of the efficacy of using a combination of the biotherapeutic agent, OGF, and the chemotherapeutic agent, gemcitabine, to retard the growth of human pancreatic cancer.

Although this report concentrated on the effects of OGF and gemcitabine on MIA PaCa-2 cells, it is known that OGF, and gemcitabine, influence the growth of a variety of human pancreatic cancer cell lines [8, 35, 44]. The present investigation demonstrates that not only does OGF and gemcitabine in combination rather than individually have a more marked effect on MIA PaCa-2 cell growth, but a similar pattern can be found with another human pancreatic cancer cell line, PANC-1. Thus, it is reasonable to conclude that the effects of combination therapy with OGF and gemcitabine observed herein also extend to other human pancreatic cancer cell lines.

To address the question of whether OGF could be combined with chemotherapeutic agents other than gemcitabine, a preliminary study was conducted with the combination of OGF and 5-FU. This allowed a contrast between an antimetabolite (5-FU) and a cytosine analogue [32]. The mechanism of 5-FU, a pyrimidine analogue, is to inhibit thymidylate synthase (an enzyme involved in de novo synthesis of pyrimidines) by the active metabolite 5-fluoro-deoxyuridine-monophosphate. In addition, the active triphosphate metabolites, 5-fluoro-deoxyuridine-triphosphate and 5-fluoro-uridine-triphosphate, disrupt nucleic acid functions [6]. The present results are the first to show that the effects of a combination of 5-FU and OGF has potent inhibitory properties with respect to human pancreatic cancer. As in the case of gemcitabine and OGF, the effect of a combination of 5-FU and OGF on pancreatic cancer cells was markedly greater than that of each drug and was often additive in nature. Presumably, these results would indicate that OGF could be used in combination with a variety of chemotherapeutic agents.

The results of this study show that the antigrowth properties of OGF and gemcitabine are enhanced beyond the inhibitory effects of each drug alone. These data were most evident for tumor incidence, latency to a visible or measurable tumor, tumor weight, and tumor volume. Thus, the results of in vivo studies are consonant with observations conducted in vitro. Even though the tumor transplanatation investigation focused on one human pancreatic cancer cell line, it is known that OGF or gemcitabine influences the growth of a variety of human pancreatic cancer cell lines in vivo [3, 28, 35, 38]. Therefore, the effects of combination therapy with OGF and gemcitabine shown in this study will extend to other human pancreatic cancer cell lines in vivo.

The mechanism of the enhanced antitumor activity of a combination of OGF and either gemcitabine or 5-FU needs to be defined. OGF is targeted to the $G_0/G_1$ phase of the cell cycle and produces a notable delay in pancreatic cancer cell growth [41], but does not induce apoptosis [39]. Gemcitabine and 5-FU are cytotoxic and induce programmed cell death [9, 27, 30]. Therefore, the cytostatic action of OGF could be envisioned to channel cells into the apoptotic pathway associated with gemcitabine or 5-FU.

Gemcitabine is the standard of care for metastatic cancer [7, 13, 17, 24, 42], and is in clinical trials as a single-agent chemotherapeutic for locally advanced pancreatic cancer [1]. Treatment with gemcitabine is not curative for metastatic disease, and treatment with this agent as to its palliative benefit must be examined in the face of such factors as toxicity [1, 17]. Given the urgent need for advancement in the treatment of pancreatic cancer, combinations of drug therapies, many of which involve a new agent plus gemcitabine, for pancreatic cancer have gained attention [5, 7, 17, 24]. The present report raises the exciting potential of combining chemotherapy and biotherapy into a novel treatment modality for human pancreatic cancer. OGF is not toxic, avoids problems related to drug resistance, has easy accessibility, and can be integrated into the chronic use of chemotherapeutic agents. Moreover, it introduces the possibility of using chemotherapeutic agents at less toxic concentrations and/or in chronic regimens (metronomic chemotherapy) [see 10, 16] in combination with a biotherapy. OGF used as a single-agent has been successful in a Phase I clinical trial with patients with advanced unresectable pancreatic adenocarcinoma [33]. During the chronic experiments in this study by Smith and colleagues [33], mean survival from the time of diagnosis was 8.7 to 9.5 months, depending on the route of drug administration, with some patients living as long as 23 months. With the preclinical information in this report showing that a combination of OGF and gemcitabine has marked effects on pancreatic cancer in tissue culture and in xenografts, and the data from the Phase I clinical trial with OGF reporting a lack of toxicity and suggesting efficacy, the prospect of clinical studies using combination drug therapy with OGF and gemcitabine appears to be warranted.

The observations in this study showing that the combination of OGF with gemcitabine has a potent inhibitory action on human pancreatic cancer, both in vitro and in vivo, are consistent with reports for OGF in combination with chemotherapy for treatment of squamous cell carcinoma of the head and neck (SCCHN) [14, 19]. Using tissue culture, McLaughlin and colleagues [19] demonstrated that OGF in combination with either paclitaxel or carboplatin has a profound repressive influence on the growth of SCCHN. Jaglowski et al. [14] has reported that OGF in combination with paclitaxel markedly inhibited tumor growth in xenografts of SCCHN. In both in vitro and in vivo investigations, the combination of OGF and chemotherapy was greater than that for the individual compounds. In addition to pancreatic [38, 44] and SCCHN [19-21], OGF has been shown to influence the growth (in vitro and/or in vivo) of a wide variety of cancers including neuroblastoma [22], renal cancer [2], and colon cancer [37]. These data indicate that combined chemotherapy (e.g., gemcitabine, paclitaxel) and biotherapy (OGF) for a variety of cancers is likely.

REFERENCES

1. Akerele C E, Rybalova I, Kaufman H L, Mani S (2003) Current approaches to novel therapeutics in pancreatic cancer. Invest New Drugs 21:113-129
2. Bisignani, G J, McLaughlin P J, Ordille S D, Beltz M S, Jarowenko M V, Zagon I S (1999) Human renal cell cancer proliferation in tissue culture is tonically inhibited by opioid growth factor. J. Urology 162:2186-2191
3. Buchsbaum D J, Bonner J A, Grizzle W E, Stackhouse M A, Carpenter M, Hicklin D J, Bohlen P, Raisch K P (2002) Treatment of pancreatic cancer xenografts with Erbitux (IMC-C225) anti-EGFR antibody, gemcitabine, and radiation. Int J Radiation Oncol Biol Phys 54:1180-1193
4. Burris H A, Moore M J, Andersen J, Green M R, Rothenberg M L, Modiano M R, Cripps M C Portenoy R K, Storniolo A M, Tarassof P, Nelson R, Dorr F A, Stephens C D, von Hoff D D (1997) Improvements in survival and clinical benefit with gemcitabine as first-line therapy for patients with advanced pancreatic cancer. A randomized trial. J Clin Oncol 15:2403-2413
5. Corrie P, Mayer A, Shaw J, D'Ath S, Blagden S, Blesing C, Price P, Warner N (2002) Phase II study to evaluate combining gemcitabine with flutamide in advanced pancreatic cancer patients. Brit J Cancer 87:716-719

6. Di Paolo A, Danesi R, Del Tacca M (2004) Pharmacogenetics of neoplastic diseases: New trends. Pharmacol Res 49:331-342
7. Diaz-Rubio E (2004) New chemotherapeutic advances in pancreatic, colorectal, and gastric cancers. Oncologist 9:282-294
8. Faivre S, Raymond E, Woynarowski J M, Cvitkovic E (1999) Supraadditive effect of 2',2''-difluorodeoxycitidine (gemcitabine) in combination with oxaliplatin in human cancer cell lines. Cancer Chemother Pharmacol 44:117-123
9. Fueger B J, Hamilton G, Raderer M, Pangerl T, Traub T, Angelberger P, Baumgartner G, Dudczak R, Virgolini I (2001) Effects of chemotherapeutic agents on expression of somatostatin receptors in pancreatic tumor cells. J Nuclear Med 42:1856-1862
10. Gasparini G (2001) Metronomic scheduling: The future of chemotherapy. Lancet Oncol 2:733-740
11. Hertel L W, Boder G B, Kroin J S, Rinzel S M, Poore G A, Todd G C, Grindey G B (1990) Evaluation of the antitumor activity of gemcitabine (2'2'-difluoro-2'-deoxycytidine). Cancer Res 50:4417-4422
12. Huang P, Chubb S, Hertel L, Grindley G B, Plunkett W (1991) Action of 2',2'-difluorodeoxycitine on DNA synthesis. Cancer Res 51:6110-6117
13. Jacobs A D (2002) Gemcitabine-based therapy in pancreas cancer. Cancer Supplement 85:923-927
14. Jaglowski J R, Zagon I S, Stack B C, Verderame M F, Leure-duPree A E, Manning J D, McLaughlin P J (2005) Opioid growth factor (OGF) enhances tumor growth inhibition and increases the survival of paclitaxel-treated mice with squamous cell carcinoma of the head and neck. Cancer Chemother Pharmacol, in press
15. Jemal A, Tiwari R C, Murray T, Ghafoor A, Samuels A, Ward E, Feuer E J, Thun M J (2004) Cancer statistics. CA Cancer J Clin 54:8-29
16. Kerbel R S, Klement G, Pritchard K I, Kamen B (2002) Continuous low-dose anti-angiogenic/metronomic chemotherapy: From the research laboratory into the oncology clinic. Ann Oncol 13:73-80
17. Li D, Xie K, Wolff R, Abbruzzese (2004) Pancreatic cancer. Lancet 363:1049-1057
18. Lieber M, Mazzetta J, Nelson-Rees W, Kaplan M, Todaro G (1975) Establishment of a continuous tumor-cell line (PANC-1) from a human carcinoma of the exocrine pancreas. Int J Cancer 15:741-747
19. McLaughlin P J, Jaglowski J R, Verderame M F, Stack B C, Leure-duPree A E, Zagon I S (2005) Enhanced growth inhibition of squamous cell carcinoma of the head and neck by combination therapy of paclitaxel and opioid growth factor. Int J Oncol, in press
20. McLaughlin P J, Levin R J, Zagon I S (1999) Regulation of human head and neck squamous cell carcinoma growth in tissue culture by opioid growth factor. Int J Oncol 14:991-998
21. McLaughlin P J, Levin R J, Zagon I S (2003) Opioid growth factor (OGF) inhibits the progression of human squamous cell carcinoma of the head and neck transplanted into nude mice. Cancer Letters 199:209-217
22. McLaughlin P J, Zagon I S, Skitzki J (1999). Human neuroblastoma cell growth in tissue culture is regulated by opioid growth factor. Int J Oncol 14:373-380
23. Parkin D M, Pisani P, Ferlay J (1999) Global cancer statistics. CA Cancer J Clin 49:33-64
24. Pasetto L M, Jirillo A, Stefani M, Monfardini S (2004) Old and new drugs in systemic therapy of pancreatic cancer. Crit. Rev Oncology/Hematology 49:135-151
25. Philip P A (2002) Gemcitabine and platinum combinations in pancreatic cancer. Cancer 95:908-911
26. Ryan D P, Kulke M H, Fuchs C S, Grossbard M L, Grossman S R, Morgan J A, Earle C C, Shivdasani R, Kim H, Mayer R J, Clark J W (2002) A phase II study of gemcitabine and docetaxel in patients with metastatic pancreatic carcinoma. Cancer 94:97-103
27. Schniewind B, Christgen M, Kurdow R, Haye S, Kremer B, Kalthoff H, Ungefroren H (2004) Resistance of pancreatic cancer to gemcitabine treatment is dependent on mitochondria-mediated apoptosis. Int J Cancer 109:182-188
28. Schultz R M, Merriman R L, Toth J E, Zimmermann J E, Hertel L W, Andis S L, Dudley D E, Rutherford P G, Tanzer L R, Grindey G B (1993) Evaluation of new anticancer agents against the MIA PaCa-2 and PANC-2 human pancreatic carcinoma xenografts. Oncol Res 5:223-228
29. Schwarz R E, McCarty T M, Peralta E A, Daimond D J, Ellenhorn J D (1999) An orthotopic in vivo model of human pancreatic cancer. Surgery 126:562-567
30. Shi X, Liu S, Kleeff J, Friess H, Buchler M W (2002) Acquired resistance of pancreatic cancer cells towards 5-fluorouracil and gemcitabine is associated with altered expression of apoptosis-regulating genes. Oncol 62:354-362
31. Shim W S N, Teh M, Mack P O P, Ge R (2001) Inhibition of angiopoietin-1 expression in tumor cells by antisense RNA approach inhibited xenograft tumor growth in immunodeficient mice. Int J Cancer 94:6-15
32. Shore S, Raraty G T, Ghaneh P, Neoptolemos J P (2003) Review article: Chemotherapy for pancreatic cancer. Aliment Pharmacol Ther 18:1049-1069
33. Smith J P, Conter R L, Bingaman S I, Harvey H A, Mauger D T, Ahmad M, Demers L M, Stanley W B, McLaughlin P J, Zagon I S (2004) Treatment of advanced pancreatic cancer with opioid growth factor: Phase I. Anti-Cancer Drugs 15:203-209
34. Warshaw A L, Fernandez-del Castillo C (1992) Pancreatic carcinoma. N Eng J Med 326:455-465
35. Yip-Schneider M T, Sweeney C J, Jun S-H, Crowell P L, Marshall M S (2001) Cell cycle effects of nonsteroidal anti-inflammatory drugs and enhanced growth inhibition in combination with gemcitabine in pancreatic carcinoma cells. J Pharmacol Exp Therap 298:976-985
36. Yunis A A, Arimura G K, Russin D J (1977) Human pancreatic carcinoma (MIA PaCa-2) in continuous culture: Sensitivity to asparaginase. Int J Cancer 19:128-135
37. Zagon I S, Hytrek S D, Lang C M, Smith J P, McGarrity T J, Wu Y, McLaughlin P J (1996) Opioid growth factor ([Met$^5$]-enkephalin) prevents the incidence and retards the growth of human colon cancer Amer J Physiol 271:R780-786
38. Zagon I S, Hytrek S D, Smith J P, McLaughlin P J (1997) Opioid growth factor (OGF) inhibits human pancreatic cancer transplanted into nude mice. Cancer Letters 112:167-175
39. Zagon I S, McLaughlin P J (2003) Opioids and the apoptotic pathway in human cancer cells. Neuropeptides 37:79-88
40. Zagon I S, McLaughlin P J (2004) Opioid growth factor (OGF) inhibits anchorage-independent growth in human cancer cells. Int J Oncol 24:1443-1448
42. Zagon I S, Roesener C D, Verderame M F, Ohlsson-Wilhelm B M, Levin R J, McLaughlin P J (2000) Opioid growth factor regulates the cell cycle of human neoplasias. Int J Oncol 17:1053-1061

43. Zagon I S, Smith J P (2004) Treatment options in pancreatic cancer. Hospital Pharmacy Europe November/December:1-2
44. Zagon I S, Smith J P, Conter R, McLaughlin P J (2000) Identification and characterization of opioid growth factor receptor in human pancreatic adenocarcinoma. Int J Mol Med 5:77-84
45. Zagon I S, Smith J P, McLaughlin P J (1999) Human pancreatic cancer cell proliferation in tissue culture is tonically inhibited by opioid growth factor. Int J Oncol 14:577-584
46. Zagon I S, Verderame M F, Allen S S, McLaughlin P J (2000) Cloning, sequencing, chromosomal location, and function of a cDNA encoding the opioid growth factor receptor (OGFr) in humans. Brain Res 856:75-83

TABLE 6

Incidence and latency for tumor appearance of MIA PaCa-2 pancreatic carcinoma cells in nude mice treated with OGF and/or gemcitabine (Gemzar).

| Parameter | Control | OGF | Gemzar | Gemzar/ OGF |
|---|---|---|---|---|
| N | 10 | 10 | 12 | 12 |
| Tumor Incidence, day 10 | 8/10 | 6/10 | 9/12 | 0/10[a] |
| Tumor Incidence, day 16 | 10/10 | 10/10 | 11/12 | 9/12 |
| Latency to visible tumor, d | 10.1 ± 1.8 | 10.7 ± 0.8 | 11.1 ± 1.1 | 16.2 ± 1.2* |
| Latency to measurable tumor, d | 13.2 ± 1.8 | 14.2 ± 0.8 | 13.1 ± 1.0 | 19.5 ± 1.1* |

Values represent means ± SEM.
[a]Significantly different from every group by Chi-square analyses at $p < 0.001$.
Significantly different from controls at $p < 0.05$ (*) using ANOVA.

TABLE 7

Characteristics of nude mice 45 days after subcutaneous inoculation of MIA PaCa-2 pancreatic cancer cells and treatment with OGF and/or gemcitabine (Gemzar)

| Parameter | Controls | OGF | Gemzar | Gemzar/ OGF |
|---|---|---|---|---|
| Body Weight, g | 33.3 ± 1.0 | 31.4 ± 1.6 | 27.4 ± 0.55 | 30.6 ± 0.7 |
| Tumor Weight, g | 5.5 ± 1.0 | 3.5 ± 0.5* | 2.4 ± 0.1*** | 0.8 ± 0.1***++^ |
| Tumor Volume, mm$^3$ | 8935 ± 1694 | 4849 ± 490*** | 3963 ± 123*** | 1477 ± 53***+^ |
| Spleen Weight, mg | 761 ± 61 | 606 ± 121 | 454 ± 49* | 437 ± 62* |

Data represent means ± SEM.
Significantly different from controls at $p < 0.05$ (*) and $p < 0.001$(***).
Significantly different from OGF group at $p < 0.05$ (+) and $p < 0.01$ (++).
Significantly different from the Gemzar-treated mice at $p < 0.05$ (^).

EXAMPLE 8

This study evaluated the effects of a combination of Opioid Growth Factor (OGF) and paclitaxel on squamous cell carcinoma of the head and neck (SCCHN) using a tissue culture model of human SCCHN. The combination of OGF and paclitaxel was markedly inhibitory to SCCHN proliferation, reducing growth from control levels by 48% to 69% within 48 hr. OGF in combination with carboplatin also depressed cell growth. The effect of a combination of OGF and paclitaxel or carboplatin on SCCHN growth was supra-additive, being greater than either of the individual compounds. The action of OGF, but not paclitaxel, was mediated by a naloxone-sensitive receptor and was completely reversible. OGF, but no other endogenous or exogenous opioid, altered replication of SCCHN. OGF and paclitaxel depressed DNA synthesis, whereas only paclitaxel induced apoptosis. The combination of OGF and paclitaxel also had a supra-additive effect on the growth of another SCCHN, CAL-27, indicating the ubiquity of the combined drug activity. These data suggest that the combination of a biotherapy (OGF) and chemotherapy (paclitaxel, carboplatin) may provide an enhanced antitumor action with respect to SCCHN.

Given the promising nature of OGF (biotherapy), and of paclitaxel (chemotherapy), as antitumor agents in SCCHN, and the lack of preclinical data regarding the simultaneous use of OGF and paclitaxel, the present study was designed to explore the therapeutic potential of a combination of these modalities. Using a tissue culture model of the UM-SCC-1 cell line (SCC-1) derived from a well-differentiated recurrent squamous cell carcinoma in the floor of the mouth, the effect of concomitant exposure to both OGF and paclitaxel were characterized on growth (e.g., reversibility, receptor mediation, specificity) and mechanism of action (apoptosis, necrosis, and cell proliferation).

Materials and Methods

Cell Line and Cell Proliferation Assays.

The UM-SCC-1 cell line (SCC-1) was derived from a well-differentiated recurrent squamous cell carcinoma in the floor of the mouth of a 73-yr old male (25). This cell line was obtained from The University of Michigan, Cancer Research Laboratory (Thomas E. Carey, Ph.D., Director). CAL-27 human squamous cell carcinoma cell line, derived from a poorly differentiated carcinoma of the tongue in a 56-yr old male (26), was obtained from the American Type Culture Collection (Manassas, Va.). Both cell lines were grown in Dulbecco's MEM (modified) media supplemented with 10% fetal calf serum, 1.2% sodium bicarbonate, and antibiotics (5,000 Units/ml penicillin, 5 mg/ml streptomycin, 10 mg/ml neomycin). The cell cultures were maintained in a humidified atmosphere of 7% $CO_2$/93% air at 37° C.

Cells were seeded at equivalent amounts into either 6-well or 96-well plates (Falcon) and counted 24 hr later to determine plating efficiency. OGF ($10^{-6}$ M) and/or paclitaxel ($10^{-8}$M), or sterile water were added beginning 24 hr after seeding (=0 hr); media and compounds were replaced daily. OGF was prepared in sterile water and paclitaxel was dissolved in DMSO at a concentration of $10^{-2}$M and further diluted into sterile water; dilutions represent final concentrations of the compounds. The concentration of OGF that was utilized was selected based on previous evidence demonstrating growth inhibition of SCCHN (13); the concentration of paclitaxel was selected from preliminary studies in our laboratory demonstrating that paclitaxel at $10^{-8}$ M, but not $10^{-7}$ M, inhibited cell growth but did not eliminate all cells over a 5-6 day period of time (15).

Some experiments examined the effects of carboplatin and OGF. Dosages of $10^{-7}$M carboplatin and/or $10^{-6}$ M OGF were utilized. The dosage of carboplatin selected was based on previous reports (27, 28), as well as preliminary studies in our laboratory.

Cell number was recorded either by using the MTS proliferation bioassay (Cell Titer 96 One Solution, Promega, Madison, Wis.) and measuring absorbency after 4 hr on a Biorad (Model 3550) plate reader at 490 nm with a 750 nm background absorbance screening, or by directly counting cells. The MTS assay utilized 10 wells/treatment. For manual counts, cells were harvested by trypsinization with 0.25% trypsin/0.53 mM EDTA, centrifuged, and counted with a hemacytometer. Cell viability was determined by trypan blue staining. At least two aliquots per well, and 4-10 wells/treatment, were counted at each time for manual counting.

For some experiments, the rate of growth over a 96-hr period of time was calculated using linear regression analyses. The slopes of the lines (number of cells/hr) were compared by analysis of variance. All calculations were performed with GraphPad Prism software.

DNA Synthesis, Apoptosis and Necrosis.

To begin to determine the mechanisms of action of paclitaxel and/or OGF, the effects of these drugs on DNA synthesis (BrdU incorporation), apoptosis (caspase-3 activity), and necrosis (trypan blue positivity) were evaluated. To examine DNA synthesis, SCC-1 cells were seeded onto 22 mm diameter coverglasses placed in 6-well plates ($3 \times 10^3$ cells/coverglass). Cells were treated with paclitaxel ($10^{-8}$ M) and/or OGF ($10^{-6}$ M) for 24 or 72 hr; media and drugs were replaced daily. Three hours prior to fixing cells, 30 µM BrdU was added to cultures. At appropriate times, cells were rinsed, fixed in 10% neutral buffered formalin, and stained with antibodies to BrdU (Roche, Indianapolis, Ind.). The number of positive cells was recorded using fluorescence microscopy. At least 1000 cells/treatment at each time were counted.

Caspase-3-FITC positive staining was used to characterize early stages of apoptosis (29). SCC-1 cells were seeded into 6-well plates and treated with drugs beginning 24 hr later; drugs and media were replaced daily. Cells were harvested after 1, 3 and 6 days of drug treatment, and prepared according to manufacturer's recommendations for FACS analysis (FACS cell sorter with a 15 mW argon ion laser at 488 nm; Becton, Dickinson and Company, Franklin Lakes, N.J.). For caspase-3 identification, the APO-ACTIVE 3 antibody detection kit (Cell Technology, Mountain View, Calif.) was used. Three samples from each treatment were analyzed at each time point. The percent gated cells recorded by flow cytometry was considered caspase positive.

Chemicals.

All chemicals and drugs were purchased from Sigma Chemicals (St. Louis, Mo.).

Statistical analyses.

Cell numbers and/or absorbencies were analyzed using analysis of variance (one- or two-factor where appropriate) (ANOVA) with subsequent comparisons made using Newman-Keuls tests.

Results

Growth Assays with Paclitaxel and OGF.

Figure 17A:
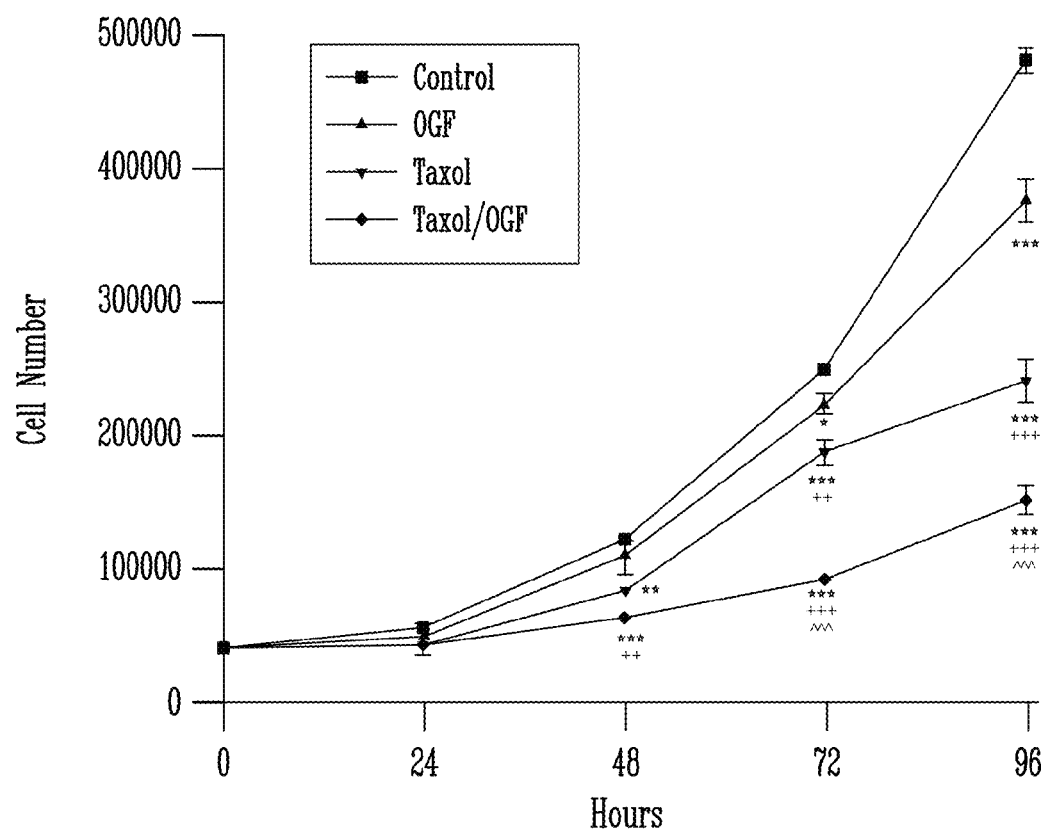
FIG. 17A shows growth (cell number determined by a hemacytometer) of SCC-1 cells subjected to OGF ($10^{-6}$ M) and/or paclitaxel ($10^{-8}$ M) (=Taxol) over a 96-hr period. Drugs or an equivalent volume of sterile water (Control) were added 24 hr after seeding 100,000 cells into 6-well plates; media and drugs were replaced daily. Growth curve data represent means±SE for at least 4 wells/treatment at each time point. Significantly different from controls at $p<0.05$ (*), $p<0.01$ (), and $p<0.001$ (*). Significantly different from OGF-treated cultures at $p<0.01$ (++) and $p<0.001$ (+++). Significantly different from paclitaxel-treated cultures at $p<0.001$ (^^^).

To establish the efficacy of the combination of paclitaxel and OGF on growth of SCCHN, and to contrast this with the effects of the individual drugs, growth curves of SCC-1 cells were generated. Experiments on the growth of SCCHN were evaluated by either cell counting or the MTS assay, and these methods were comparable indicating that either technique was appropriate for analysis. Growth curves are presented in FIG. 17A, and the rates of growth obtained from the slopes of the growth curves (number of cells/hr) are presented in FIG. 17B. After 48 hr of drug treatment, OGF or paclitaxel reduced cell number by approximately 10% (not significant) and 33% ($p<0.01$), respectively, from control levels. However, the combination of OGF and paclitaxel reduced cell number by 48% ($p<0.001$) suggesting a synergistic effect of these drugs. At 72 and 96 hr in culture, OGF significantly reduced cell number from control values by 10% and 23%, respectively, whereas paclitaxel reduced cell number by 25% and 51%, respectively. Exposure of SCC-1 cells for 72 and 96 hr to both drugs resulted in subnormal cell numbers, with a significant ($p<0.001$) decrease from control levels of 63% and 69%, respectively, being recorded. At 72 hr, the effect of both drugs (OGF and paclitaxel) displayed a synergistic effect on growth. Cells exposed to both OGF and paclitaxel had markedly fewer cells than in comparison to cultures exposed to either the OGF or paclitaxel alone at 72 and 96 hr, and from the OGF group at 48 hr.

Figure 17B:
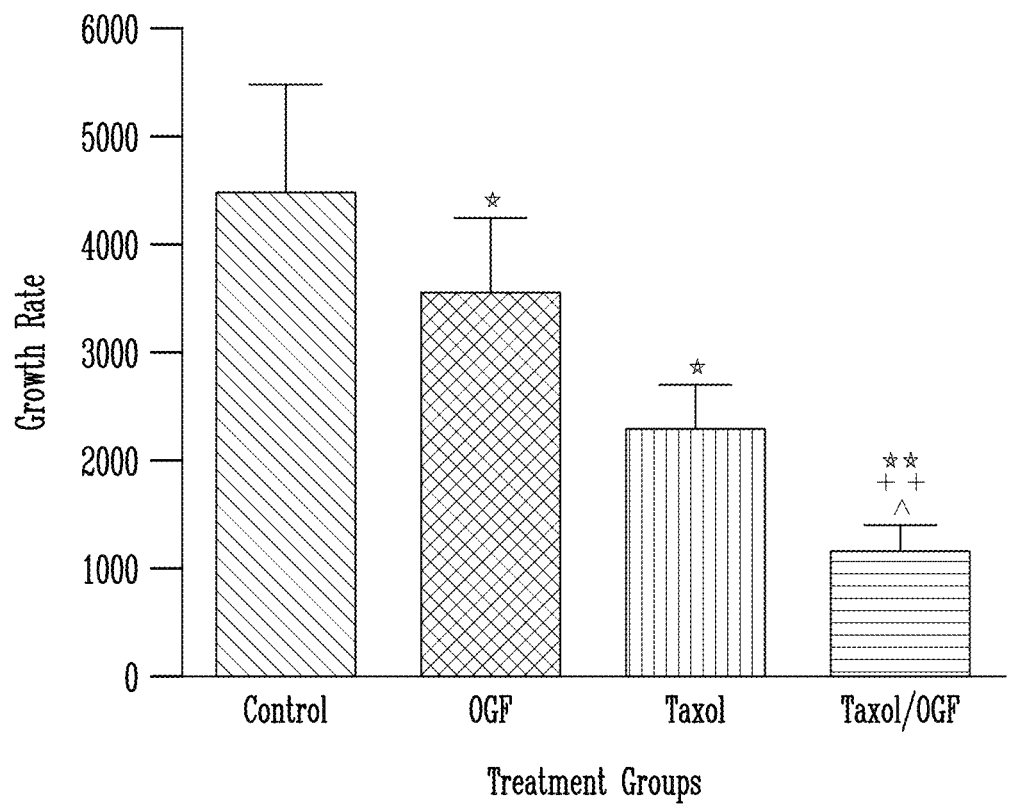
FIG. 17B shows rates of growth calculated from overall slopes of the growth curves shown in FIG. 17A. Data represent the slopes (number of cells/hr) of the curves±SE. Significantly different from controls at $p<0.05$ (*) and $p<0.01$ (**). Growth rates for the cells treated with combined therapy also differed from OGF-treated cells at $p<0.01$ (++), and from cells subjected to paclitaxel alone at $p<0.05$ (^).

Rates of growth over the 4 day period of time were analyzed, and the results demonstrated that cell growth for OGF and for paclitaxel were notably reduced from control values ($p<0.01$) (FIG. 17B). Moreover, cells treated with a combination of OGF and paclitaxel had a growth rate that was significantly decreased from both the OGF and paclitaxel groups at $p<0.01$ and $p<0.05$, respectively.

Growth Assays with Carboplatin and OGF.

Figure 18:
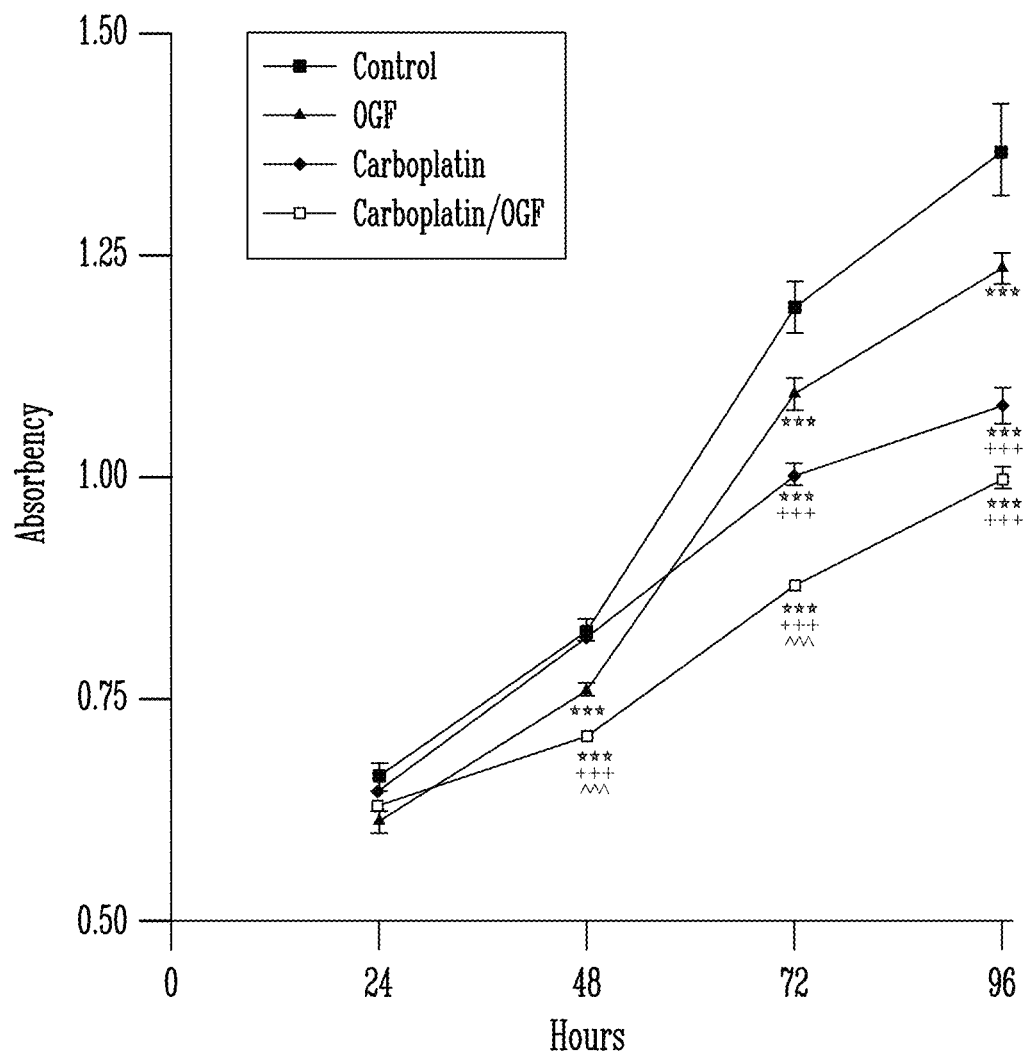
FIG. 18 depicts growth of SCC-1 cells treated with carboplatin and/or OGF as measured by the MTS assay. Values represent mean absorbencies±SE for 10 wells at each time point. Significantly different from controls at $p<0.001$ (***). Significantly different from OGF-treated cultures at $p<0.001$ (+++). Significantly different from carboplatin-treated cultures at $p<0.001$ (^^^).

To inquire whether other agents used in the treatment of SCCHN have a heightened response in combination with OGF, growth studies with carboplatin and OGF were performed (FIGS. 18). At 48, 72, and 96 hr of drug exposure, OGF reduced cell number by 8-10% from control levels, whereas carboplatin reduced cell number at 72 and 96 hr by 19% and 21%, respectively. The combination of OGF and carboplatin reduced cell number relative to control values by 14-27% in the 48-96 hr time period. Exposure of SCC-1 cells to both OGF and carboplatin reduced cell number from the OGF group by approximately 7-20% at 48-96 hr, and from the group treated with carboplatin alone by approximately 14% and 12% at 48 and 72 hr, respectively.

Opioid Receptor Mediated Effects of OGF and/or Paclitaxel.

Figure 19:
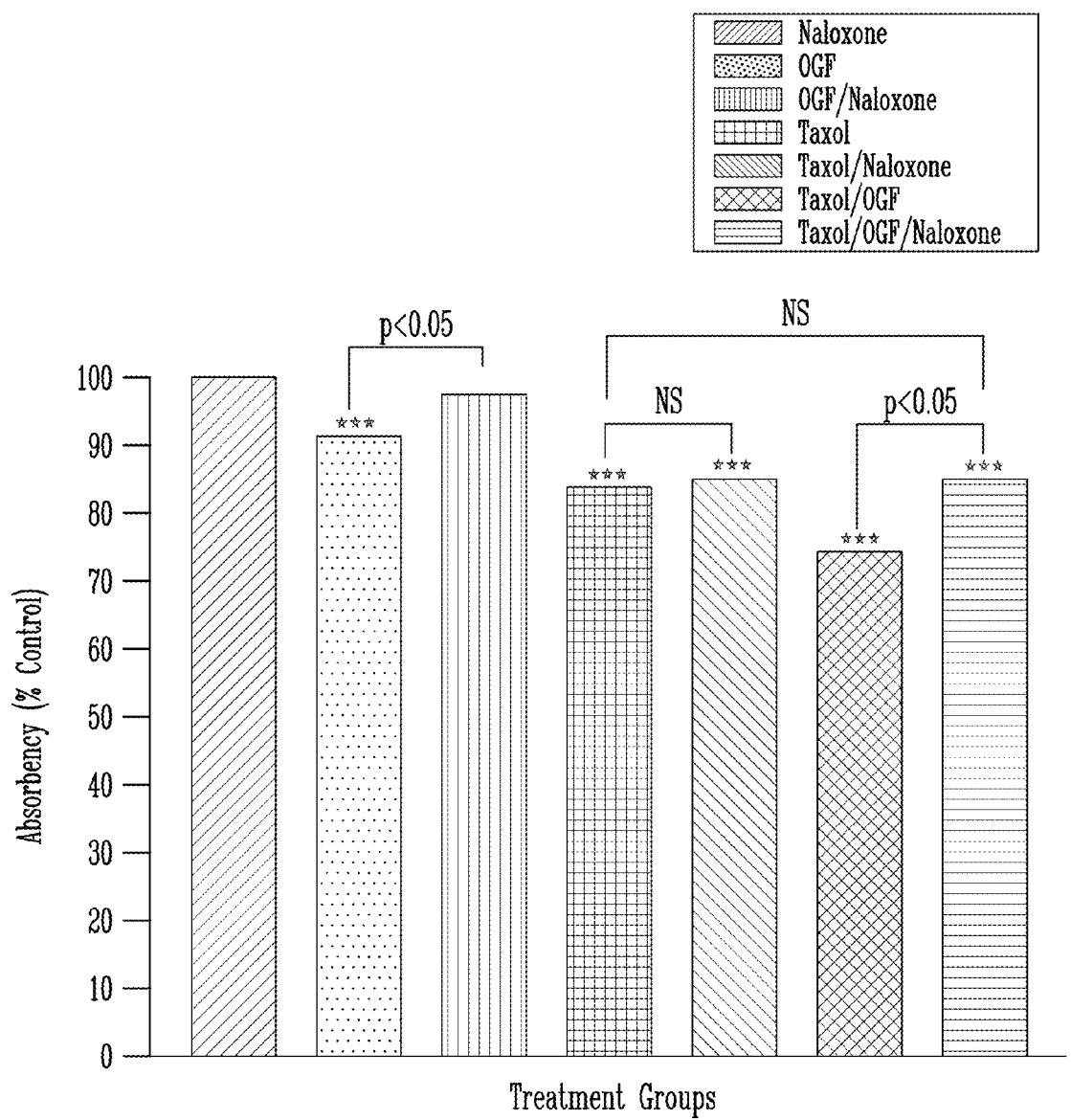
FIG. 19 shows OGFr mediation of the growth inhibitory effects of paclitaxel and/or OGF in SCC-1 cells. The number of SCC-1 cells at 96 hr as measured by the MTS assay after being subjected to OGF ($10^{-6}$ M), the opioid antagonist naloxone ($10^{-6}$ M), paclitaxel (Taxol) ($10^{-8}$ M), or combinations of these compounds; controls were treated with an equivalent volume of sterile water. Compounds and media were replaced every 24 hr. Data represent mean absorbency±SE for 10 wells/treatment. Significantly different from controls at $p<0.001$ (***). NS=not significant.

In order to determine whether the effects of OGF and/or paclitaxel were mediated by an opioid receptor, some cultures were exposed to naloxone ($10^{-6}$ M), a short-acting opioid antagonist. Cells were seeded into 96-well plates and treated with $10^{-6}$M OGF, $10^{-6}$ M naloxone, $10^{-8}$ M paclitaxel, or combinations at the same concentrations—OGF/naloxone, paclitaxel/naloxone, paclitaxel/OGF, and paclitaxel/OGF/naloxone. Individual plates were read at 24, 48, 72, and 96 hr after drug addition. Relative to control levels, addition of OGF, paclitaxel, paclitaxel/OGF, and paclitaxel/OGF/naloxone inhibited cell growth from 8.8% to 26.0% (FIG. 19). Addition of naloxone completely blocked the growth inhibitory effects of OGF alone, but had no effect on the growth inhibitory action of paclitaxel alone. Moreover, naloxone partially neutralized the enhanced inhibitory effect of the combination of paclitaxel and OGF; cell number of the paclitaxel/OGF/naloxone group was comparable to cells exposed to paclitaxel, but was significantly reduced from control levels. Naloxone alone, at the concentration utilized, had no effect on growth.

Reversibility of the Inhibitory Growth Effects of OGF and/or Paclitaxel.

Figure 20:
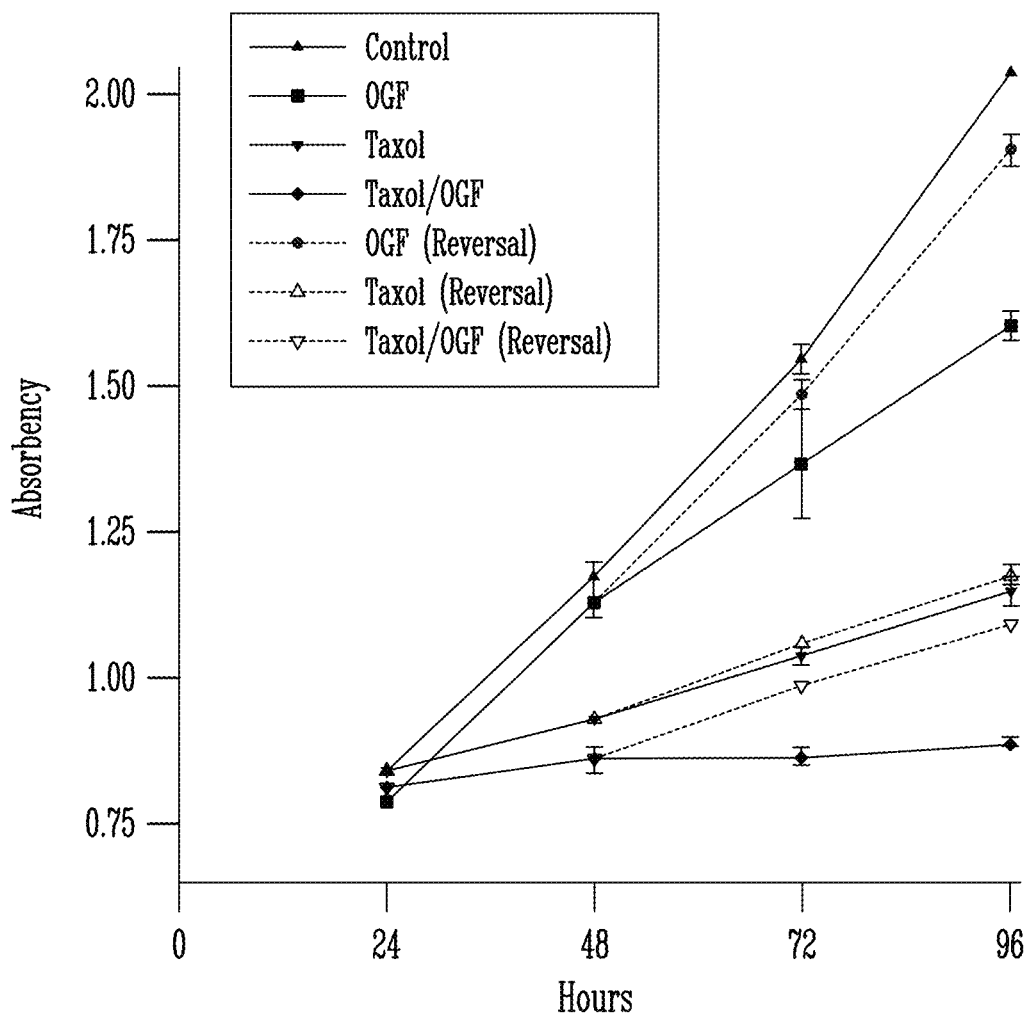
FIG. 20 depicts the growth of SCC-1 cells treated with a variety of endogenous and exogenous opioids. Data represent mean absorbency values±SE for 10 wells/treatment. Significantly different from controls at $p<0.001$ (***).

To establish whether the effect of OGF and/or paclitaxel on growth could be reversed by withdrawing cells from drug exposure, cultures of SCC-1 cells were exposed for 48 hr to $10^{-6}$M OGF, $10^{-8}$ M paclitaxel, or paclitaxel/OGF. After 2 days, half of the plates had media removed and fresh media added with no additional OGF or paclitaxel (i.e., OGF-reversal; paclitaxel-reversal; paclitaxel/OGF-reversal groups);

some cultures continued to receive new media and drugs. Within 48 hr, the OGF-reversal group had 16% more cells than the OGF group continuing with OGF exposure, however the paclitaxel-reversal group did not differ from cells continuing to be treated with paclitaxel (FIG. 20A, B). Cell cultures exposed to the combination of OGF and paclitaxel had significantly fewer cells than cultures treated with OGF or paclitaxel alone, as well as the combination of these drugs withdrawn after 48 hr. The paclitaxel/OGF-reversal group did not differ from the paclitaxel alone or paclitaxel-reversal groups.

Specificity of Opioid Peptide(s) Related to Head and Neck Cancer Cell Growth.

Figure 21:
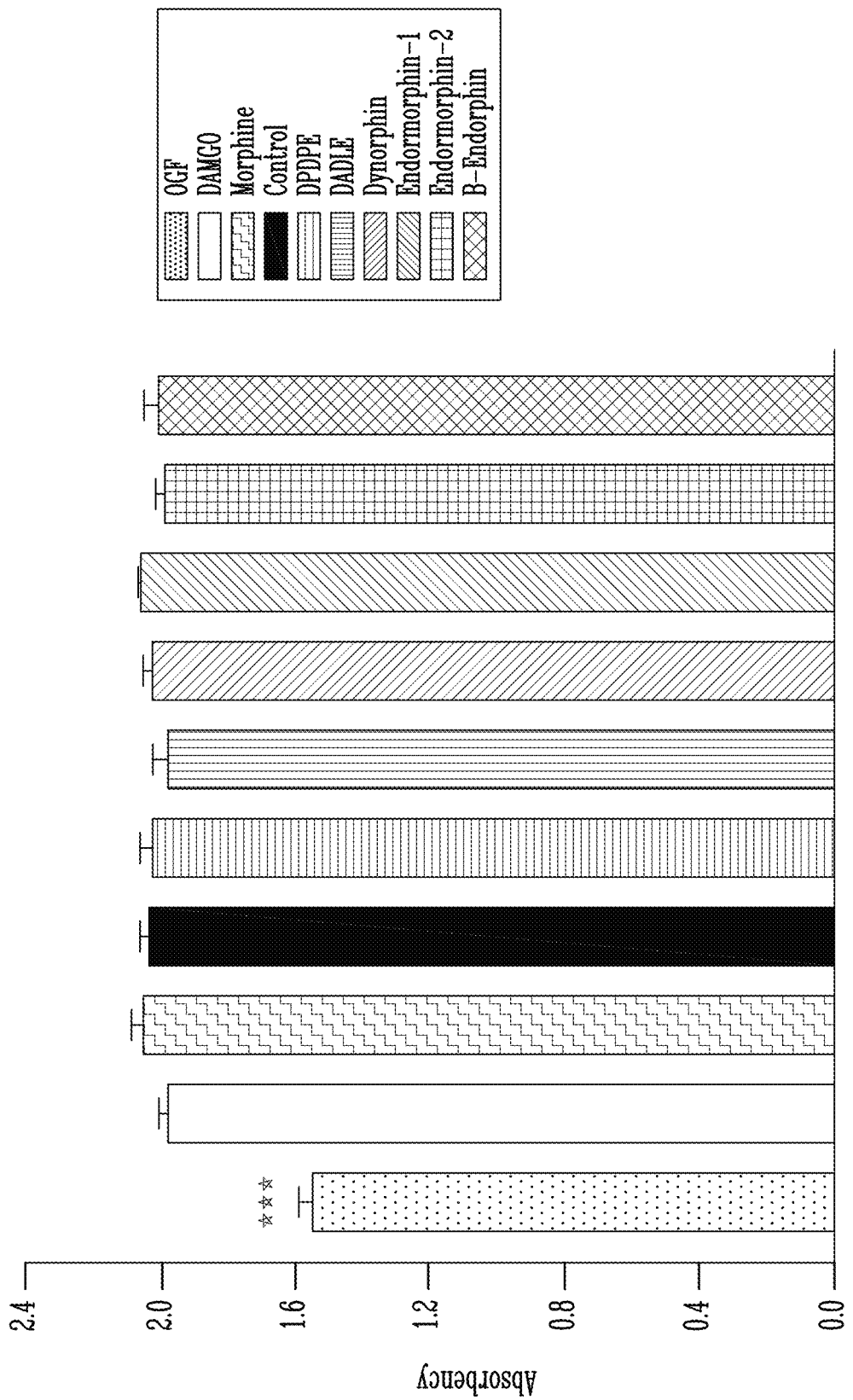
FIG. 21 shows the evaluation of apoptosis in SCC-1 cells treated with OGF and/or paclitaxel for 24, 72, to 144 hours. Cells were seeded into 6-well plates, treated with drugs and, at appropriate times, stained with caspase-3. Caspase-3 activity was measured by flow cytometry on 10,000 cells/treatment/time. Data represent the percent caspase positive cells (mean±SE) for 3 samples for each treatment at each time point. Significantly different from controls at $p<0.001$ (***) and from OGF at $p<0.001$ (+++). Cells exposed to the combined therapy also differed from paclitaxel treated cells at $p<0.001$ (^^^).

To determine whether other opioid peptides are related to growth, SCC-1 cultures (1000 cells/well) were treated daily with $10^{-6}$ M concentrations of a variety of natural and synthetic opioid ligands (FIG. 21); in some cases, these ligands were specific for μ, δ, or κ opioid receptors. Drugs included OGF, morphine, DAMGO, DPDPE (d-Pen,d-Pen-enkephalin), DADLE (d-Ala-D-Leu-enkephalin), dynorphin 1-13, endomorphin-1, endomorphin-2, and (3-endorphin. Except for OGF, which had a 19% decrease from control levels in absorbency readings, none of the drugs utilized had any inhibitory or stimulatory effect on growth.

Programmed Cell Death.

Figure 22:
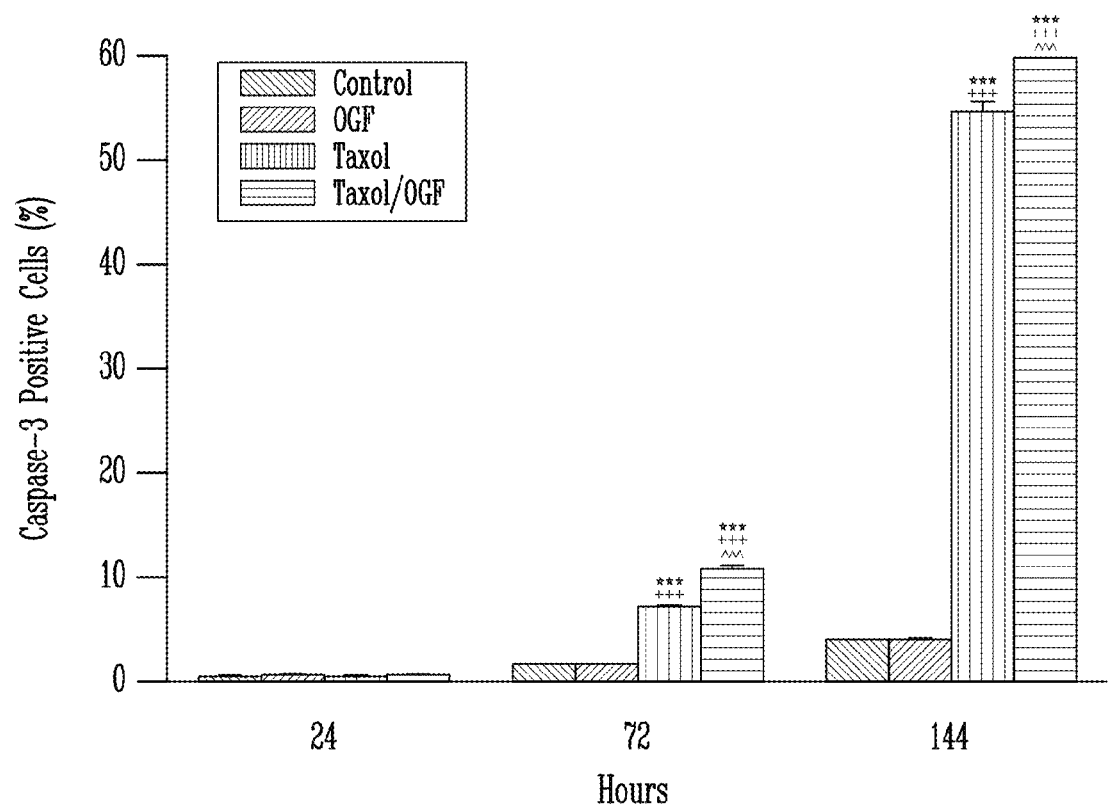
FIG. 22 shows the evaluation of DNA synthesis by monitoring BrdU incorporation in SCC-1 cells treated with OGF and/or paclitaxel for 24 hr or 72 hr. Data represent the percent BrdU positive cells (mean±SE) from analysis of at least 1000 cells for each treatment at each time point. Significantly different from controls at $p<0.05$ (*), $p<0.01$ (), and $p<0.001$ (*), and from the OGF group at $p<0.001$ (+++).

No differences in necrosis could be observed in analysis of the number of trypan blue positive cells in cultures or supernatants of control cells and those treated with OGF and/or paclitaxel. Examination of apoptosis was conducted by measurement of caspase-3 product (FIG. 22). Using flow cytometry, the percentages of caspase-3 positive cells after one day of treatment with OGF and/or paclitaxel were negligible. However, within 3 days of exposure to paclitaxel or a combination of OGF and paclitaxel, there were 3.4- and 5.6-fold more caspase positive cells than in control cultures. At 6 days in culture, there were 12.7- and 13.9-fold more caspase reactive cells treated with paclitaxel or OGF and paclitaxel, respectively, than in control cultures. No change from control levels in caspase reactivity could be recorded in cells exposed to OGF on days 3 or 6.

BrdU Incorporation into SCC-1 Cells.

Figure 23:
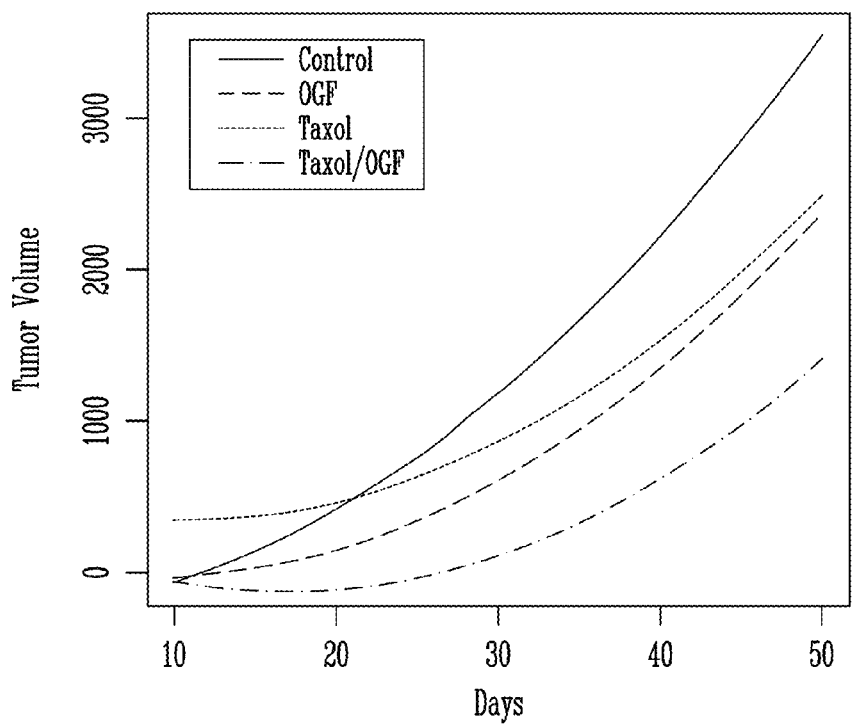
FIG. 23 shows changes in tumor volume over the 50 days of the experiment analyzed using a non-linear mixed effects model for clustered data. These analyses were performed to accommodate the marked loss of paclitaxel mice beginning on day 20. Tumor volumes of mice in all 3 treatment groups were significantly ($p<0.001$) smaller than controls. Moreover, tumor volumes for mice receiving combined therapy were significantly ($p<0.001$) smaller than tumor sizes in groups receiving either treatment alone. Animals were given intraperitoneal injections of either sterile saline (0.1 ml; Control) daily, OGF (10 mg/kg) daily, paclitaxel (8 mg/kg; Taxol) every other day, or paclitaxel every other day and OGF daily (Taxol/OGF).

BrdU labeling of SCCHN cells for 3 hours and treatment for 24 hours with OGF, paclitaxel, or OGF and paclitaxel showed a 31%, 24%, and 33%, respectively, decrease in the number of positive cells relative to controls (FIG. 23). After 3 days of drug treatment, the number of BrdU positive cells was decreased 61% from control levels in the OGF-treated cultures. The number of BrdU labeled cells was reduced 24% and 16% from control levels in the paclitaxel or paclitaxel-OGF treated cultures, respectively.

Ubiquity of Paclitaxel and OGF Effects on Growth of SCCHN.

Figure 24:
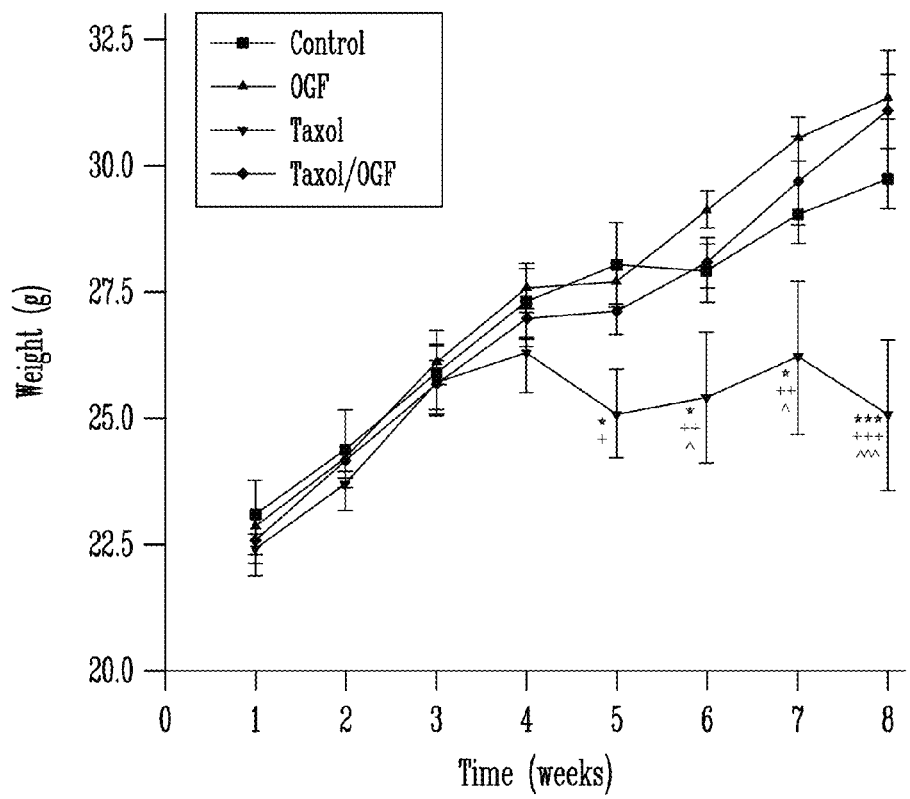
FIG. 24 shows body weights of mice treated with either OGF (10 mg/kg, daily) and/or paclitaxel (8 mg/kg every 2 days; Taxol); control animals received 0.1 ml sterile saline (Control). Body weights were recorded every 7 days; values represent means±SEM. No significant differences in body weights between Control, OGF, or Taxol groups were recorded. Significantly different from control group at $p<0.05$ (*) and $p<0.001$ (***), from the OGF group at $p<0.01$ (++) and $p<0.001$ (+++), and from the Taxol/OGF group at $p<0.05$ (^) and $p<0.001$ (^^^).

To determine the ubiquity of the supra-additive effect of OGF and paclitaxel in contrast to either drug alone, the poorly-differentiated SCCHN—CAL-27—was investigated (FIG. 24). Log-phase cultures of CAL-27 were initially exposed to various concentrations of paclitaxel ($10^{-7}$ M to $10^{-10}$ M) in order to evaluate the sensitivity of these cells to this agent. After 48 hr in culture (drug and media changed daily), treatment with paclitaxel at concentrations of $10^{-7}$, $10^{-8}$, $10^{-9}$, and $10^{-10}$ M depressed growth at 66%, 53%, 44%, and 22% from control levels. A dosage of $10^{-10}$ M paclitaxel was chosen for further study in order to examine the magnitude of the combination of OGF and paclitaxel in the face of a lower level of toxicity. After 48 hr, exposure of CAL-27 cells to either OGF ($10^{-6}$ M), paclitaxel ($10^{-10}$ M), or OGF ($10^{-6}$ M) and paclitaxel ($10^{-10}$ M) revealed 25%, 35%, and 61%, respectively, fewer cells than in control cultures. These differences in cell growth with exposure to OGF and/or paclitaxel differed significantly (p<0.001) from control levels, and the combination of OGF and paclitaxel differed from the OGF and the paclitaxel treated cultures at p<0.001 and p<0.01, respectively.

Discussion

Data generated in this study demonstrate that the combination of OGF and paclitaxel has a potent inhibitory effect on the growth of 2 cell lines of SCCHN in tissue culture. The antigrowth action of OGF and paclitaxel was supra-additive, with the total inhibitory activity being greater than the sum of the parts (i.e., OGF or paclitaxel alone). The repressive effects on growth of SCCHN observed with OGF and with paclitaxel individually were consonant with previous results (e.g., 13, 30, 31). The action of OGF on cell growth were mediated by a naloxone-sensitive receptor. This naloxone-sensitive receptor is presumed to be OGFr, because synthetic and natural opioids selective for classical opioid receptors such as μ, δ, and κ did not influence cell replication of SCC-1 as demonstrated in the present report and earlier (13, 22). OGF also was found to have a reversible action on the replication of SCC-1, supporting the results from earlier studies showing that treatment with this compound does not lead to cytotoxicity and cell death (13, 21). On the other hand, the effects of paclitaxel on SCC-1 cells were neither blocked by naloxone nor could be reversed, indicating that the characteristics of this drug's action on SCC-1 is markedly different from that of OGF. Thus, this is the first report of the efficacy of using a combination of the biotherapeutic agent, OGF, and the chemotherapeutic agent, paclitaxel, to retard the growth of SCCHN.

Although this report focused on the effects of OGF and paclitaxel on SCC-1 cells for detailed study, it is known that OGF, and paclitaxel, influence the growth of a variety of SCCHN cell lines (13, 32). The present investigation demonstrates that not only does OGF and paclitaxel have a supra-additive inhibitory effect on the SCC-1 cell number, but a similar action can be found with another SCCHN cell line, CAL-27. Thus, the combination of OGF and paclitaxel appears to have more than a singular effect on one SCCHN line, and has a potent inhibitory action on the growth of both well-differentiated (SCC-1) (25) and poorly-differentiated (CAL-27) (26) SCCHN. Thus, it is reasonable to conclude that the effects of combination therapy with OGF and paclitaxel observed herein also extend to other SCCHN cell lines.

Paclitaxel is a chemotherapeutic agent that prevents microtubule depolymerization resulting in the arrest of proliferating cells in the $G_2$-M phase of the cell cycle and leading to cell death (33, 34). Additionally, paclitaxel modulates a number of intracellular events which result in cellular apoptosis and ensuing nuclear degradation (35). OGF is known to not influence apoptosis (21), but is targeted to the $G_0/G_1$ phase of the cell cycle (17). Our experiments showed that SCCHN exposed to paclitaxel resulted in a marked increase in the number of apoptotic cells within 3 days of initiation of drug treatment. By 6 days of drug exposure, over one-half the SCCHN cells were apoptotic. OGF had no effect on apoptosis of SCCHN, but produced a significant reduction in the number of cells undergoing the S phase of DNA synthesis. Therefore, the mechanism for the enhancement by the combined effect of OGF and paclitaxel as to growth inhibition could be related to delays in the cell cycle (the effect of OGF) which results in the recruitment of cells into the apoptotic pathway (the effect of paclitaxel).

To address the question whether OGF could be combined with agents other than taxols in order to treat SCCHN, a preliminary study was conducted with the combination of OGF and a platinum analogue: carboplatin. Carboplatin causes a cross-linking of DNA strands by intercalation and the creation of a bifunctional covalent link that in turn interrupts DNA synthesis during the S phase of the cell cycle (36-38). This drug has been shown to exhibit cytotoxicity through the induction of apoptosis (39, 40). The present results are the first to show that the effects of a combination of carboplatin and OGF has potent inhibitory properties with respect to SCCHN. However, unlike the case for the taxanes and OGF which revealed a supra-additive action with OGF and paclitaxel, OGF and carboplatin had an additive effect on growth. Presumably, these results indicate that OGF could be used in combination with more than one family of chemotherapeutic agents (i.e., taxanes, platinums) to enhance antitumor activity. Further studies are needed to characterize the mode of action of a combination of these two drugs. The end result may be that OGF is a cytostatic drug, whereas paclitaxel and carboplatin induce programmed cell death, and that OGF contributes to cell death by channeling cells into the apoptotic pathway. Paclitaxel has been reported to be active in the treatment of squamous cell carcinoma of the head and neck, and Phase II evaluation has been successful (6). Used as a single-agent therapy for SCCHN, this drug improved response rate, as well as median survival time, in comparison to cisplatin and 5-fluorouracil combination chemotherapy. However, 91% of the patients exposed to paclitaxel experienced neutropenia. Although OGF has been approved in Phase I trials (41), OGF has not been used clinically for the treatment of SCCHN. However, the efficacy of this compound has been demonstrated in xenograft experiments (14, 16). The present report raises the exciting potential of combining chemotherapy and biotherapy into a novel treatment modality for SCCHN.

REFERENCES

1. Jemal A, Tiwari R C, Murray T, Ghafoor A, Samuels A, Ward E, Feuer E J, and Thun M J: Cancer statistics. CA Cancer J Clin 54:8-29, 2004.
2. Parkin D M, Pisani P and Ferlay J: Global cancer statistics. CA Cancer J Clin 49: 33-64, 1999.
3. Carew J F and Shah J P: Advances in multimodality therapy for laryngeal cancer. CA Cancer Clin 48: 211-228, 1998.
4. Schantz S, Harrison L B and Forastiere A A: Tumors of the nasal cavity and paranasal sinuses, nasopharynx, oral cavity, and oropharynx. In: VT DeVita, S Hellman and S A Rosenberg (eds.), Cancer Principles and Practice of Oncology, 5th edition, pp. 741-801. Philadelphia: Lippincott-Raven, 1997.
5. Shah J P and Lydiatt W: Treatment of cancer of the head and neck. CA-Cancer J. Clin. 45: 352-368, 1995.
6. Forastiere A A, Shank D, Neuberg D, Taylor S G, DeConti R C and Adams G: Final report of a phase II evaluation of paclitaxel with advanced squamous cell carcinoma of the head and neck: An Eastern Cooperative Oncology Group trial (PA390). Cancer 82: 2270-2274, 1998.
7. Leyvraz S, Ohnuma T, Lassus M and Holland J F: Phase I study in patients with advanced cancer, intermittent intravenous bolus, and 24-hour infusion. J Clin Oncol 3: 1385-1392, 1985.
8. Shin D M, Khuri F R, Glisson B S, Ginsberg L, Papadimitrakopoulou V M, Clayman G, Lee J J, Ang K K, Lippman S M and Hong W K: Phase II study of paclitaxel, ifosafamide, and carboplatin in patients with recurrent or metastatic head and neck squamous cell carcinoma. Cancer 91: 1316-1323, 2001.
9. Vokes E E, Haraf D J, Stenson K, Stupp R, Malone D, Levin J and Weichselbaum R R: The role of paclitaxel in the treatment of head and neck cancer. Sem Oncol 22: 8-12, 1995.
10. Hussain M, Gadgeel S, Kucuk O, Du W, Salwen W and Ensley J: Paclitaxel, cisplatin, and 5-fluorouracil for patients with advanced or recurrent squamous cell carcinoma of the head and neck. Cancer 86: 2364-2369, 1999.
11. Coughlin C T and Richmond R C: Biological and clinical developments of cisplatin combined with radiation: concepts, utility, projections for new trials, and the emergence of carboplatin. Sem Oncol 16: 31-43, 1989.
12. Vermorken J B, ten Bokkek Huinik W W and Eisenhauwer E A: Carboplatin versus cisplatin. Ann Oncol 4: 41-48, 1993.
13. McLaughlin P J, Levin, R J and Zagon I S: Regulation of human head and neck squamous cell carcinoma growth in tissue culture by opioid growth factor. Int J Oncol 14: 991-998, 1999
14. McLaughlin P J, Levin R J and Zagon I S: Opioid growth factor (OGF) inhibits the progression of human squamous cell carcinoma of the head and neck transplanted into nude mice. Cancer Letters 199: 209-217, 2003.
15. McLaughlin P J, Jaglowski J R, Stack B C and Zagon I S: Enhanced antitumor activity of paclitaxel on SCCHN with opioid growth factor (OGF): In vitro studies. FASEB J 18:A997.
16. McLaughlin P J, Stack B C, Braine K M, Ruda J D and Zagon I S: Opioid growth factor (OGF) inhibition of a human squamous cell carcinoma of the head and neck in nude mice: Dependency on the route of administration. Int J Oncol 24: 227-232.
17. Zagon I S, Roesener C D, Verderame M F, Ohlsson-Wilhelm B M, Levin R J and McLaughlin P J: Opioid growth factor regulates the cell cycle of human neoplasias. Int J Oncol 17: 1053-1061, 2000.
18. Zagon I S, Wu Y and McLaughlin P J: Opioid growth factor (OGF) inhibits DNA synthesis in mouse tongue epithelium in a circadian-rhythm-dependent manner. Am J Physiol 267: R645-R652.
19. Zagon I S, Wu Y and McLaughlin P J: Opioid growth factor and organ development in rat and human embryos. Brain Res 839: 313-322, 1999.
20. Wilson R P, McLaughlin P J, Lang C M and Zagon I S: The opioid growth factor, [Met$^5$]-enkephalin, inhibits DNA synthesis during recornification of mouse tail skin. Cell Proliferation 33: 63-73, 2000.
21. Zagon I S and McLaughlin P J: Opioids and the apoptotic pathway in human cancer cells. Neuropeptides 37: 79-88, 2003
22. McLaughlin P J, Levin R J and Zagon I S: The opioid growth factor receptor (OGFr) in human head and neck squamous cell carcinoma. Int J Mol Med 5:191-196, 2000.
23. Levin R J, Wu Y, McLaughlin P J and Zagon I S: Expression of the opioid growth factor, [Met$^5$]-enkephalin, and the zeta opioid receptor in head and neck squamous cell carcinoma. Laryngoscope 107:335-339, 1997.
24. McLaughlin P J, Stack B C, Levin R J, Fedok F and Zagon I S: Defects in the OGF receptor (OGFr) in human squamous cell carcinoma of the head and neck. Cancer 97: 1701-1710, 2003.
25. Krause C J, Carey T E, Ott R W, Hurbis C, McClatchey K D and Regezi J A: Human squamous cell carcinoma. Arch Otolaryngol 107: 703-710, 1981.
26. Gioanni J, Fischel J-L, Labert J-C Demard F, Mazeau C, Zanghellini E, Ettore F, Formento P, Chavel P, Lalanne C-M and Courdi A: Two new human tumor cell lines derived from squamous cell carcinomas of the tongue: establishment, characterization and response to cytotoxic treatment. Eur J Cancer Clin Oncol 24:1445-1455, 1988.
27. Saikawa Y, Kubota T, Kuo T H, Tamino H, Kase S, Furukawa T, Watanabe M, Ishibiki K, Kitajima M and Hoffman R M: Combined effect of 5-fluorouracil and carboplatin against human gastric cancer cell lines in vitro and in vivo. Anticancer Res 14: 461-464, 1994.
28. Takizawa M, Fukuda S, Yokohama M, Miyatake Y and Inuyama Y: An experimental study of the combined effect of radiotherapy and chemotherapy on head and neck squamous cell carcinoma cell line. Auris Nasus Larynx 28: S83-S86, 2001.
29. Kuwahara D, Tsutsumi K, Kobayashi T, Hasunuma T and Nishioka K: Caspase-9 regulates cisplatin-induced apoptosis in human head and neck squamous cell carcinoma cells. Cancer Letters 148: 65-71, 2000.
30. Elomaa L, Joensuu H, Kulmala J, Lemi P and Grenman R: Squamous cell carcinoma is highly sensitive to taxol, a possible new radiation sensitizer. Acta Otolaryngol (Stockholm) 115: 340-344, 1995.
31. Pulkkinen J O, Elomaa L, Joensuu H, Martikainen P, Serveomaa K and Grenman R: Paclitaxel-induced apoptotic changes followed by time-lapse videomicroscopy in cell lines established from head and neck cancer. J Cancer Res Clin Oncol 122: 214-218, 1996.
32. Leonard C E, Chan D C, Chou T-C, Kumar R and Bunn P A: Paclitaxel enhances in vitro radiosensitivity of squamous carcinoma cell lines of the head and neck. Cancer Res 56: 5198-5204, 1996.
33. Schiff P B and Horwitz S B: Taxol stabilizes microtubules in mouse fibroblast cells. Proc Natl Acad Sci USA 77: 1561-1565, 1980.
34. Schiff P B, Fant J and Horwitz S B: Promotion of microtubule assembly in vitro by taxol. Nature 277: 665-667, 1979.
35. Srivastava R K, Srivastava A R, Korsmeyer S J, Nesterova M, Cho-Chung Y S and Longo D L: Involvement of microtubules in the regulation of Bcl2 phosphorylation and apoptosis through cyclic AMP-dependent protein kinase. Mol Cell Biol 18: 3509-3517, 1998.
36. Ainser J, Sinibaldi V and Eisenberger M: Carboplatin in the treatment of squamous cell head and neck cancers. Sem Oncol 19: 60-65, 1992.
37. Coleman S C, Stewart Z A, Day T A, Netterville J L, Burkey B B and Pietnepol J A: Analysis of cell-cycle checkpoint pathways in head and neck cancer cell lines: Implications for therapeutic strategies. Arch Otolaryngol—Head Neck Surg 128: 167-176, 2002.
38. Engbloom P, Rantanen V, Kulmala J, Heenius J and Grenman S: Additive and supra-additive cytotoxicity of cisplatin-taxane combinations in ovarian carcinoma cell lines. Brit J Cancer 79: 286-292, 1999.
39. Itoh M, Chiba H, Noutomi T, Takada E and Mizuguchi J: Cleavage of Bax-$\alpha$ and Bcl-$x_L$ during carboplatin-mediated apoptosis in squamous cell carcinoma cell line. Oral Oncol 36: 277-285, 2000.
40. Mishima K, Nakiai Y and Yoshimura Y: Carboplatin induces FAS (APO-1/CD95) dependent apoptosis of human tongue carcinoma cells: Sensitization for apoptosis by upregulation of FADD expression. Int J Cancer 105: 593-600, 2003.
41. Smith J P, Conter R L, Bingaman S I, Harvey H A, Mauger D T, Ahmad M, Demers L M, Stanley W B, McLaughlin P J and Zagon I S: Treatment of advanced pancreatic cancer with opioid growth factor: Phase I. Anti-Cancer Drugs 15: 203-209, 2004.

EXAMPLE 9

The present report addresses the question of whether a combination of OGF and paclitaxel influences growth of human SCCHN in vivo, and does so beyond the efficacy of each compound. The effects of OGF and/or paclitaxel on tumor incidence, appearance, size and metastasis, and on the binding characteristics of the OGF receptor, were examined in a xenograft model of SCCHN using human SCC-1 cells.

Material and Methods

Cell Lines

The UM-SCC-1 cell line (SCC-1) [8] was obtained from Cancer Research Laboratory at The University of Michigan (Dr. Thomas E. Carey, Director). Cells were grown in Dulbecco's MEM (modified) media supplemented with 10% fetal calf serum, 1.2% sodium bicarbonate, and antibiotics (5,000 Units/ml penicillin, 5 mg/ml streptomycin, 10 mg/ml neomycin). The cell cultures were maintained in a humidified atmosphere of 7% $CO_2$/93% air at 37° C. Cells were harvested by trypsinization with 0.05% trypsin/0.53 mM EDTA, centrifuged, and counted with a hemacytometer. Cell viability was determined by trypan blue staining Animals and Tumor Cell Implantation Male 4 week old nu/nu nude mice purchased from Harlan Laboratories (Indianapolis, Ind.) were housed in pathogen-free isolators in the Department of Comparative Medicine at the Penn State University College of Medicine. All procedures were approved by the IACUC committee of the Penn State University College of Medicine and conformed to the guidelines established by NIH. Mice were allowed 48 hr to acclimate prior to beginning experimentation.

Tumor cells were inoculated into nude mice by subcutaneous injection into the right scapular region. Subcutaneous injections were performed with at least $2 \times 10^6$ cells per mouse; mice were not anesthetized for this procedure.

Chemotherapeutic Administration

Four groups of mice (n=12) were randomly assigned to receive intraperitoneal injections of 10 mg/kg OGF daily, 8 mg/kg paclitaxel every other day; 10 mg/kg OGF daily and 8 mg/kg paclitaxel every other day, or 0.1 ml of sterile saline daily. In the group receiving combined therapy, OGF was injected prior to paclitaxel. Dosages were selected based on published reports [1, 17]. Paclitaxel was dissolved in DMSO and then diluted in sterile saline; OGF was dissolved in sterile saline. Injections of drugs were initiated 1 hr after tumor cell inoculation. Preliminary studies were performed to determine whether DMSO alone altered tumor response by injecting mice with 0.1 ml DMSO daily; no differences in tumor growth were found between injections of saline or DMSO thus data were combined for analyses. Mice were weighed weekly to determine drug dosage.

Tumor Growth and Metastases

Mice were observed daily for the presence of tumors. The latency for a visible tumor to appear, and the time until tumors were measurable (i.e., 62.5 mm³), were recorded. Tumors were measured using calipers every day. Tumor volume was calculated using the formula $w^2 \times 1 \times \pi/6$, where the length is the longest dimension, and width is the dimension perpendicular to length [24].

Termination Day Measurements

According to institutional policies and IACUC guidelines, mice were terminated when tumors became ulcerated, or tumors grew to 2 cm in diameter. Fifty 50 days following tumor cell inoculation and approximately 35-40 days following initial tumor appearance, all mice were euthanized by an overdose of sodium pentobarbital (100 mg/kg) and killed by cervical dislocation; mice (with tumors) were weighed.

Tumors and spleens were removed and weighed, and the lymph nodes, liver, and spleen examined for metastases.

Receptor Binding Analyses

Tumor tissues from some mice in each treatment group were removed at the time of death, washed free of blood and connective tissue, and immediately frozen in liquid nitrogen. Tissues were assayed following the procedures published previously [16]. Saturation binding isotherms were generated using GraphPad Prism software; binding affinity ($K_d$) and capacity ($B_{max}$) values were provided by the computer software.

Plasma Levels of OGF

At the time of termination, trunk blood was collected from several mice in each group. Plasma was separated and OGF levels were measured by standard radioimmunoassay procedures using a kit from Peninsula Laboratories (Belmont, Calif.). Plasma samples were assayed in duplicate.

Statistical Analyses

Incidence of tumors was analyzed by chi-square tests. Latency for tumor appearance and tumor volume were analyzed using analysis of variance (ANOVA) with subsequent comparisons made using Newman-Keuls tests. Growth of tumors, termination day data (i.e., body weight, tumor weight, spleen weight), plasma levels of OGF, as well as binding capacity and affinity of tumors, were compared by ANOVA and Newman-Keuls tests.

Survival data of the nude mice were analyzed using Kaplan-Meier plots. Tumor growth was analyzed using a non-linear mixed effects model for clustered data.

Results

SCC-1 Tumor Appearance and Growth

On day 13, when 75% of the mice in the saline-injected control group had measurable tumors, 33% of the mice receiving OGF had a tumor; these values differed significantly at p<0.05 (Table 8). Although fewer mice in the paclitaxel and paclitaxel/OGF groups (66% and 70%, respectively) had measurable tumors compared to controls, these differences were not statistically significant. On day 17 when 100% of the control mice had measurable tumors, only 66% of the mice receiving OGF had tumors, and 83% and 90% of the animals in the paclitaxel and paclitaxel/OGF groups, respectively, had tumors; however, no significant differences were recorded (Table 9). All mice inoculated with SCC-1 cells developed tumors (Table 8), with 100% of the mice in the control group having tumors by day 17 and every animal in the other groups having a measurable tumor by day 28. The latency time for mice receiving OGF to develop visible tumors was 11 days in comparison to controls that had a mean latency of 7 days; this four-day delay was significantly different at p<0.02 (Table 8). The mean latency time for visible tumors to appear was comparable between mice in the control group and in the paclitaxel and paclitaxel/OGF groups. The mean latency time until tumors became measurable ranged from 14 to 17 days, and did not differ between groups.

Figure 25:
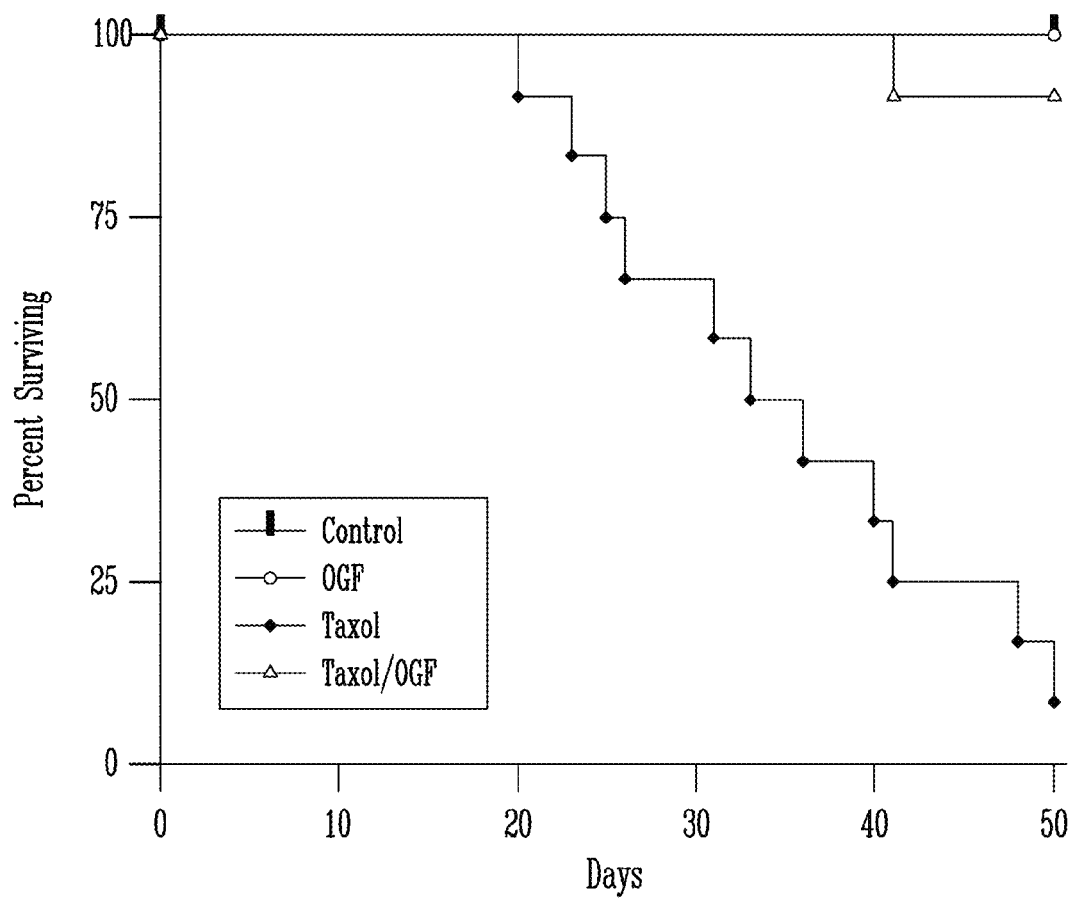
FIG. 25 shows the survival curves of mice inoculated with $2 \times 10^6$ SCC-1 squamous cells of the head and neck and treated with either OGF (10 mg/kg, daily) and/or paclitaxel (8 mg/kg every 2 days; Taxol); control animals received 0.1 ml sterile saline (Control). Kaplan-Meier curves were analyzed and the survival of mice receiving only paclitaxel was significantly different from all other groups at $p<0.001$.

Changes in tumor volume over the 50 days of the experiment were analyzed using a non-linear mixed effects model for clustered data (FIG. 25). These analyses compensated for the marked loss of paclitaxel mice beginning on day 20. Tumor volumes of mice in all 3 treatment groups were significantly smaller than controls. Moreover, tumor volumes for mice receiving combined therapy were significantly smaller than tumor sizes in groups receiving either treatment alone.

The weights of tumors on termination day (day 50) in the OGF and the paclitaxel/OGF groups were reduced 29% and 62%, respectively, from control levels (Table 9). Evaluation of tumor volume on day 50 revealed the OGF and paclitaxel/ OGF groups had a reduction of 33% and 69%, respectively, from control values (Table 9). Because only one mouse in the paclitaxel group was alive at this timepoint, analysis of tumor weight or volume were performed. Measurements of tumor weight and volume in the paclitaxel/OGF group on day 50 also revealed a decrease of 47% and 53%, respectively, from that occurring in the OGF group.

Survival

Survival curves for mice in each group are presented in FIG. 27. Two of twelve mice receiving paclitaxel/OGF died within one week of initiation of the experiment; the cause(s) of these deaths appeared unrelated to tumor development or the process of injection (e.g., ulceration). Mice receiving paclitaxel began dying within 20 days of treatment. By day 40, 75% of the mice receiving paclitaxel had died, and at day 50 only one mouse in this group was alive. One mouse in the paclitaxel/OGF group died on day 42. No mouse in the OGF or control groups died during the experimental period. Statistical comparisons of the survival curves revealed that death rates for paclitaxel mice were statistically reliable (p<0.0001) from all other groups. The average life span for paclitaxel mice was 34.3±3.1 days in comparison to the 50-day life span of other mice (day 50=termination day), and this difference was statistically significant from all 3 groups (p<0.001).

Body Weights and Gross Observations

Although all mice weighed approximately 22-23 g at the beginning of the experiment (FIG. 26), mice receiving paclitaxel had a 10% reduction in body weight at week 5 of the study and were subnormal by 9-10% on weeks 6 and 7. On the termination date (i.e., day 50), mice receiving paclitaxel weighed 28% less than control subjects, and were significantly less (p<0.001) in body weight than mice in the OGF and paclitaxel/OGF groups (Table 9). No differences in body weights between control animals and those in the OGF or paclitaxel/OGF groups were recorded.

Gross observations of the mice in the paclitaxel group revealed distended abdomens, impacted bowel, and severe body weight loss. Pathological reports indicated colonic dilation and peritonitis; all other organ systems appeared normal. No pathological relevant findings could be detected for mice in the control, OGF, or paclitaxel/OGF groups.

Spleen weights did not differ among groups. In addition, no metastases were noted in the spleens, liver, or axillary lymph nodes of mice in any group.

OGFr Binding Characteristics

Specific and saturable binding for OGFr, with a one-site model of binding, was recorded in tumors collected from all 4 groups of mice. Tumors from the paclitaxel group were obtained at days 47 to 50, whereas specimens from all other groups were harvested on the final day of experimentation (day 50). Binding affinity ($K_d$) for OGF to OGFr ranged from 1.0 to 2.1 nM and did not differ among groups (Table 10). However, values for binding capacity ($B_{max}$) were almost 2-fold higher in the OGF and paclitaxel group relative to control subjects (~15 fmol/mg protein) (Table 10).

Plasma Levels of OGF

OGF levels in the plasma of nude mice bearing SCC-1 tumors ranged from 282 to 617 pg/ml. No differences were noted between control mice with tumors and those treated with OGF, paclitaxel, or paclitaxel/OGF.

Discussion

The present results show that a combination of OGF and paclitaxel has a potent inhibitory effect on the growth of SCC-1 in nude mice, a well-differentiated human tumor model of SCCHN. The antigrowth action of OGF and paclitaxel was synergistic, with the total inhibitory activity being greater than the sum of the parts (i.e., OGF or paclitaxel alone). This supra-additive effect of OGF and paclitaxel was most evident in measurements of tumor weight and volume. These results performed under in vivo conditions extend earlier observations conducted in tissue culture [13] in which a combination of OGF and paclitaxel had a synergistic repressive effect on cell number. Thus, this is the first report of the efficacy of using a combination of the biotherapeutic agent, OGF, and the chemotherapeutic agent, paclitaxel, to retard the growth of SCCHN in vivo. Although this study focused on one SCCHN cell model, SCC-1, it is known that OGF, and paclitaxel, influence the growth of a variety of SCCHN cell lines [10, 14]. Therefore, it is reasonable to conclude that the effects of combination therapy with OGF and paclitaxel observed herein also extend to other SCCHN cell lines.

An important observation recorded in the present investigation was the well-known [7, 28] marked systemic toxicity from paclitaxel which was manifested in significant reductions in body weight and survival, as well as gross lesions and pathological signs, and the attenuation of this toxicity by simultaneous administration of OGF. However, the amelioration of paclitaxel toxicity by OGF was not accompanied by a diminution in the antitumor action of paclitaxel. In fact, the combination of OGF and paclitaxel had an effect on tumor growth (i.e., weight, volume) that exceeded paclitaxel alone (or OGF alone). These results would suggest that chemotherapeutic levels of paclitaxel were better tolerated and compatible with survival when given concomitantly with the biotherapeutic agent, OGF. The alleviation of toxicity of one agent by administration of another drug is not without precedence [3, 9]. In and by itself, the finding of protection afforded by OGF from the side effects produced by taxanes is important. However, the combination of OGF and paclitaxel could allow even higher cytostatic doses of paclitaxel to be administered in order to improve the therapeutic efficacy of this agent. Indeed, the success of chemotherapeutic agents is often limited by an intrinsic resistance of the cancer cells, and the availability of increasing the concentration of drugs like paclitaxel without an accompanying increase in toxicity would be advantageous. Finally, it is unclear as to whether the effectiveness of a combination of OGF and paclitaxel is animal specific and/or is due to the lack of immune components in nude mice. Because myelosuppression is a main side effect of chemotherapy it would be valuable to explore the immunological ramifications of OGF/paclitaxel therapy in the understanding of drug mechanism.

Previous studies have shown that surgical specimens of SCCHN have significantly fewer OGF receptors than normal mucosa [18]. Translation/posttranslation of OGFr protein rather than irregularities in OGFr gene transcription may be involved in this decrease in receptor number. These authors postulate that the number of OGF receptors may be dependent on tumor size, and that the progressive diminishment in OGF receptors in SCCHN compromises the inhibitory activity of OGF and thereby contributes to an accelerated cell proliferation. In the present investigation, tumor tissue from animals treated with OGF or paclitaxel and inoculated with SCCHN had over a 2-fold greater binding capacity than neoplastic tissue from control subjects. And, although not statistically significant, even those animals receiving a combination of paclitaxel and OGF had an increase of 38% in binding capacity. If the hypothesis put forth by McLaughlin and colleagues [17] is correct, it would be understandable that the smaller SCCHN tumors in OGF and/or paclitaxel mice would have more OGF receptors (and grow slower) than those in control mice because of the repressed cell replication and less impaired OGF-OGFr axis.

Paclitaxel is a chemotherapeutic agent that prevents microtubule depolymerization resulting in the arrest of proliferating cells in the $G_2$-M phase of the cell cycle which leads to cell death [31, 32]. Additionally, paclitaxel modulates a number of intracellular events which result in cellular apoptosis and ensuing nuclear degradation [27]. OGF does not influence apoptosis [31], but is targeted to the $G_0/G_1$ phase of the cell cycle [32]. Earlier experiments in tissue culture showed that SCCHN exposed to paclitaxel resulted in a marked increase in the number of apoptotic cells. Therefore, the mechanism for the enhanced growth inhibition in vivo by the combined effect of OGF and paclitaxel could be related to delays in the cell cycle (the effect of OGF) which results in the recruitment of cells into the apoptotic pathway (the effect of paclitaxel).

Paclitaxel has been reported to be active in the treatment of squamous cell carcinoma of the head and neck, and Phase II evaluation has been successful [4]. Used as a single-agent therapy for SCCHN, this drug improved response rate, as well as median survival time, in comparison to cisplatin and 5-fluorouracil combination chemotherapy. However, 91% of the patients exposed to paclitaxel experienced neutropenia. Although OGF has been approved in Phase I trials [26], OGF has not been used clinically for the treatment of SCCHN. However, the efficacy of this compound for treatment of SCCHN has been demonstrated in xenograft experiments [16, 17]. The present report raises the exciting potential of combining chemotherapy and biotherapy into a novel treatment modality for SCCHN. With the preclinical information that a combination of OGF and paclitaxel has a synergistic effect on SCCHN in xenografts, the prospect of clinical studies should be considered.

REFERENCES

1. Arbuck S G, Cannetta R, Onetto N, Christian M C (1993) Current dosage and schedule issues in the development of paclitaxel (Taxol). Sem Oncol 20:31-39
2. Carew J F, and Shah J P (1998) Advances in multimodality therapy for laryngeal cancer. CA Cancer J Clin 48: 211-228
3. Carpinterio A, Peinert S, Ostertag W, Zander A R, Hossfeld D K, Kuhlcke K, Eckert H G, Baum C, Hegewisch-Becker S (2002) Generic protection of repopulating hematopoietic cells with an improved MDR1-retrovirus allows administration of intensified chemotherapy following stem cell transplantation in mice. Int J Cancer 98:785-792
4. Forastiere A A, Shank D, Neuberg D, Taylor S G, DeConti R C, Adams G (1998) Final report of a phase II evaluation of paclitaxel with advanced squamous cell carcinoma of the head and neck: An Eastern Cooperative Oncology Group trial (PA390). Cancer 82: 2270-2274
5. Hussain M, Gadgeel S, Kucuk O, Du W, Salwen W, Ensley J (1999) Paclitaxel, cisplatin, and 5-fluorouracil for patients with advanced or recurrent squamous cell carcinoma of the head and neck. Cancer 86: 2364-2369
6. Jemal A, Tiwari R C, Murray T, Ghafoor A, Samuels A, Ward E, Feuer E J, Thun M J (2004) Cancer statistics. CA Cancer J Clin 54:8-29
7. Kieback D G, Dagmar-Christiane F, Engehausen D G, Sauerbrei W, Oehler M K, Tong X-W, Aguilar-Cordova E (2002) Intraperitoneal adenovirus-mediated suicide gene therapy in combination with human ovarian cancer. Cancer Gene Therapy 9:478-481
8. Krause C J, Carey T E, Ott R W, Hurbis C, McClatchey K D, Regezi J A (1981) Human squamous cell carcinoma. Arch Otolaryngol 107: 703-710

9. Kurbacher C M, Mallmann P K (1998) Chemoprotection in anticancer therapy: The emerging role of amifostine. Anticancer Res 18:2203-2210
10. Leonard C E, Chan D C, Chou T-C, Kumar R, Bunn P A (1996) Paclitaxel enhances in vitro radiosensitivity of squamous carcinoma cell lines of the head and neck. Cancer Res 56: 5198-5204
11. Levin R J, Wu Y, McLaughlin P J, Zagon I S (1997) Expression of the opioid growth factor, [Met$^5$]-enkephalin, and the zeta opioid receptor in head and neck squamous cell carcinoma. Laryngoscope 107:335-339
12. Leyvraz S, Ohnuma T, Lassus M, Holland J F (1985) Phase I study in patients with advanced cancer, intermittent intravenous bolus, and 24-hour infusion. J Clin Oncol 3:1385-1392
13. McLaughlin P J, Jaglowski J R, Stack B C, Zagon I S (2004) Enhanced antitumor activity of paclitaxel on SCCHN with opioid growth factor (OGF): In vitro studies. FASEB J 18: A997
14. McLaughlin P J, Levin R J, Zagon I S (1999) Regulation of human head and neck squamous cell carcinoma growth in tissue culture by opioid growth factor. Int J Oncol 14: 991-998
15. McLaughlin P J, Levin R J, Zagon I S (2000) The opioid growth factor receptor (OGFr) in human head and neck squamous cell carcinoma. Int J Mol Med 5:191-196
16. McLaughlin P J, Levin R J, and Zagon I S (2003) Opioid growth factor (OGF) inhibits the progression of human squamous cell carcinoma of the head and neck transplanted into nude mice. Cancer Letters 199:209-217
17. McLaughlin P J, Stack B C, Braine K M, Ruda J D, Zagon I S (2004) Opioid growth factor (OGF) inhibition of a human squamous cell carcinoma of the head and neck in nude mice: Dependency on the route of administration. Int J Oncol 24:227-232
18. McLaughlin P J, Stack B C, Levin R J, Fedok F., Zagon I S (2003) Defects in the OGF receptor (OGFr) in human squamous cell carcinoma of the head and neck. Cancer 97:1701-1710
19. Parkin D M, Pisani P, Ferlay J (1999) Global cancer statistics. CA Cancer J Clin 49:33-64
20. Schantz S, Harrison L B, Forastiere A A (1997) Tumors of the nasal cavity and paranasal sinuses, nasopharynx, oral cavity, and oropharynx. In: DeVita V T, Hellman S, Rosenberg S A (eds) Cancer Principles and Practice of Oncology 5th edition pp. 741-801. Lippincott-Raven Philadelphia:
21. Schiff P B, Fant J, Horwitz S B (1979) Promotion of microtubule assembly in vitro by taxol. Nature 277:665-667
22. Schiff P B, Horwitz S B (1980) Taxol stabilizes microtubules in mouse fibroblast cells. Proc Natl Acad Sci USA 77:1561-1565
23. Shah J P, Lydiatt W (1995) Treatment of cancer of the head and neck. CA-Cancer J Clin 45:352-368
24. Shim W S N, Teh M, Mack P O P, Ge R (2001) Inhibition of angiopoietin-1 expression in tumor cells by an antisense RNA approach inhibited xenograft tumor growth in immunodeficient mice. Int J Cancer 94:6-15
25. Shin D M, Khuri F R, Glisson B S, Ginsberg L, Papadimitrakopoulou V M, Clayman G., Lee J J, Ang K K, Lippman S M, Hong W K (2001) Phase II study of paclitaxel, ifosafamide, and carboplatin in patients with recurrent or metastatic head and neck squamous cell carcinoma. Cancer 91:1316-1323
26. Smith J P, Conter R L, Bingaman S I, Harvey H A, Mauger D T, Ahmad M, Demers L M, Stanley W B, McLaughlin P J, Zagon I S (2004) Treatment of advanced pancreatic cancer with opioid growth factor: Phase I. Anti-Cancer Drugs 15:203-209
27. Srivastava R K, Srivastava A R, Korsmeyer S J, Nesterova M, Cho-Chung Y S, Longo D L (1998) Involvement of microtubules in the regulation of Bcl2 phosphorylation and apoptosis through cyclic AMP-dependent protein kinase. Mol Cell Biol 18:3509-3517
28. Villena-Heinsen C, Friedrich M, Ertan A K, Farnhammer C, Schmidt W (1998) Human ovarian cancer xenografts in nude mice: Chemotherapy trials with paclitaxel, cisplatin, vinorelbine and titanocene dichloride. Anticancer Drugs 9:557-563
29. Vokes E E, Haraf D J, Stenson K, Stupp R, Malone D, Levin J, Weichselbaum R R (1995) The role of paclitaxel in the treatment of head and neck cancer. Sem Oncol 22:8-12
30. Wilson R P, McLaughlin P J, Lang C M, Zagon I S (2000) The opioid growth factor, [Met$^5$]-enkephalin, inhibits DNA synthesis during recornification of mouse tail skin. Cell Proliferation 33:63-73
31. Zagon I S, McLaughlin P J (2003) Opioids and the apoptotic pathway in human cancer cells. Neuropeptides 37:79-88
32. Zagon I S, Roesener C D, Verderame M F, Ohlsson-Wilhelm B M, Levin R J, McLaughlin P J (2000) Opioid growth factor regulates the cell cycle of human neoplasias. Int J Oncol 17:1053-1061
33. Zagon I S, Verderame M F, Allen S S, McLaughlin P J (2000) Cloning, sequencing, chromosomal location, and function of a cDNA encoding the opioid growth factor receptor (OGFr) in humans. Brain Res 856:75-83
34. Zagon I S, Wu Y, McLaughlin P J (1994) Opioid growth factor (OGF) inhibits DNA synthesis in mouse tongue epithelium in a circadian-rhythm-dependent manner. Am J Physiol 267:R645-R652
35. Zagon I S, Wu Y, McLaughlin P J (1999) Opioid growth factor and organ development in rat and human embryos. Brain Res 839:313-322

TABLE 8

Incidence and latency for tumor appearance of SCC-1 squamous cell carcinoma cells in nude mice treated with OGF and/or paclitaxel.

| Parameter | Control | OGF | Paclitaxel | Paclitaxel/OGF |
|---|---|---|---|---|
| N | 12 | 12 | 12 | 10 |
| Incidence of measurable tumor (day 13) | 9/12 | 4/12$^a$ | 8/12 | 7/10 |
| Incidence of measurable tumor (day 17) | 12/12 | 8/12 | 10/12 | 9/10 |
| Latency to visible tumor (days) | 7.2 ± 0.5 | 11.2 ± 1.5$^b$ | 7.4 ± 1.4 | 8.6 ± 0.8 |
| Latency to measurable tumor (days) | 14.2 ± 0.6 | 17.0 ± 1.5 | 14.8 ± 1.7 | 15.5 ± 1.5 |

Values represent means ± SEM.
$^a$Significantly different from the control group by Chi-square analyses at $p < 0.05$.
$^b$Significantly different at $p < 0.02$ from controls using ANOVA.

TABLE 9

Characteristics of nude mice 50 days after subcutaneous inoculation of SCC-1 squamous carcinoma cells and treatment (i.p.) with OGF and/or paclitaxel

| Parameter | Controls | OGF | Paclitaxel | Paclitaxel/OGF |
|---|---|---|---|---|
| Body Weight, g | 31.6 ± 0.7 | 32.0 ± 0.5 | 22.6 ± 0.8*** | +++ ^^^ 31.8 ± 1.1 |
| Tumor Weight, g | 2.4 ± 0.2 | 1.7 ± 0.2** | N.A. | 0.9 ± 0.7***+++ |
| Tumor Volume, mm$^3$ | 3896 ± 535 | 590 ± 364* | N.A. | 1223 ± 238***+ |
| Spleen Weight, mg | 243 ± 25 | 25 ± 12 | 243 ± 8 | 197 ± 19 |
| Metastases | none | none | none | none |

Data represent means ± SEM.
N.A. = data not available because only one mouse was alive on day 50; spleen and body weights for the paclitaxel group only were calculated on the day each mouse died.
Significantly different from controls at $p < 0.05$ (*), $p < 0.01$ () and $p < 0.001$(*).
Significantly different from OGF group at $p < 0.05$ (+) and $p < 0.001$ (+++).
Significantly different from the paclitaxel-treated mice at $p < 0.001$ (^^^).

TABLE 10

Receptor binding analysis of OGFr in SCC-1 tumors from mice treated with OGF and/or paclitaxel.

| | Controls | OGF | Paclitaxel | Paclitaxel/OGF |
|---|---|---|---|---|
| $K_d$, nM | 1.0 ± 0.1 | 2.1 ± 0.3 | 1.2 ± 0.2 | 1.4 ± 0.3 |
| $B_{max}$, fmol/mg protein | 14.9 ± 1.2 | 27.2 ± 2.2* | 27.8 ± 1.6* | 20.5 ± 2.1 |

Data represent means ± SEM.
Significantly different from controls at $p < 0.05$ (*).

It should be understood that the embodiments described herein are for illustrative purposes only and that various modifications or changes in light thereof will be suggested to persons skilled in the art and are to be included within the spirit and purview of this application.

The invention claimed is:

1. A pharmaceutical composition for treating neoplasias in an animal or human, comprising:
   therapeutically effective amounts of at least one therapeutic agent comprising at least one chemotherapeutic agent selected from the group consisting of gemcitabine and paclitaxel,
   an opioid growth factor; and
   a carrier.

2. The pharmaceutical composition of claim 1, wherein said composition comprises opioid growth factor and gemcitabine.

3. The pharmaceutical composition of claim 1, wherein said composition comprises opioid growth factor and paclitaxel.

4. The pharmaceutical composition of claim 1, wherein said composition comprises opioid growth factor, gemcitabine and paclitaxel.

* * * * *